(12) United States Patent
Moriguchi et al.

(10) Patent No.: US 10,487,045 B2
(45) Date of Patent: Nov. 26, 2019

(54) ADAMANTANE DERIVATIVE AND USE THEREOF

(71) Applicants: TOHOKU UNIVERSITY, Aoba-ku, Sendai-shi, Miyagi (JP); Brain Innovation Co., Inc., Aoba-ku, Sendai-shi, Miyagi (JP)

(72) Inventors: Shigeki Moriguchi, Miyagi (JP); Koji Fukunaga, Miyagi (JP); Yoshiharu Iwabuchi, Miyagi (JP)

(73) Assignees: Tohoku University, Miyagi (JP); Brain Innovation Co., Inc., Miyagi (JP)

( * ) Notice: Subject to any disclaimer, the term of this patent is extended or adjusted under 35 U.S.C. 154(b) by 0 days.

(21) Appl. No.: 16/072,586

(22) PCT Filed: Jan. 26, 2017

(86) PCT No.: PCT/JP2017/002760
§ 371 (c)(1),
(2) Date: Jul. 25, 2018

(87) PCT Pub. No.: WO2017/131097
PCT Pub. Date: Aug. 3, 2017

(65) Prior Publication Data
US 2019/0055191 A1 Feb. 21, 2019

(30) Foreign Application Priority Data

Jan. 26, 2016 (JP) ................................ 2016-012392

(51) Int. Cl.
| | |
|---|---|
| C07C 229/28 | (2006.01) |
| C07C 247/14 | (2006.01) |
| C07C 233/47 | (2006.01) |
| C07D 213/40 | (2006.01) |
| A61K 31/198 | (2006.01) |
| A61K 31/221 | (2006.01) |
| A61K 31/223 | (2006.01) |
| A61K 31/655 | (2006.01) |
| A61P 25/28 | (2006.01) |
| A61P 3/10 | (2006.01) |
| A61P 25/16 | (2006.01) |

(52) U.S. Cl.
CPC .......... *C07C 229/28* (2013.01); *A61K 31/198* (2013.01); *A61K 31/221* (2013.01); *A61K 31/223* (2013.01); *A61K 31/655* (2013.01); *A61P 3/10* (2018.01); *A61P 25/16* (2018.01); *A61P 25/28* (2018.01); *C07C 233/47* (2013.01); *C07C 247/14* (2013.01); *C07D 213/40* (2013.01)

(58) Field of Classification Search
CPC ... C07C 229/28; C07C 247/14; C07C 233/47; C07D 213/40
See application file for complete search history.

(56) References Cited

U.S. PATENT DOCUMENTS

| | | |
|---|---|---|
| 2006/0223855 A1 | 10/2006 | Kong et al. |
| 2007/0072892 A1 | 3/2007 | Schrimpf et al. |
| 2008/0255180 A1 | 10/2008 | Bunnelle |
| 2010/0022546 A1 | 1/2010 | Jimenenz et al. |
| 2010/0197675 A1 | 8/2010 | Claremon et al. |
| 2011/0212943 A1 | 9/2011 | Balasubramanian et al. |
| 2012/0270873 A1 | 10/2012 | Jiminez et al. |
| 2013/0045177 A1 | 2/2013 | Takatoku et al. |
| 2014/0135306 A1* | 5/2014 | Buschmann ......... C07D 217/24 514/210.18 |

FOREIGN PATENT DOCUMENTS

| | | |
|---|---|---|
| CA | 3012312 A1 | 8/2017 |
| CN | 104001150 A | 8/2014 |
| CN | 107556244 A | 1/2018 |
| JP | 2008-525425 A | 7/2008 |
| JP | 2009-508956 A | 3/2009 |
| JP | 2010-519304 A | 6/2010 |
| JP | 2010-522203 A | 7/2010 |
| JP | 2011-529057 A | 12/2011 |
| WO | WO 2009/020140 A1 | 2/2009 |
| WO | WO 2010/043953 A2 | 4/2010 |
| WO | WO 2011/142246 A1 | 11/2011 |
| WO | WO 2015/087262 A1 | 6/2015 |
| WO | WO 2017/131097 A1 | 8/2017 |

OTHER PUBLICATIONS

International Search Report dated Mar. 21, 2017, in PCT/JP2017/002760.
International Search Report dated Jun. 27, 2017, in PCT/JP2017/013616.
International Search Report dated Jun. 19, 2018, in PCT/JP2018/013853.
Database Registry, 2016, RN 1981386-54-2, RN 1980645-09-7, RN 1979117-44-6, RN 197690374-8, RN 1975313-60-0, RN 1974817-09-8, RN 1974644-59-1, retrieved from SIN international (online) on Jun. 4, 2018, 4 pages.

(Continued)

*Primary Examiner* — Matthew P Coughlin
(74) *Attorney, Agent, or Firm* — Foley & Lardner LLP

(57) ABSTRACT

The present invention provides a pharmaceutical composition for treating or preventing a cognitive disease or disorder, containing a compound represented by Formula (I), an enantiomer thereof, a diastereomer thereof, or a pharmaceutically acceptable salt thereof.

13 Claims, 44 Drawing Sheets

Specification includes a Sequence Listing.

(56) References Cited

OTHER PUBLICATIONS

Database Registry, 2015, RN 1782740-93-5, retrieved from SIN international (online) on Jun. 4, 2018, 1 page.
Folia Pharmacologica Japonica, 2004, 124:145-151, with English Abstract on last page.
Folia Pharmacoloaica Japonica, 2005, 126:311-316, with English abstract.
Lachenicht et al., "Synthesis of Modified 4H-1,2,4-Benzothiadizine-1,1-dioxides and Determination of their Affinity and Selectivity for Different Types of $K_{ATP}$ Channels," ChemMedChem, 2009, 4(11):1850-1858.
Moriguchi et al., "Blockade of the $K_{ATP}$ channel Kir6.2 by memantine represents a novel mechanism relevant to Alzheimer's disease therapy," Molecular Psychiatry, 2016, advance online publication, 1-11.
Teramoto, Noriyoshi, "Pharmacological Profile of U-37883A, a Channel Blocker of Smooth Muscle-Type ATP-Sensitive $K^+$ Channels," Cardiovascular Drug Reviews, 2005, 24(1):25-32.
Teramoto, Noriyoshi, "Pharmacological Profile of U-37883A, a Channel Blocker of Smooth Muscle-Type ATP-Sensitive $K^+$ Channels," Cardiovascular Drug Reviews, 2006, 24(1):25-32.
International Search Report dated Oct. 23, 2018, in PCT/JP2018/029018.
Registry (STN), Sep. 11, 2016, RN: 1990660-80-4 to 1499084-76-2, retrieved from STN International [online] on Oct. 10, 2018.

* cited by examiner

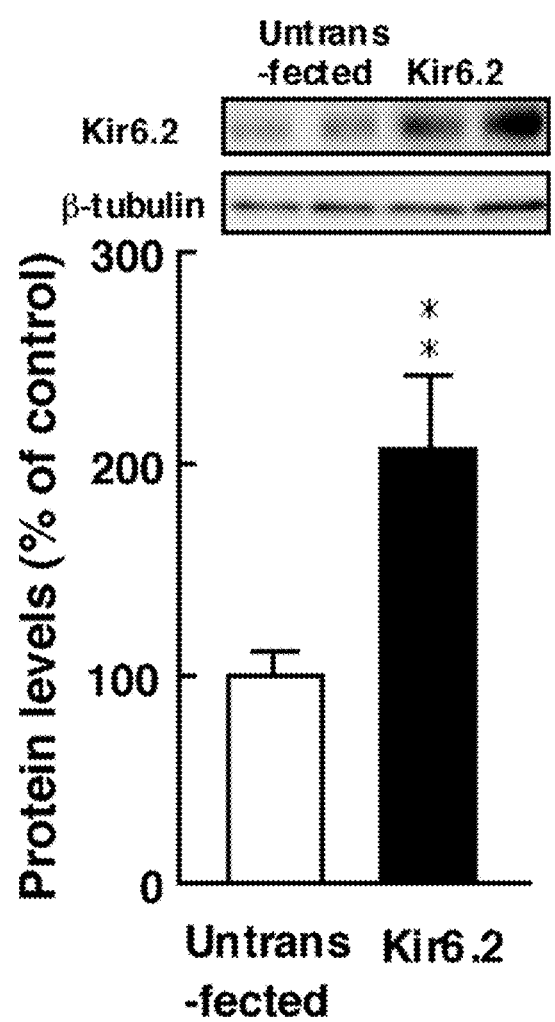

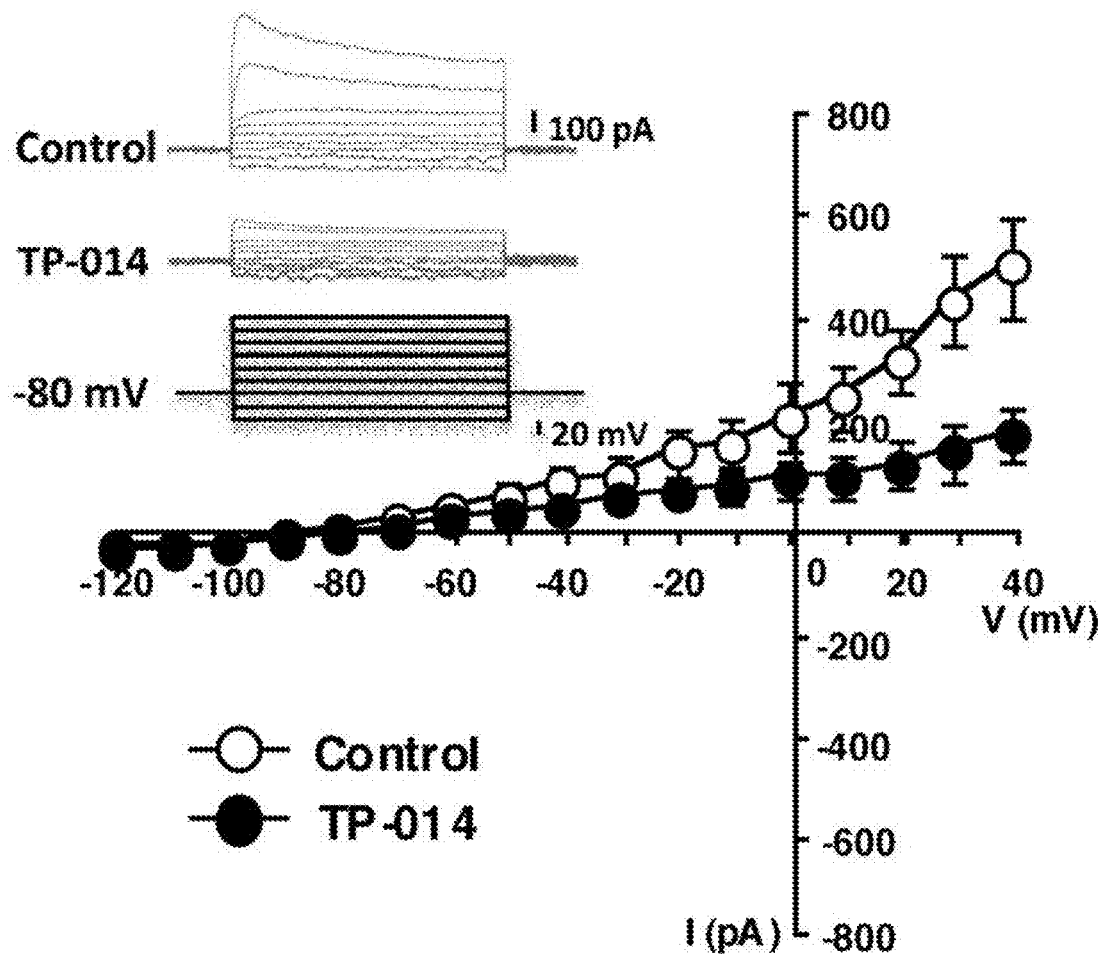

Fig. 17-1

```
   1  GACGGATCGG GAGATCTCCC GATCCCTAT  GGTGCACTCT CAGTACAATC TGCTCTGATG
  61  CGGTATAGTT AAGCCAGTAT CTGCTCCCTG CTTGTGTGTT GGAGGTCGCT GAGTAGTGCG
 121  CGAGCAAAAT TTAAGCTACA ACAAGGCAAG GCTTGACCGA CAATTGCATG AAGAATCTGC
                                                        CMV promoter
 181  TTAGGGTTAG GCGTTTTGCG CTGCTTCGCG ATGTACGGGC CAGATATACG CGTTGACATT
                                    CMV promoter
 241  GATTATTGAC TAGTTATTAA TAGTAATCAA TTACGGGGTC ATTAGTTCAT AGCCCATATA
                                    CMV promoter
 301  TGGAGTTCCG CGTTACATAA CTTACGGTAA ATGGCCCGCC TGGCTGACCG CCCAACGACC
                                    CMV promoter
 361  CCCGCCCATT GACGTCAATA ATGACGTATG TTCCCATAGT AACGCCAATA GGGACTTTCC
                                    CMV promoter
 421  ATTGACGTCA ATGGGTGGAC TATTTACGGT AAACTGCCCA CTTGGCAGTA CATCAAGTGT
                                    CMV promoter
 481  ATCATATGCC AAGTACGCCC CCTATTGACG TCAATGACGG TAAATGGCCC GCCTGGCATT
                                    CMV promoter
 541  ATGCCCAGTA CATGACCTTA TGGGACTTTC CTACTTGGCA GTACATCTAC GTATTAGTCA
                                    CMV promoter
 601  TCGCTATTAC CATGGTGATG CGGTTTTGGC AGTACATCAA TGGGCGTGGA TAGCGGTTTG
                                    CMV promoter
 661  ACTCACGGGG ATTTCCAAGT CTCCACCCCA TTGACGTCAA TGGGAGTTTG TTTTGGCACC
                                                                    CMV forward primer
                                    CMV promoter
 721  AAAATCAACG GGACTTTCCA AAATGTCGTA ACAACTCCGC CCCATTGACG CAAATGGGCG
       CMV forward prime
                                    CMV promoter
 781  GTAGGCGTGT ACGGTGGGAG GTCTATATAA GCAGAGCTCT CTGGCTAACT AGAGAACCCA
                                                T7 primer
                    CMV promoter
                                                T7 promoter
 841  CTGCTTACTG GCTTATCGAA ATTAATACGA CTCACTATAG GGAGACCCAA GCTGGCTAGT
         HindIII             BamHI                         Kir6.2
  +2                                            M  L  S  R  K  G  I  I  P  E
 901  TAAGCTTGGT ACCGAGCTCG GATCCGCCAC CATGCTGTCC CGAAGGGCA TTATCCCTGA
                                    Kir6.2
  +2   E  E  Y  V  L  T  R  L  A  E  D  P  T  E  P  R  Y  R  T  R  E
 961  GGAATATGTG CTGACCCGGC TGGCAGAGGA CCCTACAGAG CCCAGGTACC GTACTCGGGA
                                    Kir6.2
  +2   R  R  A  R  F  V  S  K  K  G  N  C  N  V  A  H  K  N  I  R
1021  GAGGAGGGCC CGCTTCGTGT CCAAGAAAGG CAACTGCAAC GTCGCCCACA AGAACATCCG
                                    Kir6.2
  +2   R  E  Q  G  R  F  L  Q  D  V  F  T  T  L  V  D  L  K  W  P  H
1081  AGAGCAGGGC CGCTTCCTGC AAGATGTGTT CACCACGCTG GTGGACCTCA AGTGGCCCCA
                                    Kir6.2
  +2   H  T  L  L  I  F  T  M  S  F  L  G  S  W  L  L  F  A  M  V  W
1141  CACGCTGCTC ATTTTCACCA TGTCCTTCCT GTGCAGCTGG CTGCTCTTCG CCATGGTCTG
                                    Kir6.2
  +2   W  W  L  I  A  F  A  H  G  D  L  A  P  G  E  G  T  N  V  P  C
1201  GTGGCTCATC GCCTTTGCCC ACGGTGACTT GGCCCCCGGA GAGGGCACCA ATGTGCCCTG
```

Fig. 17-2

```
                                    Kir6.2
      +2  ·C  V   T   S   I   H   S   F   S   S   A   F   L   F   S   I   E   V   G   V   T·
    1261  CGTCACAAGC  ATCCACTCCT  TTTCGTCTGC  CTTCCTTTTC  TCCATCGAGG  TCCAGGTGAC
                                    Kir6.2
      +2  ·T   I   G   F   G   G   R   M   V   T   E   E   C   P   L   A   I   L   I   L   I·
    1321  CATTGGTTTC  GGCGGGCGCA  TGGTGACAGA  GGAATGTCCC  CTGGCCATCC  TTATTCTGAT
                                    Kir6.2
      +2  ·I   V   Q   N   I   V   G   L   M   I   N   A   I   M   L   G   C   I   F   M   K·
    1381  CGTGCAGAAT  ATCGTAGGGC  TAATGATCAA  CGCCATCATG  CTGGGCTGCA  TCTTCATGAA
                                    Kir6.2
      +2  ·K   T   A   Q   A   H   R   R   A   E   T   L   I   F   S   K   H   A   V   I   T·
    1441  AACGGCACAG  GCCCATCGGC  GGGCAGAAAC  CCTCATCTTC  AGCAAGCATG  CCGTGATCAC
                                    Kir6.2
      +2  ·T   L   R   H   G   R   L   C   F   M   L   R   V   G   D   L   R   K   S   M   I·
    1501  CCTGCGACAT  GGCCGCCTGT  GCTTCATGCT  TCGCGTAGGG  GACCTCCGAA  AAGCATGAT
                                    Kir6.2
      +2  ·I   I   S   A   T   I   H   M   Q   V   V   R   K   T   T   S   P   E   G   E   V·
    1561  CATTAGCGCC  ACCATTCATA  TGCAGGTGGT  GCGCAAGACC  ACCAGCCCGG  AGGGCGAGGT
                                    Kir6.2
      +2  ·V   V   P   L   H   G   V   D   I   P   M   E   N   G   V   G   G   N   S   I   F·
    1621  TGTGCCTCTC  CACCAGGTGG  ACATCCCCAT  GGAGAACGGT  GTGGGTGGTA  ACAGCATCTT
                                    Kir6.2
      +2  ·F   L   V   A   P   L   I   I   Y   H   V   I   D   S   N   S   P   L   Y   D   L·
    1681  TCTGGTGGCC  CCACTCATCA  TCTACCACGT  CATCGACTCC  AACAGCCCGC  TCTACGACCT
                                    Kir6.2
      +2  ·L   A   P   S   D   L   H   H   H   Q   D   L   E   I   I   V   I   L   E   G   V·
    1741  GGCTCCTAGT  GACCTGCACC  ACCACCAGGA  CCTGGAGATC  ATTGTCATCT  TGGAAGGTGT
                                    Kir6.2
      +2  ·V   V   E   T   T   G   I   T   T   Q   A   R   T   S   Y   L   A   D   E   I   L·
    1801  GGTAGAAACC  ACAGGCATTA  CCACCCAGGC  CCGCACCTCC  TATCTGGCTG  ACGAGATTCT
                                    Kir6.2
      +2  ·L   W   G   Q   R   F   V   P   I   V   A   E   E   D   G   R   Y   S   V   D   Y·
    1861  GTGGGGGCAG  CGTTTTGTCC  CCATCGTGGC  CGAGGAGGAT  GGCCGCTATT  CTGTGGACTA
                                    Kir6.2
      +2  ·Y   S   K   F   G   N   T   V   K   V   P   T   P   L   C   T   A   R   Q   L   D·
    1921  CTCCAAATTC  GGGAACACCG  TTAAAGTGCC  CACACCACTC  TGCACAGCCC  GCCAGCTTGA
                                    Kir6.2
      +2  ·D   E   D   R   S   L   L   D   A   L   T   L   A   S   S   R   G   P   L   R   K·
    1981  TGAGGACCGC  AGCCTGCTGG  ATGCCCTGAC  CCTCGCCTCG  TCGCGAGGGC  CCCTGCGCAA
                                    Kir6.2
      +2  ·K   R   S   V   A   V   A   K   A   K   P   K   F   S   I   S   P   D   S   L   S·
    2041  GCGCAGTGTG  GCTGTGGCAA  AGGCCAAGCC  CAAGTTTAGC  ATCTCTCCGG  ATTCCTTGTC
              Kir6.2     NotI         XbaI           StuI
                                Xhol
      +2  ·S·
    2101  CTGATAGCGG  CCGCTCGAGT  CTAGAGGGCC  CTTCGAACAA  AAACTCATCT  CAGAAGAGGA
                         AgeI                          PmeI         BGH pA
    2161  TCTGAATATG  CATACCGGTC  ATCATCACCA  TCACCATTGA  GTTTAAACCC  GCTGATCAGC
                                                                     BGH reverse prime
                                BGH pA
    2221  CTCGACTGTG  CCTTCTAGTT  GCCAGCCATC  TGTTGTTTGC  CCCTCCCCCG  TGCCTTCCTT
          BGH reverse primer
```

Fig. 17-3

```
                                               BGH pA
2281   GACCCTGGAA  GGTGCCACTC  CCACTGTCCT  TTCCTAATAA  AATGAGGAAA  TTGCATCGCA
                                               BGH pA
2341   TTGTCTGAGT  AGGTGTCATT  CTATTCTGGG  GGGTGGGGTG  GGGCAGGACA  GCAAGGGGGA
                     BGH pA
2401   GGATTGGGAA  GACAATAGCA  GGCATGCTGG  GGATGCGGTG  GGCTCTATGG  CTTCTGAGGC
                                                                     f1 origin
2461   GGAAAGAACC  AGCTGGGGCT  CTAGGGGGTA  TCCCCACGCG  CCCTGTAGCG  GCGCATTAAG
                                      f1 origin
2521   CGCGGCGGGT  GTGGTGGTTA  CGCGCAGCGT  GACCGCTACA  CTTGCCAGCG  CCCTAGCGCC
                                      f1 origin
2581   CGCTCCTTTC  GCTTTCTTCC  CTTCCTTTCT  CGCCACGTTC  GCCGGCTTTC  CCCGTCAAGC
                                      f1 origin
2641   TCTAAATCGG  GGGCTCCCTT  TAGGGTTCCG  ATTTAGTGCT  TTACGGCACC  TCGACCCCAA
                                      f1 origin
2701   AAAACTTGAT  TAGGGTGATG  GTTCACGTAG  TGGGCCATCG  CCCTGATAGA  CGGTTTTTCG
                                      f1 origin
2761   CCCTTTGACG  TTGGAGTCCA  CGTTCTTTAA  TAGTGGACTC  TTGTTCCAAA  CTGGAACAAC
                                      f1 origin
2821   ACTCAACCCT  ATCTCGGTCT  ATTCTTTTGA  TTTATAAGGG  ATTTTGCCGA  TTTCGGCCTA
                                      f1 origin
2881   TTGGTTAAAA  AATGAGCTGA  TTTAACAAAA  ATTTAACGCG  AATTAATTCT  GTGGAATGTG
                                                                   SV40 early promoter
2941   TGTCAGTTAG  GGTGTGGAAA  GTCCCCAGGC  TCCCCAGCAG  GCAGAAGTAT  GCAAAGCATG
                                 SV40 early promoter
3001   CATCTCAATT  AGTCAGCAAC  CAGGTGTGGA  AAGTCCCCAG  GCTCCCCAGC  AGGCAGAAGT
                                 SV40 early promoter
3061   ATGCAAAGCA  TGCATCTCAA  TTAGTCAGCA  ACCATAGTCC  CGCCCCTAAC  TCCGCCCATC
                                 SV40 early promoter
3121   CCGCCCCTAA  CTCCGCCCAG  TTCCGCCCAT  TCTCCGCCCC  ATGGCTGACT  AATTTTTTTT
                                 SV40 early promoter
3181   ATTTATGCAG  AGGCCGAGGC  CGCCTCTGCC  TCTGAGCTAT  TCCAGAAGTA  GTGAGGAGGC
                                 SV40 early promoter
3241   TTTTTTGGAG  GCCTAGGCTT  TTGCAAAAAG  CTCCCGGGAG  CTTGTATATC  CATTTTCGGA
                                                                   Neo(R)
3301   TCTGATCAAG  AGACAGGATG  AGGATCGTTT  CGCATGATTG  AACAAGATGG  ATTGCACGCA
                                      Neo(R)
3361   GGTTCTCCGG  CCGCTTGGGT  GGAGAGGCTA  TTCGGCTATG  ACTGGGCACA  ACAGACAATC
                                      Neo(R)
3421   GGCTGCTCTG  ATGCCGCCGT  GTTCCGGCTG  TCAGCGCAGG  GGCGCCCGGT  TCTTTTTGTC
                                      Neo(R)
3481   AAGACCGACC  TGTCCGGTGC  CCTGAATGAA  CTGCAGGACG  AGGCAGCGCG  GCTATCGTGG
                                      Neo(R)
3541   CTGGCCACGA  CGGGCGTTCC  TTGCGCAGCT  GTGCTCGACG  TTGTCACTGA  AGCGGGAAGG
                                      Neo(R)
3601   GACTGGCTGC  TATTGGGCGA  AGTGCCGGGG  CAGGATCTCC  TGTCATCTCA  CCTTGCTCCT
                                      Neo(R)
3661   GCCGAGAAAG  TATCCATCAT  GGCTGATGCA  ATGCGGCGGC  TGCATACGCT  TGATCCGGCT
                                      Neo(R)
3721   ACCTGCCCAT  TCGACCACCA  AGCGAAACAT  CGCATCGAGC  GAGCACGTAC  TCGGATGGAA
```

Fig. 17-4

```
                                          Neo(R)
3781  GCCGGTCTTG TCGATCAGGA TGATCTGGAC GAAGAGCATC AGGGGCTCGC GCCAGCCGAA
                                          Neo(R)
3841  CTGTTCGCCA GGCTCAAGGC GCGCATGCCC GACGGCGAGG ATCTCGTCGT GACCCATGGC
                                          Neo(R)
3901  GATGCCTGCT TGCCGAATAT CATGGTGGAA AATGGCCGCT TTTCTGGATT CATCGACTGT
                                          Neo(R)
3961  GGCCGGCTGG GTGTGGCGGA CCGCTATCAG GACATAGCGT TGGCTACCCG TGATATTGCT
                                          Neo(R)
4021  GAAGAGCTTG GCGGCGAATG GGCTGACCGC TTCCTCGTGC TTTACGGTAT CGCCGCTCCC
                                    Neo(R)
4081  GATTCGCAGC GCATCGCCTT CTATCGCCTT CTTGACGAGT TCTTCTGAGC GGGACTCTGG
4141  GGTTCGCGAA ATGACCGACC AAGCGACGCC CAACCTGCCA TCACGAGATT TCGATTCCAC
4201  CGCCGCCTTC TATGAAAGGT TGGGCTTCGG AATCGTTTTC CGGGACGCCG GCTGGATGAT
                                                              SV40 pA
4261  CCTCCAGCGC GGGGATCTCA TGCTGGAGTT CTTCGCCCAC CCCAACTTGT TTATTGCAGC
                  SV40 pA
4321  TTATAATGGT TACAAATAAA GCAATAGCAT CACAAATTTC ACAAATAAAG CATTTTTTTC
               SV40 pA
4381  ACTGCATTCT AGTTGTGGTT TGTCCAAACT CATCAATGTA TCTTATCATG TCTGTATACC
4441  GTCGACCTCT AGCTAGAGCT TGGCGTAATC ATGGTCATAG CTGTTTCCTG TGTGAAATTG
4501  TTATCCGCTC ACAATTCCAC ACAACATACG AGCCGGAAGC ATAAAGTGTA AAGCCTGGGG
4561  TGCCTAATGA GTGAGCTAAC TCACATTAAT TGCGTTGCGC TCACTGCCCG CTTTCCAGTC
4621  GGGAAACCTG TCGTGCCAGC TGCATTAATG AATCGGCCAA CGCGCGGGGA GAGGCGGTTT
4681  GCGTATTGGG CGCTCTTCCG CTTCCTCGCT CACTGACTCG CTGCGCTCGG TCGTTCGGCT
4741  GCGGCGAGCG GTATCAGCTC ACTCAAAGGC GGTAATACGG TTATCCACAG AATCAGGGGA
4801  TAACGCAGGA AAGAACATGT GAGCAAAAGG CCAGCAAAAG GCCAGGAACC GTAAAAAGGC
                                                          pUC origin
4861  CGCGTTGCTG GCGTTTTTCC ATAGGCTCCG CCCCCCTGAC GAGCATCACA AAAATCGACG
                                          pUC origin
4921  CTCAAGTCAG AGGTGGCGAA ACCCGACAGG ACTATAAAGA TACCAGGCGT TTCCCCCTGG
                                          pUC origin
4981  AAGCTCCCTC GTGCGCTCTC CTGTTCCGAC CCTGCCGCTT ACCGGATACC TGTCCGCCTT
                                          pUC origin
5041  TCTCCCTTCG GGAAGCGTGG CGCTTTCTCA TAGCTCACGC TGTAGGTATC TCAGTTCGGT
                                          pUC origin
5101  GTAGGTCGTT CGCTCCAAGC TGGGCTGTGT GCACGAACCC CCCGTTCAGC CCGACCGCTG
                                          pUC origin
5161  CGCCTTATCC GGTAACTATC GTCTTGAGTC CAACCCGGTA AGACACGACT TATCGCCACT
                                          pUC origin
5221  GGCAGCAGCC ACTGGTAACA GGATTAGCAG AGCGAGGTAT GTAGGCGGTG CTACAGAGTT
                                          pUC origin
5281  CTTGAAGTGG TGGCCTAACT ACGGCTACAC TAGAAGAACA GTATTTGGTA TCTGCGCTCT
                                          pUC origin
5341  GCTGAAGCCA GTTACCTTCG GAAAAAGAGT TGGTAGCTCT TGATCCGGCA AACAAACCAC
                                          pUC origin
5401  CGCTGGTAGC GGTGGTTTTT TTGTTTGCAA GCAGCAGATT ACGCGCAGAA AAAAGGATC
                                          pUC origin
```

Fig. 17-5

```
5461  TCAAGAAGAT CCTTTGATCT TTTCTACGGG GTCTGACGCT CAGTGGAACG AAAACTCACG
                 pUC origin
5521  TTAAGGGATT TTGGTCATGA GATTATCAAA AAGGATCTTC ACCTAGATCC TTTTAAATTA
5581  AAAATGAAGT TTTAAATCAA TCTAAAGTAT ATATGAGTAA ACTTGGTCTG ACAGTTACCA
                                                                Amp(R)
5641  ATGCTTAATC AGTGAGGCAC CTATCTCAGC GATCTGTCTA TTTCGTTCAT CCATAGTTGC
                                      Amp(R)
5701  CTGACTCCCC GTCGTGTAGA TAACTACGAT ACGGGAGGGC TTACCATCTG GCCCCAGTGC
                                      Amp(R)
5761  TGCAATGATA CCGCGAGACC CACGCTCACC GGCTCCAGAT TTATCAGCAA TAAACCAGCC
                                      Amp(R)
5821  AGCCGGAAGG GCCGAGCGCA GAAGTGGTCC TGCAACTTTA TCCGCCTCCA TCCAGTCTAT
                                      Amp(R)
5881  TAATTGTTGC CGGGAAGCTA GAGTAAGTAG TTCGCCAGTT AATAGTTTGC GCAACGTTGT
                                      Amp(R)
5941  TGCCATTGCT ACAGGCATCG TGGTGTCACG CTCGTCGTTT GGTATGGCTT CATTCAGCTC
                                      Amp(R)
6001  CGGTTCCCAA CGATCAAGGC GAGTTACATG ATCCCCCATG TTGTGCAAAA AAGCGGTTAG
                                      Amp(R)
6061  CTCCTTCGGT CCTCCGATCG TTGTCAGAAG TAAGTTGGCC GCAGTGTTAT CACTCATGGT
                                      Amp(R)
6121  TATGGCAGCA CTGCATAATT CTCTTACTGT CATGCCATCC GTAAGATGCT TTTCTGTGAC
                                      Amp(R)
6181  TGGTGAGTAC TCAACCAAGT CATTCTGAGA ATAGTGTATG CGGCGACCGA GTTGCTCTTG
                                      Amp(R)
6241  CCCGGCGTCA ATACGGGATA ATACCGCGCC ACATAGCAGA ACTTTAAAAG TGCTCATCAT
                                      Amp(R)
6301  TGGAAAACGT TCTTCGGGGC GAAAACTCTC AAGGATCTTA CCGCTGTTGA GATCCAGTTC
                                      Amp(R)
6361  GATGTAACCC ACTCGTGCAC CCAACTGATC TTCAGCATCT TTTACTTTCA CCAGCGTTTC
                                      Amp(R)
6421  TGGGTGAGCA AAAACAGGAA GGCAAAATGC CGCAAAAAAG GGAATAAGGG CGACACGGAA
                                      Amp(R)
6481  ATGTTGAATA CTCATACTCT TCCTTTTTCA ATATTATTGA AGCATTTATC AGGGTTATTG
                                                               bla promoter
            Amp(R)
6541  TCTCATGAGC GGATACATAT TTGAATGTAT TTAGAAAAAT AAACAAATAG GGGTTCCGCG
                                          bla promoter
6601  CACATTTCCC CGAAAAGTGC CACCTGACGT C
```

Fig. 21-1

```
   1  GACGGATCGG  GAGATCTCCC  GATCCCTAT   GGTGCACTCT  CAGTACAATC  TGCTCTGATG
  61  CCGCATAGTT  AAGCCAGTAT  CTGCTCCCTG  CTTGTGTGTT  GGAGGTCGCT  GAGTAGTGCG
 121  CGAGCAAAAT  TTAAGCTACA  ACAAGGCAAG  GCTTGACCGA  CAATTGCATG  AAGAATCTGC
                                                           ─────── CMV promoter ───────
 181  TTAGGGTTAG  GCGTTTTGCG  CTGCTTCGCG  ATGTACGGGC  CAGATATACG  CGTTGACATT
      ──────────────────────────────────── CMV promoter ────────────────────────────────────
 241  GATTATTGAC  TAGTTATTAA  TAGTAATCAA  TTACGGGGTC  ATTAGTTCAT  AGCCCATATA
      ──────────────────────────────────── CMV promoter ────────────────────────────────────
 301  TGGAGTTCCG  CGTTACATAA  CTTACGGTAA  ATGGCCCGCC  TGGCTGACCG  CCCAACGACC
      ──────────────────────────────────── CMV promoter ────────────────────────────────────
 361  CCCGCCCATT  GACGTCAATA  ATGACGTATG  TTCCCATAGT  AACGCCAATA  GGGACTTTCC
      ──────────────────────────────────── CMV promoter ────────────────────────────────────
 421  ATTGACGTCA  ATGGGTGGAC  TATTTACGGT  AAACTGCCCA  CTTGGCAGTA  CATCAAGTGT
      ──────────────────────────────────── CMV promoter ────────────────────────────────────
 481  ATCATATGCC  AAGTACGCCC  CCTATTGACG  TCAATGACGG  TAAATGGCCC  GCCTGGCATT
      ──────────────────────────────────── CMV promoter ────────────────────────────────────
 541  ATGCCCAGTA  CATGACCTTA  TGGGACTTTC  CTACTTGGCA  GTACATCTAC  GTATTAGTCA
      ──────────────────────────────────── CMV promoter ────────────────────────────────────
 601  TCGCTATTAC  CATGGTGATG  CGGTTTTGGC  AGTACATCAA  TGGGCGTGGA  TAGCGGTTTG
      ──────────────────────────────────── CMV promoter ────────────────────────────────────
 661  ACTCACGGGG  ATTTCCAAGT  CTCCACCCCA  TTGACGTCAA  TGGGAGTTTG  TTTTGGCACC
                                                                ──── CMV forward primer ────
      ──────────────────────────────────── CMV promoter ────────────────────────────────────
 721  AAAATCAACG  GGACTTTCCA  AAATGTCGTA  ACAACTCCGC  CCCATTGACG  CAAATGGGCG
      ─ CMV forward prime ─
                                        ──────────── CMV promoter ────────────
 781  GTAGGCGTGT  ACGGTGGGAG  GTCTATATAA  GCAGAGCTCT  CTGGCTAACT  AGAGAACCCA
                                                   ──────── T7 primer ────────
              ─────── CMV promoter ───────
                                                   ──────── T7 promoter ───────
 841  CTGCTTACTG  GCTTATCGAA  ATTAATACGA  CTCACTATAG  GGAGACCCAA  GCTGGCTAGT
                        ── KpnI ──      ── BamHI ──             ────── Kir6.1 ──────
           ── HindIII ──              ── BstXI ──
  +2                                                  M  L  A  R  K  S  I  P  E·
 901  TAAGCTTGGT  ACCGAGCTCG  GATCCGCCAC  CATGCTGGCC  AGGAAGAGCA  TCATCCCGGA
                                           ──────────── Kir6.1 ────────────
  +2  ·E  E  Y  V  L  A  R  I  A  A  E  N  L  R  K  P  R  I  R  D  R·
 961  GGAGTATGTG  CTGGCCCGCA  TCGCGGCGGA  GAACCTGCGC  AAACCGCGCA  TCCGCGACCG
                                           ──────────── Kir6.1 ────────────
  +2  ·R  L  P  K  A  R  F  I  A  K  S  G  A  C  N  L  A  H  K  N  I·
1021  CCTCCCCAAA  GCCCGCTTCA  TCGCCAAGAG  CGGAGCCTGC  AACCTGGCTC  ACAAGAACAT
                                           ──────────── Kir6.1 ────────────
  +2  ·R  E  Q  G  R  F  L  Q  D  I  F  T  T  L  V  D  L  K  W  R·
1081  CCGAGAGCAA  GGTCGCTTCC  TGCAGGACAT  CTTCACCACC  TTGGTAGACC  TGAAGTGGCG
                                           ──────────── Kir6.1 ────────────
  +2  ·R  H  T  L  V  I  F  T  M  S  F  L  C  S  W  L  L  F  A  I  M·
1141  TCACACGCTG  GTCATCTTCA  CCATGTCCTT  CCTCTGCAGC  TGGCTGCTCT  TCGCTATCAT
                                           ──────────── Kir6.1 ────────────
  +2  ·M  W  W  L  V  A  F  A  H  G  D  I  Y  A  Y  M  E  K  G  I  T·
1201  GTGGTGGCTG  GTGGCCTTCG  CCCACGGGGA  CATCTATGCT  TACATGGAGA  AAGGCATCAC
```

Fig. 21-2

```
                                         Kir6.1
   +2   · T  E  K  S  G  L  E  S  A  V  C  V  T  N  V  R  S  F  T  S  A ·
  1261  GGAGAAGAGT GGCCTGGAGT CTGCCGTCTG TGTGACCAAT GTCAGGTCAT TCACTTCTGC
                                         Kir6.1
   +2   · A  F  L  F  S  I  E  V  Q  V  T  I  G  F  G  G  R  M  M  T  E ·
  1321  GTTTCTCTTC TCCATCGAGG TTCAAGTGAC CATTGGGTTT GGAGGCAGAA TGATGACTGA
                                         Kir6.1
   +2   · E  E  C  P  L  A  I  T  V  L  I  L  Q  N  I  V  G  L  I  I  N ·
  1381  GGAGTGCCCT CTGGCCATCA CGGTTTTGAT TCTGCAGAAC ATTGTGGGTC TGATCATCAA
                                         Kir6.1
   +2   · N  A  V  M  L  G  C  I  F  M  K  T  A  Q  A  H  R  R  A  E  T ·
  1441  CGCGGTCATG TTGGGCTGCA TCTTCATGAA GACGGCCCAG GCCCACAGAA GGGCAGAGAC
                                         Kir6.1
   +2   · T  L  I  F  S  R  H  A  V  I  A  V  R  N  G  K  L  C  F  M  F ·
  1501  GCTGATTTTC AGCCGCCATG CTGTAATTGC GGTCCGTAAT GGCAAGCTGT GCTTCATGTT
                                         Kir6.1
   +2   · F  R  V  G  D  L  R  K  S  M  I  I  S  A  S  V  R  I  Q  V  V ·
  1561  CCGGGTGGGT GACCTGAGGA AAAGCATGAT CATTAGCGCC TCGGTGCGCA TCCAGGTGGT
                                         Kir6.1
   +2   · V  K  K  T  T  T  P  E  G  E  V  V  P  I  H  Q  Q  D  I  P  V ·
  1621  CAAGAAAACC ACGACGCCAG AAGGAGAGGT GGTGCCTATT CACCAGCAGG ACATCCCTGT
                                         Kir6.1
   +2   · V  D  N  P  I  E  S  N  N  I  F  L  V  A  P  L  I  I  C  H  V ·
  1681  GGATAATCCC ATCGAGAGCA ATAACATCTT CCTAGTGGCC CCTTTGATCA TCTGCCATGT
                                         Kir6.1
   +2   · V  I  D  K  R  S  P  L  Y  D  I  S  A  T  D  L  V  N  Q  D  L ·
  1741  GATTGATAAG CGTAGCCCCC TGTACGATAT CTCAGCCACT GACCTTGTCA ACCAAGACCT
                                         Kir6.1
   +2   · L  E  V  I  V  I  L  E  G  V  V  E  T  T  G  I  T  T  Q  A  R ·
  1801  GGAGGTCATA GTGATTCTCG AGGGCGTGGT GGAAACCACG GGCATCACCA CGCAAGCGCG
                                         Kir6.1
   +2   · R  T  S  Y  I  A  E  E  I  Q  W  G  H  R  F  V  S  I  V  T  E ·
  1861  GACCTCCTAC ATTGCAGAGG AGATCCAGTG GGGACACCGC TTCGTGTCGA TTGTGACTGA
                                         Kir6.1
   +2   · E  E  E  G  V  Y  S  V  D  Y  S  K  F  G  N  T  V  R  V  A  A ·
  1921  GGAGGAGGGA GTGTACTCTG TGGACTATTC TAAATTTGGT AATACTGTGA GAGTGGCGGC
                                         Kir6.1
   +2   · A  P  R  C  S  A  R  E  L  D  E  K  P  S  I  L  I  Q  T  L  Q ·
  1981  GCCAAGATGC AGTGCCCGGG AGCTGGACGA GAAACCTTCC ATCTTGATTC AGACCCTCCA
                                         Kir6.1
   +2   · Q  K  S  E  L  S  H  Q  N  S  L  R  K  R  N  S  M  R  R  N  N ·
  2041  AAAGAGTGAA CTGTCGCACC AGAATTCTCT GAGGAAGCGC AACTCTATGA GAAGAAACAA
                                         Kir6.1
   +2   · N  S  M  R  R  S  N  S  I  R  R  N  N  S  S  L  M  V  P  K  V ·
  2101  CTCCATGAGG AGGAGCAACT CCATCCGGAG GAATAACTCT TCCCTCATGG TGCCCAAGGT
                                         Kir6.1                          NotI
   +2   · V  Q  F  M  T  P  E  G  N  Q  C  P  S  E  S  ·
  2161  GCAATTCATG ACTCCAGAAG GAAACCAGTG CCCATCAGAA TCATGATAGC GGCCGCTCGA
              ApaI
        XbaI        StuI                                              AgeI
  2221  GTCTAGAGGG CCCTTCGAAC AAAAACTCAT CTCAGAAGAG GATCTGAATA TGCATACCGG
```

Fig. 21-3

```
              AgeI                    PmeI                      BGH pA
      2281  TCATCATCAC CATCACCATT GAGTTTAAAC CCGCTGATCA GCCTCGACTG TGCCTTCTAG
                                                              BGH reverse primer
                                       BGH pA
      2341  TTGCCAGCCA TCTGTTGTTT GCCCCTCCCC CGTGCCTTCC TTGACCCTGG AAGGTGCCAC
                                       BGH pA
      2401  TCCCACTGTC CTTTCCTAAT AAAATGAGGA AATTGCATCG CATTGTCTGA GTAGGTGTCA
                                       BGH pA
      2461  TTCTATTCTG GGGGGTGGGG TGGGGCAGGA CAGCAAGGGG GAGGATTGGG AAGACAATAG
                   BGH pA
      2521  CAGGCATGCT GGGGATGCGG TGGGCTCTAT GGCTTCTGAG GCGGAAAGAA CCAGCTGGGG
                                       f1 origin
      2581  CTCTAGGGGG TATCCCCACG CGCCCTGTAG CGGCGCATTA AGCGCGGCGG GTGTGGTGGT
                                       f1 origin
      2641  TACGCGCAGC GTGACCGCTA CACTTGCCAG CGCCCTAGCG CCCGCTCCTT TCGCTTTCTT
                                       f1 origin
      2701  CCCTTCCTTT CTCGCCACGT TCGCCGGCTT TCCCCGTCAA GCTCTAAATC GGGGGCTCCC
                                       f1 origin
      2761  TTTAGGGTTC CGATTTAGTG CTTTACGGCA CCTCGACCCC AAAAAACTTG ATTAGGGTGA
                                       f1 origin
      2821  TGGTTCACGT AGTGGGCCAT CGCCCTGATA GACGGTTTTT CGCCCTTTGA CGTTGGAGTC
                                       f1 origin
      2881  CACGTTCTTT AATAGTGGAC TCTTGTTCCA AACTGGAACA ACACTCAACC CTATCTCGGT
                                       f1 origin
      2941  CTATTCTTTT GATTTATAAG GGATTTTGCC GATTTCGGCC TATTGGTTAA AAAATGAGCT
                           f1 origin
      3001  GATTTAACAA AAATTTAACG CGAATTAATT CTGTGGAATG TGTGTCAGTT AGGGTGTGGA
                                   SV40 early promoter
      3061  AAGTCCCCAG GCTCCCCAGC AGGCAGAAGT ATGCAAAGCA TGCATCTCAA TTAGTCAGCA
                                   SV40 early promoter
      3121  ACCAGGTGTG GAAAGTCCCC AGGCTCCCCA GCAGGCAGAA GTATGCAAAG CATGCATCTC
                                   SV40 early promoter
      3181  AATTAGTCAG CAACCATAGT CCCGCCCCTA ACTCCGCCCA TCCCGCCCCT AACTCCGCCC
                                   SV40 early promoter
      3241  AGTTCCGCCC ATTCTCCGCC CCATGGCTGA CTAATTTTTT TTATTTATGC AGAGGCCGAG
                                   SV40 early promoter
      3301  GCCGCCTCTG CCTCTGAGCT ATTCCAGAAG TAGTGAGGAG GCTTTTTTGG AGGCCTAGGC
                               SV40 early promoter
      3361  TTTTGCAAAA AGCTCCCGGG AGCTTGTATA TCCATTTTCG GATCTGATCA AGAGACAGGA
                                          Neo(R)
      3421  TGAGGATCGT TTCGCATGAT TGAACAAGAT GGATTGCACG CAGGTTCTCC GGCCGCTTGG
                                          Neo(R)
      3481  GTGGAGAGGC TATTCGGCTA TGACTGGGCA CAACAGACAA TCGGCTGCTC TGATGCCGCC
                                          Neo(R)
      3541  GTGTTCCGGC TGTCAGCGCA GGGGCGCCCG GTTCTTTTTG TCAAGACCGA CCTGTCCGGT
                                          Neo(R)
      3601  GCCCTGAATG AACTGCAGGA CGAGGCAGCG CGGCTATCGT GGCTGGCCAC GACGGGCGTT
                                          Neo(R)
      3661  CCTTGCGCAG CTGTGCTCGA CGTTGTCACT GAAGCGGGAA GGGACTGGCT GCTATTGGGC
```

Fig. 21-4

```
                                     Neo(R)
3721  GAAGTGCCGG GGCAGGATCT CCTGTCATCT CACCTTGCTC CTGCCGAGAA AGTATCCATC
                                     Neo(R)
3781  ATGGCTGATG CAATGCGGCG GCTGCATACG CTTGATCCGG CTACCTGCCC ATTCGACCAC
                                     Neo(R)
3841  CAAGCGAAAC ATCGCATCGA GCGAGCACGT ACTCGGATGG AAGCCGGTCT TGTCGATCAG
                                     Neo(R)
3901  GATGATCTGG ACGAAGAGCA TCAGGGGCTC GCGCCAGCCG AACTGTTCGC CAGGCTCAAG
                                     Neo(R)
3961  GCGCGCATGC CCGACGGCGA GGATCTCGTC GTGACCCATG GCGATGCCTG CTTGCCGAAT
                                     Neo(R)
4021  ATCATGGTGG AAAATGGCCG CTTTTCTGGA TTCATCGACT GTGGCCGGCT GGGTGTGGCG
                                     Neo(R)
4081  GACCGCTATC AGGACATAGC GTTGGCTACC CGTGATATTG CTGAAGAGCT TGGCGGCGAA
                                     Neo(R)
4141  TGGGCTGACC GCTTCCTCGT GCTTTACGGT ATCGCCGCTC CCGATTCGCA GCGCATCGCC
                                     Neo(R)
4201  TTCTATCGCC TTCTTGACGA GTTCTTCTGA GCGGGACTCT GGGGTTCGCG AAATGACCGA
4261  CCAAGCGACG CCCAACCTGC CATCACGAGA TTTCGATTCC ACCGCCGCCT TCTATGAAAG
4321  GTTGGGCTTC GGAATCGTTT TCCGGGACGC CGGCTGGATG ATCCTCCAGC GCGGGGATCT
                                               SV40 pA
4381  CATGCTGGAG TTCTTCGCCC ACCCCAACTT GTTTATTGCA GCTTATAATG GTTACAAATA
                                      SV40 pA
4441  AAGCAATAGC ATCACAAATT TCACAAATAA AGCATTTTTT TCACTGCATT CTAGTTGTGG
                       SV40 pA
4501  TTTGTCCAAA CTCATCAATG TATCTTATCA TGTCTGTATA CCGTCGACCT CTAGCTAGAG
4561  CTTGGCGTAA TCATGGTCAT AGCTGTTTCC TGTGTGAAAT TGTTATCCGC TCACAATTCC
4621  ACACAACATA CGAGCCGGAA GCATAAAGTG TAAAGCCTGG GGTGCCTAAT GAGTGAGCTA
4681  ACTCACATTA ATTGCGTTGC GCTCACTGCC CGCTTTCCAG TCGGGAAACC TGTCGTGCCA
4741  GCTGCATTAA TGAATCGGCC AACGCGCGGG GAGAGGCGGT TTGCGTATTG GGCGCTCTTC
4801  CGCTTCCTCG CTCACTGACT CGCTGCGCTC GGTCGTTCGG CTGCGGCGAG CGGTATCAGC
4861  TCACTCAAAG GCGGTAATAC GGTTATCCAC AGAATCAGGG GATAACGCAG GAAAGAACAT
                                                                  pUC origin
4921  GTGAGCAAAA GGCCAGCAAA AGGCCAGGAA CCGTAAAAAG GCCGCGTTGC TGGCGTTTTT
                                     pUC origin
4981  CCATAGGCTC CGCCCCCCTG ACGAGCATCA CAAAAATCGA CGCTCAAGTC AGAGGTGGCG
                                     pUC origin
5041  AAACCCGACA GGACTATAAA GATACCAGGC GTTTCCCCCT GGAAGCTCCC TCGTGCGCTC
                                     pUC origin
5101  TCCTGTTCCG ACCCTGCCGC TTACCGGATA CCTGTCCGCC TTTCTCCCTT CGGGAAGCGT
                                     pUC origin
5161  GGCGCTTTCT CATAGCTCAC GCTGTAGGTA TCTCAGTTCG GTGTAGGTCG TTCGCTCCAA
                                     pUC origin
5221  GCTGGGCTGT GTGCACGAAC CCCCCGTTCA GCCCGACCGC TGCGCCTTAT CCGGTAACTA
                                     pUC origin
5281  TCGTCTTGAG TCCAACCCGG TAAGACACGA CTTATCGCCA CTGGCAGCAG CCACTGGTAA
                                     pUC origin
5341  CAGGATTAGC AGAGCGAGGT ATGTAGGCGG TGCTACAGAG TTCTTGAAGT GGTGGCCTAA
                                     pUC origin
```

Fig. 21-5

```
5401  CTACGGCTAC ACTAGAAGAA CAGTATTTGG TATCTGCGCT CTGCTGAAGC CAGTTACCTT
                                      pUC origin
5461  CGGAAAAAGA GTTGGTAGCT CTTGATCCGG CAAACAAACC ACCGCTGGTA GCGGTGGTTT
                                      pUC origin
5521  TTTTGTTTGC AAGCAGCAGA TTACGCGCAG AAAAAAAGGA TCTCAAGAAG ATCCTTTGAT
                                      pUC origin
5581  CTTTTCTACG GGGTCTGACG CTCAGTGGAA CGAAAACTCA CGTTAAGGGA TTTTGGTCAT
        pUC origin
5641  GAGATTATCA AAAAGGATCT TCACCTAGAT CCTTTTAAAT TAAAAATGAA GTTTTAAATC
5701  AATCTAAAGT ATATATGAGT AAACTTGGTC TGACAGTTAC CAATGCTTAA TCAGTGAGGC
                                                            Amp(R)
5761  ACCTATCTCA GCGATCTGTC TATTTCGTTC ATCCATAGTT GCCTGACTCC CCGTCGTGTA
                                      Amp(R)
5821  GATAACTACG ATACGGGAGG GCTTACCATC TGGCCCCAGT GCTGCAATGA TACCGCGAGA
                                      Amp(R)
5881  CCCACGCTCA CCGGCTCCAG ATTTATCAGC AATAAACCAG CCAGCCGGAA GGGCCGAGCG
                                      Amp(R)
5941  CAGAAGTGGT CCTGCAACTT TATCCGCCTC CATCCAGTCT ATTAATTGTT GCCGGGAAGC
                                      Amp(R)
6001  TAGAGTAAGT AGTTCGCCAG TTAATAGTTT GCGCAACGTT GTTGCCATTG CTACAGGCAT
                                      Amp(R)
6061  CGTGGTGTCA CGCTCGTCGT TTGGTATGGC TTCATTCAGC TCCGGTTCCC AACGATCAAG
                                      Amp(R)
6121  GCGAGTTACA TGATCCCCCA TGTTGTGCAA AAAAGCGGTT AGCTCCTTCG GTCCTCCGAT
                                      Amp(R)
6181  CGTTGTCAGA AGTAAGTTGG CCGCAGTGTT ATCACTCATG GTTATGGCAG CACTGCATAA
                                      Amp(R)
6241  TTCTCTTACT GTCATGCCAT CCGTAAGATG CTTTTCTGTG ACTGGTGAGT ACTCAACCAA
                                      Amp(R)
6301  GTCATTCTGA GAATAGTGTA TGCGGCGACC GAGTTGCTCT TGCCCGGCGT CAATACGGGA
                                      Amp(R)
6361  TAATACCGCG CCACATAGCA GAACTTTAAA AGTGCTCATC ATTGGAAAAC GTTCTTCGGG
                                      Amp(R)
6421  GCGAAAACTC TCAAGGATCT TACCGCTGTT GAGATCCAGT TCGATGTAAC CCACTCGTGC
                                      Amp(R)
6481  ACCCAACTGA TCTTCAGCAT CTTTTACTTT CACCAGCGTT TCTGGGTGAG CAAAAACAGG
                                      Amp(R)
6541  AAGGCAAAAT GCCGCAAAAA AGGGAATAAG GGCGACACGG AAATGTTGAA TACTCATACT
                                                                bla promoter
                                      Amp(R)
6601  CTTCCTTTTT CAATATTATT GAAGCATTTA TCAGGGTTAT TGTCTCATGA GCGGATACAT
                                      bla promoter
6661  ATTTGAATGT ATTTAGAAAA ATAAACAAAT AGGGGTTCCG CGCACATTTC CCCGAAAAGT
                                      bla promoter
6721  GCCACCTGAC GTC
```

ADAMANTANE DERIVATIVE AND USE THEREOF

CROSS-REFERENCE TO RELATED APPLICATIONS

This application is the U.S. National Stage of PCT/JP2017/002760, filed Jan. 26, 2017, which claims priority to JP 2016-012392, filed Jan. 26, 2016.

The instant application contains a Sequence Listing which has been submitted in ASCII format via EFS-WEB and is hereby incorporated by reference in its entirety. Said ASCII copy, created on Jul. 24, 2018, is named sequence.txt and is 18 KB.

TECHNICAL FIELD

The present invention relates to an adamantane derivative and a pharmaceutically acceptable salt thereof. The present invention further relates to a pharmaceutical composition containing the compound and a method of treating or preventing a disease by using the compound.

BACKGROUND ART

ATP-sensitive K$^+$ channel (K$_{ATP}$ channel) is an inwardly rectifying K$^+$ channel connecting intracellular metabolism and cell-membrane excitation and known to have a heterologous octamer structure constituted of a sulfonyl urea receptor (SUR) belonging to an ABC protein family and two-span transmembrane subunits Kir6.1 and Kir6.2. The activity of the K$_{ATP}$ channel is controlled by various types of K$^+$ channel openers, inhibitors or intracellular nucleotides. All of these have active sites in SUR subunits. It has been reported that the reactions of them differ depending on the subtype of SUR (NPL 1).

Some of adamantane derivatives having a cage type structure are used as medical drugs. Amantadine is used as antiviral drug and a therapeutic agent for Parkinson's disease. Memantine hydrochloride has been approved as a therapeutic agent for moderate/severe Alzheimer's dementia even in Japan. Memantine is a noncompetitive NMDA-receptor inhibitor and reported to have an action mechanism which prevents neuronal cell death of excessive glutamic acid release caused by ischemia (NPL 2).

Adamantane derivatives having an activity as a medical drug are reported in several literatures (PTLs 1 to 3).

CITATION LIST

Patent Literature

PTL 1: National Publication of International Patent Application No. 2011-529057
PTL 2: Japanese Patent Laid-Open No. 2010-522203
PTL 3: National Publication of International Patent Application No. 2009-508956

Non Patent Literature

NPL 1: Folia pharmacologica *Japonica*, 126, 311 to 316 (2005)

NPL 2: Folia pharmacologica *Japonica*, 124, 145 to 151 (2004)

SUMMARY OF INVENTION

Technical Problem

A therapeutic and prophylactic method exerting a sufficient effect on a cognitive disease or disorder such as Alzheimer's disease has not yet been established, and thus, development of a novel therapeutic and prophylactic agent different in action mechanism from existing medicinal agents has been desired. In addition, development of a novel therapeutic and prophylactic agent for diabetes has been strongly desired.

In one aspect, an object of the present invention is to provide a pharmaceutical composition for use in treating or preventing a cognitive disease or disorder. Another object of the present invention is to provide a method of treating or preventing a cognitive disease or disorder by using a predetermined adamantane derivative.

In one aspect, an object of the present invention is to provide a pharmaceutical composition for use in treating or preventing diabetes or a diabetic complication. Another object of the present invention is to provide a method of treating or preventing diabetes or a diabetic complication by using a predetermined adamantane derivative.

ATP-sensitive K$^+$ channel (K$_{ATP}$ channel) contains subunits Kir6.1 and Kir6.2 and is known to serve as an active site of e.g., an anti-diabetic drug.

In one aspect, an object of the present invention is to provide a channel inhibitor against Kir6.1 or a channel inhibitor against Kir6.2 of the K$_{ATP}$ channel. Another object of the present invention is to provide a pharmaceutical composition for use in treating or preventing a disease involving Kir6.1 channel or Kir6.2 channel of the K$_{ATP}$ channel. Another object of the present invention is to provide a method of treating or preventing a disease involving Kir6.1 channel or Kir6.2 channel of the K$_{ATP}$ channel, by using a predetermined adamantane derivative.

Solution to Problem

The present inventors conducted intensive studies with a view to attaining the aforementioned objects. As a result, they found that an adamantane derivative has a Kir6.2 channel inhibitory activity, a Kir6.1 channel inhibitory activity, a therapeutic effect for a cognitive disease or disorder and a hypoglycemic effect. Based on the finding, the present invention was accomplished. In the specification, the following inventions set forth in [1-1] to [1-20] are disclosed.

[1-1] A compound represented by Formula (I):

[Chemical Formula 1]

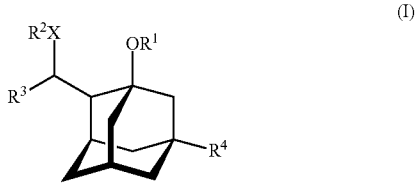

wherein R$^1$ represents a hydrogen atom or (C$_{1-6}$ alkyl) carbonyl optionally substituted with one or more halogen atoms;

$R^2$ represents a hydrogen atom or ($C_{1-6}$ alkyl)carbonyl optionally substituted with one or more halogen atoms;

X represents O or $NR^5$;

$R^3$ represents phenyl optionally substituted with one or more substituents selected from $X^1$, 5- or 6-membered heteroaryl optionally substituted with one or more substituents selected from $X^1$, or $COOR^6$;

$R^4$ represents a hydrogen atom, a halogen atom, azido, $—OR^7$ or $—NHR^8$;

$R^5$ represents a hydrogen atom or $C_{1-6}$ alkyl;

$R^6$ represents a hydrogen atom or $C_{1-6}$ alkyl;

$R^7$ represents a hydrogen atom, $C_{1-6}$ alkyl, $C_{1-6}$ alkoxy-$C_{1-6}$ alkyl or ($C_{1-6}$ alkyl)carbonyl optionally substituted with one or more halogen atoms;

$R^8$ represents a hydrogen atom, $C_{1-6}$ alkyl or ($C_{1-6}$ alkyl)carbonyl optionally substituted with one or more halogen atoms; and $X^1$ represents $C_{1-6}$ alkyl, a halogen atom, $C_{1-6}$ alkoxy, nitro or cyano, an enantiomer thereof, a diastereomer thereof, or a pharmaceutically acceptable salt thereof.

[1-2] The compound, an enantiomer thereof, a diastereomer thereof, or a pharmaceutically acceptable salt thereof according to [1-1], wherein $R^4$ represents a chlorine atom or azido.

[1-3] The compound, an enantiomer thereof, a diastereomer thereof, or a pharmaceutically acceptable salt thereof according to [1-1] or [1-2], wherein $R^1$ represents trifluoroacetyl.

[1-4] The compound, an enantiomer thereof, a diastereomer thereof, or a pharmaceutically acceptable salt thereof according to any one of [1-1] to [1-3], wherein $R^2$ represents ($C_{1-6}$ alkyl)carbonyl optionally substituted with one or more halogen atoms.

[1-5] The compound, an enantiomer thereof, a diastereomer thereof, or a pharmaceutically acceptable salt thereof according to [1-4], wherein $R^2$ represents trifluoroacetyl.

[1-6] The compound, an enantiomer thereof, a diastereomer thereof, or a pharmaceutically acceptable salt thereof according to any one of [1-1] to [1-5], wherein $R^3$ represents phenyl optionally substituted with one or more substituents selected from $X^1$ or pyridyl optionally substituted with one or more substituents selected from $X^1$.

[1-7] The compound, an enantiomer thereof, a diastereomer thereof, or a pharmaceutically acceptable salt thereof according to [1-1], selected from (R)-((1R,2S,3R,5R,7S)-5-azido-1-hydroxyadamantan-2-yl)(phenyl)methyl acetate;

ethyl (S)-2-acetamido-2-((1R,2S,3R,5R,7R)-5-chloro-1-hydroxyadamantan-2-yl)acetate;

ethyl (R)-2-acetamido-2-((1R,2S,3R,5R,7R)-5-chloro-1-hydroxyadamantan-2-yl)acetate;

(1R,2S,3R,5R,7R)-5-chloro-2-((S)-2-methoxy-2-oxo-1-(2,2,2-trifluoroacetamido)ethyl)adamantan-1-yl 2,2,2-trifluoroacetate;

(1S,2R,3S,5S,7S)-5-chloro-2-((R)-phenyl(2,2,2-trifluoroacetamido)methyl)adamantan-1-yl 2,2,2-trifluoroacetate;

(S)-2-amino-2-((1R,2S,3R,5R,7S)-1,5-dihydroxyadamantan-2-yl)acetic acid;

N—((R)-((1S,2R,3S,5S,7S)-5-chloro-1-hydroxyadamantan-2-yl)(phenyl)methyl)-2,2,2-trifluoroacetamide;

(1S,2R,3S,5R,7S)-2-((R)-phenyl(2,2,2-trifluoroacetamido)methyl)adamantan-1-yl 2,2,2-trifluoroacetate;

(1S,2R,3S,5S,7R)-5-(2-methoxyethoxy)-2-((R)-phenyl(2,2,2-trifluoroacetamido)methyl)adamantan-1-yl 2,2,2-trifluoroacetate;

N—((R)-((1S,2R,3S,5S,7S)-5-chloro-1-hydroxyadamantan-2-yl)(pyridin-3-yl)methyl)-2,2,2-trifluoroacetamide;

2,2,2-trifluoro-N—((R)-((1S,2R,3S,5R,7S)-1-hydroxyadamantan-2-yl)(phenyl)methyl)acetamide; and (1S,2R,3S,5S,7R)-5-methoxy-2-((R)-phenyl(2,2,2-trifluoroacetamido)methyl)adamantan-1-yl 2,2,2-trifluoroacetate, or an enantiomer thereof, a diastereomer thereof, or a pharmaceutically acceptable salt thereof.

[1-8] A pharmaceutical composition containing the compound, an enantiomer thereof, a diastereomer thereof, or a pharmaceutically acceptable salt thereof according to any one of [1-1] to [1-7].

[1-9] The pharmaceutical composition according to [1-8], for use in treating or preventing a cognitive disease or disorder.

[1-10] The pharmaceutical composition according to [1-9], wherein the cognitive disease or disorder is selected from Alzheimer's dementia, cerebrovascular dementia, Lewy body dementia, frontotemporal dementia, Parkinson's disease, a mental disease and a neurodegenerative disease.

[1-11] The pharmaceutical composition according to [1-8] for use in treating or preventing diabetes or a diabetic complication.

[1-12] A Kir6.2 channel inhibitor containing the compound, an enantiomer thereof, a diastereomer thereof, or a pharmaceutically acceptable salt thereof according to any one of [1-1] to [1-7].

[1-13] The Kir6.1 channel inhibitor containing the compound, an enantiomer thereof, a diastereomer thereof, or a pharmaceutically acceptable salt thereof according to any one of [1-1] to [1-7].

[1-14] A method of treating or preventing a cognitive disease or disorder, comprising administering a therapeutically effective amount of the compound, an enantiomer thereof, a diastereomer thereof, or a pharmaceutically acceptable salt thereof according to any one of [1-1] to [1-7] to a subject.

[1-15] The method according to [1-14], wherein the cognitive disease or disorder is selected from Alzheimer's dementia, cerebrovascular dementia, Lewy body dementia, frontotemporal dementia, Parkinson's disease, a mental disease and a neurodegenerative disease.

[1-16] The method of treating or preventing diabetes or a diabetic complication, comprising administering a therapeutically effective amount of the compound, an enantiomer thereof, a diastereomer thereof, or a pharmaceutically acceptable salt thereof according to any one of [1-1] to [1-7] to a subject.

[1-17] A method of treating or preventing a disease involving Kir6.1 channel or Kir6.2 channel, comprising administering a therapeutically effective amount of the compound, an enantiomer thereof, a diastereomer thereof, or a pharmaceutically acceptable salt thereof according to any one of [1-1] to [1-7] to a subject as a Kir6.1 channel inhibitor or a Kir6.2 channel inhibitor.

[1-18] The method according to [1-17], wherein the disease involving Kir6.1 channel or Kir6.2 channel is a cognitive disease or disorder, or diabetes or a diabetic complication.

[1-19] The method according to [1-17] or [1-18], wherein the disease involving Kir6.1 channel or Kir6.2 channel is a cognitive disease or disorder selected from Alzheimer's dementia, cerebrovascular dementia, Lewy body dementia, frontotemporal dementia, Parkinson's disease, a mental disease and a neurodegenerative disease.

[1-20] The method according to [1-17] or [1-18], wherein the disease involving Kir6.1 channel or Kir6.2 channel is diabetes or a diabetic complication.

In the specification, the following inventions set forth in [2-1] to [2-12] are disclosed.

[2-1] A compound represented by Formula (I):

[Chemical Formula 2]

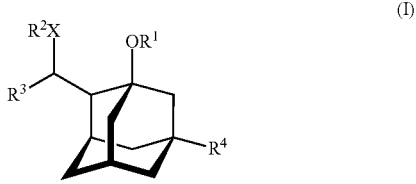

wherein R¹ represents a hydrogen atom or ($C_{1-6}$ alkyl)carbonyl optionally substituted with one or more halogen atoms;

R² represents a hydrogen atom or ($C_{1-6}$ alkyl)carbonyl optionally substituted with one or more halogen atoms;

X represents O or $NR^5$;

R³ represents phenyl optionally substituted with one or more substituents selected from $X^1$, or $COOR^6$;

R⁴ represents a hydrogen atom, a halogen atom, azido, —OR⁷ or —NHR⁸;

R⁵ represents a hydrogen atom or $C_{1-6}$ alkyl;

R⁶ represents a hydrogen atom or $C_{1-6}$ alkyl;

R⁷ represents a hydrogen atom, $C_{1-6}$ alkyl or ($C_{1-6}$ alkyl)carbonyl optionally substituted with one or more halogen atoms;

R⁸ represents a hydrogen atom, $C_{1-6}$ alkyl or ($C_{1-6}$ alkyl)carbonyl optionally substituted with one or more halogen atoms; and $X^1$ represents $C_{1-6}$ alkyl, a halogen atom, $C_{1-6}$ alkoxy, nitro or cyano, an enantiomer thereof, a diastereomer thereof, or a pharmaceutically acceptable salt thereof.

[2-2] The compound, an enantiomer thereof, a diastereomer thereof, or a pharmaceutically acceptable salt thereof according to [2-1], wherein R⁴ represents a chlorine atom or azido.

[2-3] The compound, an enantiomer thereof, a diastereomer thereof, or a pharmaceutically acceptable salt thereof according to [2-1] or [2-2], wherein R¹ represents trifluoroacetyl.

[2-4] The compound, an enantiomer thereof, a diastereomer thereof, or a pharmaceutically acceptable salt thereof according to any one of [2-1] to [2-3], wherein R² represents trifluoroacetyl.

[2-5] The compound, an enantiomer thereof, a diastereomer thereof, or a pharmaceutically acceptable salt thereof according to any one of [2-1] to [2-4], wherein R³ represents phenyl optionally substituted with one or more substituents selected from $X^1$.

[2-6] The compound, an enantiomer thereof, a diastereomer thereof, or a pharmaceutically acceptable salt thereof according to [2-1], selected from (R)-((1R,2S,3R,5R,7 S)-5-azido-1-hydroxyadamantan-2-yl)(phenyl)methyl acetate;

ethyl (S)-2-acetamido-2-((1R,2S,3R,5R,7R)-5-chloro-1-hydroxyadamantan-2-yl)acetate;

ethyl (R)-2-acetamido-2-((1R,2S,3R,5R,7R)-5-chloro-1-hydroxyadamantan-2-yl)acetate;

(1R,2S,3R,5R,7R)-5-chloro-2-((S)-2-methoxy-2-oxo-1-(2,2,2-trifluoroacetamido)ethyl)adamantan-1-yl 2,2,2-trifluoroacetate;

(1S,2R,3S,5S,7S)-5-chloro-2-((R)-phenyl(2,2,2-trifluoroacetamido)methyl)adamantan-1-yl 2,2,2-trifluoroacetate; and (S)-2-amino-2-((1R,2S,3R,5R,7S)-1,5-dihydroxyadamantan-2-yl)acetic acid, or an enantiomer thereof, a diastereomer thereof, or a pharmaceutically acceptable salt thereof.

[2-7] A pharmaceutical composition containing the compound, an enantiomer thereof, a diastereomer thereof, or a pharmaceutically acceptable salt thereof according to any one of [2-1] to [2-6].

[2-8] The pharmaceutical composition according to [2-7], for use in treating or preventing a cognitive disease or disorder.

[2-9] The pharmaceutical composition according to [2-8], wherein the cognitive disease or disorder is selected from Alzheimer's dementia, cerebrovascular dementia, Lewy body dementia, frontotemporal dementia, Parkinson's disease, a mental disease and a neurodegenerative disease.

[2-10] The pharmaceutical composition according to [2-7] for use in treating or preventing diabetes or a diabetic complication.

[2-11] A Kir6.2 channel inhibitor containing the compound, an enantiomer thereof, a diastereomer thereof, or a pharmaceutically acceptable salt thereof according to any one of [2-1] to [2-6].

[2-12] The Kir6.1 channel inhibitor containing the compound, an enantiomer thereof, a diastereomer thereof, or a pharmaceutically acceptable salt thereof according to any one of [2-1] to [2-6].

Advantageous Effects of Invention

In one aspect, the present invention provides a pharmaceutical composition for use in treating or preventing a cognitive disease or disorder. In another aspect, the present invention provides an inhibitor of Kir6.1 channel or Kir6.2 channel of $K_{AT}P$ channel.

BRIEF DESCRIPTION OF DRAWINGS

FIG. 2a shows (the results of) expression of Kir6.2 channel in N2A cells, which is checked by applying immunoblotting using an anti-Kir6.2 channel antibody to Kir6.2 channel-overexpressing cells. The case having a significant difference with a non-drug treatment group (−) is indicated by **.

FIG. 2b shows the assay results by a whole-cell patch-clamp method, showing that TP-014 suppresses outward potassium current in Kir6.2 channel-overexpressing cells. The results show that TP-014 inhibits Kir6.2 channel and attenuates potassium current.

FIG. 17-1 shows the sequence of a plasmid vector: pcDNA3.1-Kir6.2.

FIG. 17-2 shows the sequence of plasmid vector: pcDNA3.1-Kir6.2.

FIG. 17-3 shows the sequence of plasmid vector: pcDNA3.1-Kir6.2.

FIG. 17-4 shows the sequence of plasmid vector: pcDNA3.1-Kir6.2.

FIG. 17-5 shows the sequence of plasmid vector: pcDNA3.1-Kir6.2.

FIG. 21-1 shows the sequence of a plasmid vector: pcDNA3.1-Kir6.1.

FIG. 21-2 shows the sequence of a plasmid vector: pcDNA3.1-Kir6.1.

FIG. 21-3 shows the sequence of a plasmid vector: pcDNA3.1-Kir6.1.

FIG. 21-4 shows the sequence of a plasmid vector: pcDNA3.1-Kir6.1.

FIG. 21-5 shows the sequence of a plasmid vector: pcDNA3.1-Kir6.1.

DESCRIPTION OF EMBODIMENTS

Figure 1:
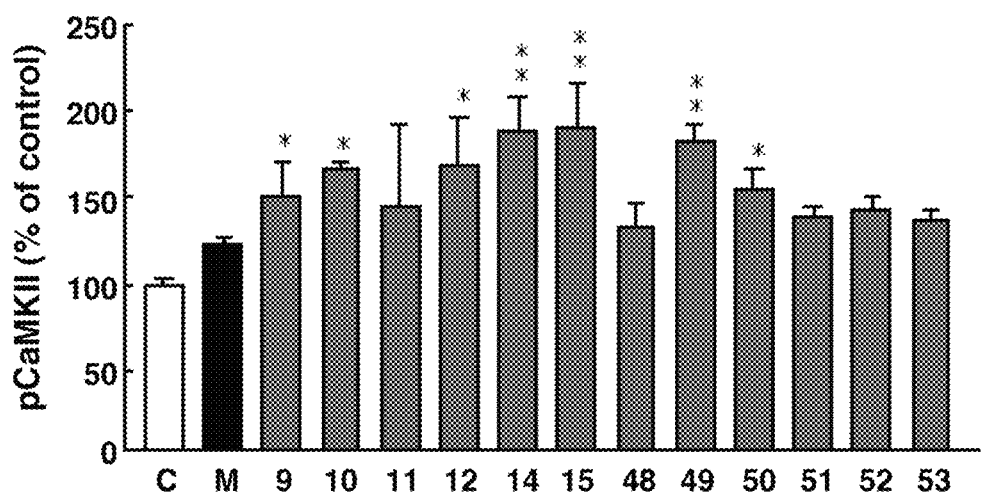
FIG. 1 is a graph showing CaMKII activity enhanced by the compound of the present invention in cells (Neuro2A cells) overexpressing Kir6.2 channel. All indications regarding significant difference is relative to a control (C: Kir6.2 expressing cells not treated with a drug) are marked. In the drawings of this application, the significant difference indicated by ** or ++ means P<0.01; or significant difference indicated by + or * means P<0.05.

Now, the present invention will be more specifically described below.

According to one aspect of the present invention, there is provided a pharmaceutical composition for treating or preventing a cognitive disease or disorder, containing a compound represented by Formula (I), an enantiomer thereof, a diastereomer thereof, or a pharmaceutically acceptable salt thereof. More specifically, the compound of the present invention includes the compound represented by the following Formulas (I) and (II).

[Chemical Formula 3]

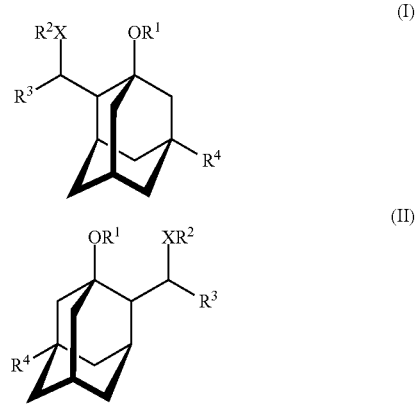

In the specification, "$C_{1-6}$ alkyl" refers to a linear, branched, cyclic or partial cyclic alkyl group having 1 to 6 carbon atoms. Examples thereof include methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl and 2-ethylbutyl, cyclopropyl, cyclobutyl, cyclopentyl, cyclohexyl and cyclopropylmethyl. For example, $C_{1-4}$ alkyl and $C_{1-3}$ alkyl are also included.

In the specification, "$C_{1-6}$ alkoxy" refers to an alkyloxy group [—O—($C_{1-6}$ alkyl)] having an alkyl group having 1 to 6 carbon atoms already defined. Examples thereof include methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, cyclopentyloxy, cyclohexyloxy and cyclopropylmethyloxy. For example, $C_{1-4}$ alkoxy and $C_{1-3}$ alkoxy are also included. In the specification, "$C_{1-4}$ alkoxy" include, for example, $C_{1-3}$ alkoxy.

In the specification, "azido" refers to —$N_3$.

In the specification, "($C_{1-6}$ alkyl)carbonyl" refers to an alkylcarbonyl group having a $C_{1-6}$ alkyl group already defined. Examples thereof include methylcarbonyl(acetyl), ethylcarbonyl, tert-butylcarbonyl and ($C_{1-3}$ alkyl)carbonyl.

In the specification, "5- or 6-membered heteroaryl" is not particularly limited as long as it is a heteroaryl of a 5-membered ring or a 6-membered ring having at least one hetero atom selected from an oxygen atom, a nitrogen atom and a sulfur atom. Examples thereof include pyridyl, pyrimidyl, pyridazinyl, pyrazyl, furanyl (furyl), thiophenyl (thienyl), oxazolyl, oxadiazolyl, pyrrolyl, imidazolyl, pyrazolyl, triazolyl and tetrazolyl.

In the specification, "$C_{1-6}$ alkoxy-$C_{1-6}$ alkyl" refers to $C_{1-6}$ alkyl having a substituent of $C_{1-6}$ alkoxy already defined and the alkyl moiety of $C_{1-6}$ alkyl is the same as already defined. Examples thereof include methoxymethyl, ethoxymethyl, 2-methoxyethyl, 1-methoxyethyl, 3-methoxypropyl, 2-methoxypropyl and 1-methoxypropyl.

Examples of a halogen atom include a fluorine atom, a chlorine atom, a bromine atom and an iodine atom.

In the specification, examples of "($C_{1-6}$ alkyl)carbonyl optionally substituted with one or more halogen atoms" include trifluoroacetyl, difluoroacetyl, 2,2,2-trifluoroethylcarbonyl and perfluoroethylcarbonyl.

If the compound represented by Formula (I) forms a solvate such as a hydrate, the present invention can be carried out by use of the solvate. Furthermore, the compound of the present invention can be appropriately carried out by use of the compound in the state of a mixture or a solution or crystal polymorphism.

In the specification, "substituted with one or more substituents" includes, for example, substitution with 1 to 3 substituents.

The present invention relating to the compound represented by Formula (I) includes a tautomer, a geometric isomer, various stereoisomers such as an optical isomer, and a diastereomer and a mixture of these. Examples of the compound represented by Formula (I) contains compound represented by the following Formulas (Ia) to (Ih).

[Chemical Formula 4]

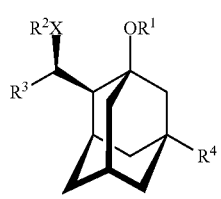
(Ia)

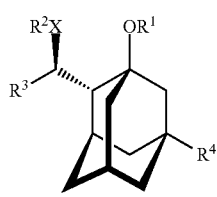
(Ib)

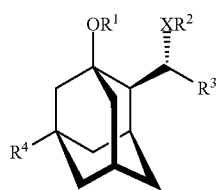
(Ic)

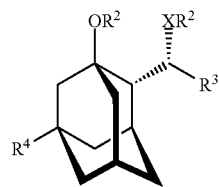
(Id)

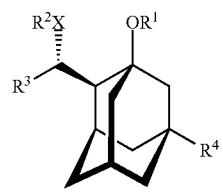
(Ie)

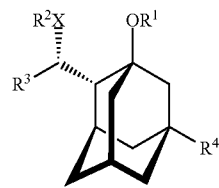
(If)

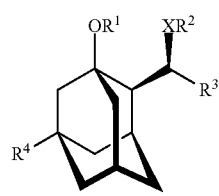
(Ig)

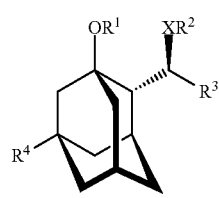
(Ih)

As the compound of the present invention, for example, a compound described in Examples of the specification can be used. More specifically, the following compounds can be used:

(R)-((1R,2S,3R,5R,7S)-5-azido-1-hydroxyadamantan-2-yl)(phenyl)methyl acetate (TP-009);

ethyl (S)-2-acetamido-2-((1R,2S,3R,5R,7R)-5-chloro-1-hydroxyadamantan-2-yl)acetate (TP-010);

ethyl (R)-2-acetamido-2-((1R,2S,3R,5R,7R)-5-chloro-1-hydroxyadamantan-2-yl)acetate (TP-011);

(1R,2S,3R,5R,7R)-5-chloro-2-((S)-2-methoxy-2-oxo-1-(2,2,2-trifluoroacetamido)ethyl)adamantan-1-yl 2,2,2-trifluoroacetate (TP-012);

(1S,2R,3S,5S,7S)-5-chloro-2-((R)-phenyl(2,2,2-trifluoroacetamido)methyl)adamantan-1-yl 2,2,2-trifluoroacetate (TP-014);

(S)-2-amino-2-((1R,2S,3R,5R,7S)-1,5-dihydroxyadamantan-2-yl)acetic acid (TP-015);

N—((R)-((1S,2R,3S,5S,7S)-5-chloro-1-hydroxyadamantan-2-yl)(phenyl)methyl)-2,2,2-trifluoroacetamide (TP-048);

(1S,2R,3S,5R,7S)-2-((R)-phenyl(2,2,2-trifluoroacetamido)methyl)adamantan-1-yl 2,2,2-trifluoroacetate (TP-049);

(1S,2R,3S,5S,7R)-5-(2-methoxyethoxy)-2-((R)-phenyl(2,2,2-trifluoroacetamido)methyl)adamantan-1-yl 2,2,2-trifluoroacetate (TP-050);

N—((R)-((1S,2R,3S,5S,7S)-5-chloro-1-hydroxyadamantan-2-yl)(pyridin-3-yl)methyl)-2,2,2-trifluoroacetamide (TP-051);

2,2,2-trifluoro-N—((R)—((S,2R,3S,5R,7S)-1-hydroxyadamantan-2-yl)(phenyl)methyl) acetamide (TP-052); and (1S,2R,3S,5S,7R)-5-methoxy-2-((R)-phenyl(2,2,2-trifluoroacetamido)methyl)adamantan-1-yl 2,2,2-trifluoroacetate (TP-053).

The "pharmaceutically acceptable salt" of the compound represented by Formula (I) is not particularly limited as long as it is a salt that can be used as a pharmaceutical product. Examples of the salt formed by the compound of the present invention and a base include a salt with an inorganic base such as sodium, potassium, magnesium, calcium and aluminum; and a salt with an organic base such as methylamine, ethylamine and ethanolamine. The salt may be an acid addition salt. Examples of the acid addition salt include a salt with a mineral acid such as hydrochloric acid, hydrobromic acid, hydriodic acid, sulfuric acid, nitric acid and phosphoric acid; and an acid addition salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid and ethanesulfonic acid.

The atoms (for example, a hydrogen atom, a carbon atom, an oxygen atom, a nitrogen atom and a sulfur atom) contained in the compound represented by Formula (I) may be isotope atoms other than those naturally most frequently exist. The isotope atoms may be radioactive isotope atoms. More specifically, according to one aspect of the present invention, there is provided a compound represented by Formula (I) already defined in the specification and labeled with an isotope atom or a salt thereof. Labelling with an isotope atom herein may be labelling with, for example, a radioactive isotope (e.g., $^3H$, $^{14}C$, $^{32}P$). In order to easily prepare the compound, labeling with $^3H$ is preferable.

In an embodiment of the present invention, the compound represented by Formula (I), an enantiomer thereof, a diastereomer thereof, or a pharmaceutically acceptable salt thereof is administered as a prodrug and converted into an active compound in vivo.

In the present invention, examples of the treatment for a cognitive disease or disorder include treatment for Alzheimer's dementia, cerebrovascular dementia, Lewy body dementia, frontotemporal dementia, Parkinson's disease, a mental disease and a neurodegenerative disease. In the present invention, a pharmaceutical composition may be applied to improvement of brain dysfunctions for example, brain dysfunctions caused by cerebral vascular disease, brain injury, brain tumor, viral encephalitis, hypoxic encephalopathy and alcoholic intoxication. The present invention can be applied to, particularly, cognitive dysfunctions such as memory disturbance, attentional deficit, executive function disorder and social behavior disorder. Examples of the cognitive dysfunction include a neurodegenerative disease (Alzheimer's disease, Parkinson's disease, Pick's disease and Huntington's disease, etc.), a mental disease (schizophrenia, bipolar disorder, depression, phobia, sleep disorder, drug addiction, etc.) and a pervasive developmental disorder (autism, Asperger's syndrome, mental retardation, hyperactivity disorder, tic disorder, etc.).

In the present invention, examples of the diabetic complication include hyperglycemia, diabetic coma, ketonic coma, nonketotic hyperosmolar coma, lactic acidosis, hypoglycemic coma, acute infection, microangiopathy, diabetic retinopathy, diabetic nephropathy, diabetic neuropathy, macroangiopathy, cerebral vascular disease, ischemic heart disease, diabetic gangrene, hyperlipidemia, chronic infection, cholelithiasis and cataract.

In an embodiment of the present invention, the compound represented by Formula (I), an enantiomer thereof, a diastereomer thereof, or a pharmaceutically acceptable salt thereof is used as a Kir6.2 channel inhibitor or a Kir6.1 channel inhibitor. More specifically, the compound represented by Formula (I), an enantiomer thereof, a diastereomer thereof, or a pharmaceutically acceptable salt thereof can be used for treating or preventing a disease to which the Kir6.2 channel is involved, such as a cognitive disease or disorder, hyperglycemia, diabetes and a diabetic complication; and for treating or preventing a disease to which the Kir6.1 channel is involved, such as a cognitive disease or disorder, hyperglycemia, diabetes, a diabetic complication and a mental disease.

The pharmaceutical composition of the present invention may have various dosage forms. Examples of dosage forms for oral administration include a tablet, a capsule, a powder medicine, a granule, a pill, a liquid medicine, an emulsion, a suspension, a solution, a sprit, a syrup, an extract and an elixir. Examples of dosage forms for parenteral administration include an injection such as a subcutaneous injection, an intravenous injection, an intramuscular injection, an intraperitoneal injection; transdermal administration or patch, and an ointment or a lotion. Examples of dosage forms for intraoral administration include a sublingual formulation and oral patch. Examples of nasal administration include an aerosol. However, the dosage forms are not limited to these. These preparations can be produced by methods known in the art and usually used in a drug formulation process.

The pharmaceutical composition may contain various components commonly used; for example, at least one type of pharmacologically accepted excipient, disintegrant, diluent, lubricant, flavoring agent, colorant, sweetener, corrigent, suspending agent, wetting agent, emulsifier, dispersant, adjuvant, preservative, buffer, binder, stabilizer and coating agent can be contained. The pharmaceutical composition of the present invention may be a prolonged action form or sustained release form.

The dose of the therapeutic agent, prophylactic agent or the pharmaceutical composition of the present invention can be appropriately selected depending on, e.g., the route of administration, the body size, age, physical condition of the patient, severe or mild symptom of a disease and the period of a disease after onset of the patient. The pharmaceutical composition of the present invention can contain a therapeutically effective amount and/or prophylactically effective amount of the compound represented by Formula (I). In the present invention, the compound represented by Formula (I) can be used usually in a dose of 1 to 1000 mg/day/adult or 0.01 to 20 mg/day/kg body weight. The administration of the pharmaceutical composition may be a single or multiple dose administration.

The pharmaceutical composition of the present invention may contain, if necessary, components known in the art such as a colorant, a preservative, an aroma chemical, a flavoring agent, a coating agent, an antioxidant, a vitamin, an amino acid, a peptide, a protein and a mineral (iron, zinc, magnesium, iodine, etc.). The therapeutic agent or prophylactic agent of the present invention may have dosage forms suitable for, e.g., a pharmaceutical composition, a functional food, a healthy food, a beverage and a supplement, for example, solid preparations such as a granule (including dry syrup), a capsule (soft capsule, hard capsule), a tablet (including a chewable medicine), a powder medicine (powder) and a pill, or liquid preparations such as an internal medicine solution (including a liquid medicine, a suspension agent, a syrup). The therapeutic agent or prophylactic agent of the present invention can be used directly as, e.g., a pharmaceutical composition, a functional food, a healthy food and a supplement.

Examples for additives for drug-product formulation include an excipient, a lubricant, a binder, a disintegrant, a fluidizing agent, a dispersant, a wetting agent, a preservative, a thickening agent, a pH modifier, a colorant, a flavoring agent, a surfactant and a solubilizing agent. For formulation of a liquid medicine, a thickener such as pectin, xanthan gum and guar gum can be blended. Furthermore, coated tablets can be formed by using a coating agent and pasty glue can be formed. In the cases of other dosage forms, drug products may be prepared in accordance with a conventional method.

EXAMPLES

The present invention will be more specifically described by way of Examples; however, the present invention is not limited to these Examples.

Example 1

[Chemical Formula 5]

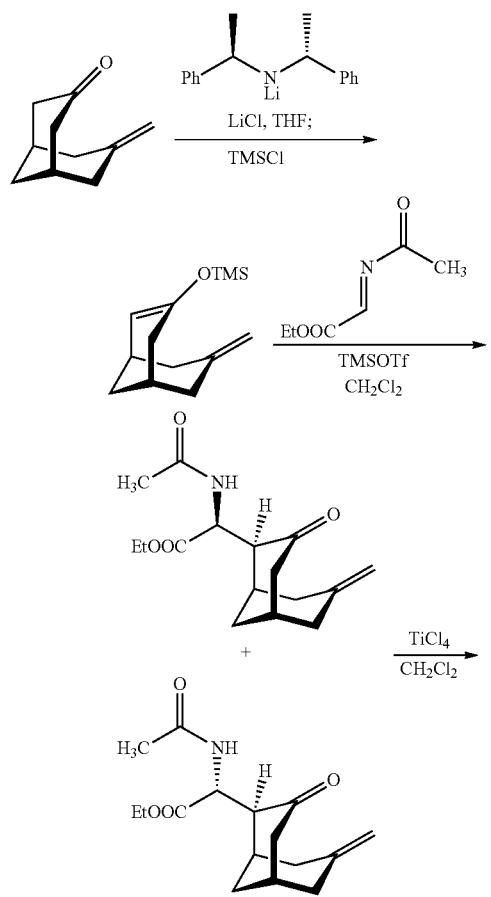

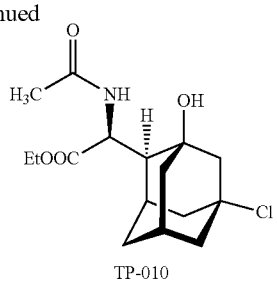

TP-010

+

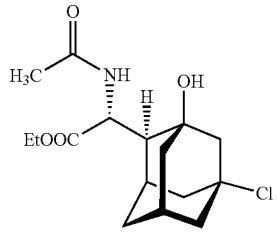

TP-011

To a solution of bis((R)-1-phenylethyl)amine (1.8 g, 18 mmol) in THF (30 mL), a solution of n-BuLi in hexane (1.56 M, 4.8 mL, 7.33 mmol) was added dropwise under cooling with ice. The reaction solution was stirred for 30 minutes at the same temperature, the reaction solution was cooled down to a temperature of −78° C. Thereafter, trimethylsilyl chloride (TMSCl, 1.7 mL, 13.3 mmol) was added and subsequently a solution of 7-methylenebicyclo[3.3.1]nonan-3-one (1.0 g, 16.6 mmol) in THF (5 mL) was added by cannulation. After stirring for one hour, water was added to the reaction solution, which was extracted with diethyl ether. The resultant organic layer was washed with saturated saline and dried over MgSO$_4$. The solvent was distilled off under reduced pressure. The residue was subjected to silica gel chromatography (hexane:ethyl acetate=9:1) to obtain a target substance, TMS enol ether (1.24 g, 84%) as colorless oil.

The TMS enol ether (400 mg, 1.80 mmol) obtained and ethyl (E)-2-(acetylimino)acetate (5.4 mmol) prepared in accordance with the method disclosed in the literature (Kobayashi S et al., J. Combi. Chem. 2001, 3, 401) were dissolved in dichloromethane (9 mL). The reaction solution was cooled to 0° C. To this solution, trimethylsilyl trifluoromethanesulfonate (TMSOTf, 240 μL, 900 μmol) was added. The solution was stirred at the same temperature for one hour, and then, a saturated aqueous NaHCO$_3$ solution was added to terminate the reaction. The reaction solution was extracted with ethyl acetate. The resultant organic layer was washed with saturated saline and dried over MgSO$_4$. The solvent was distilled off under reduced pressure to obtain the crude product (410 mg, oil) of the Mannich reaction. The crude product (400 mg) was dissolved in dichloromethane (7 mL) and cooled to −30° C. To the solution, TiCl$_4$ (120 μL, 1.09 mmol) was added. After stirring the solution for one hour at the same temperature, water was added to terminate the reaction. The solution was extracted with diethyl ether. After the resultant organic layer was washed with saturated saline and dried over MgSO$_4$, the solvent was distilled off under reduced pressure. The residue was subjected to silica gel column chromatography (hexane:ethyl acetate=10:1 to 9:1) to obtain TP-010 (148 mg, 25%) and TP-011 (228 mg, 52%).

TP-010 (84% ee): amorphous; $[\alpha]_D^{29}$=3.4 (c=1.832, CHCl$_3$); ($^1$H-NMR (400 MHz, CDCl$_3$): δ6.15 (d, J=8.8 Hz, 1H), 4.90 (t, J=9.6 Hz, 1H), 4.22-4.15 (m, 2H), 3.00 (s, 1H), 2.29 (br s, 1H), 2.15-1.95 (m, 8H), 2.04 (s, 3H), 1.85-1.78 (m, 2H), 1.50 (br d, J=12.7 Hz, 1H), 1.37 (br d, J=13.4 Hz, 1H), 1.28 (t, J=7.3 Hz, 3H); $^{13}$C-NMR (100 MHz, CDCl$_3$): δ173.1, 170.3, 70.8, 66.6, 61.8, 56.7, 51.8, 51.7, 47.9, 46.6, 37.7, 33.3, 31.8, 29.4, 23.4, 14.0; IR (neat, cm$^{-1}$): 3336, 1725, 1654; MS (EI): m/z 329 (M$^+$), 256 (100%); HRMS (EI): calcd for C$_{16}$H$_{24}$NO$_4$Cl (M+) 329.1394, found 329.1399.

TP-011 (84% ee): mp 65-68° C. (Et$_2$O-n-hexane); $[\alpha]_D^{29}$=−2.4 (c=1.72, CHCl$_3$); ($^1$H-NMR (400 MHz, CDCl$_3$): δ7.64 (br s, 1H), 4.42 (d, J=10.1, 3.9 Hz, 1H), 4.20 (q, J=7.1 Hz, 2H), 3.70 (s, 1H), 2.30 (br s, 1H), 2.20-1.88 (m, 9H), 1.98 (s, 3H), 1.88 (br d, J=13.9 Hz, 1H), 1.57 (br d, J=12.5 Hz, 1H), 1.38 (br d, J=12.5 Hz, 1H), 1.28 (t, J=7.1 Hz, 3H); $^{13}$C-NMR (100 MHz, CDCl$_3$): δ171.7, 170.4, 72.6, 66.0, 61.1, 56.6, 55.1, 48.9, 47.3, 46.2, 38.3, 34.3, 31.8, 29.0, 22.9, 14.1; IR (neat, cm$^{-1}$): 3377, 1739, 1650; MS (EI): m/z 329 (M$^+$), 256 (100%); HRMS (EI): calcd for C$_{16}$H$_{24}$NO$_4$Cl (M$^+$) 329.1394, found 329.1415.

Example 2

[Chemical Formula 6]

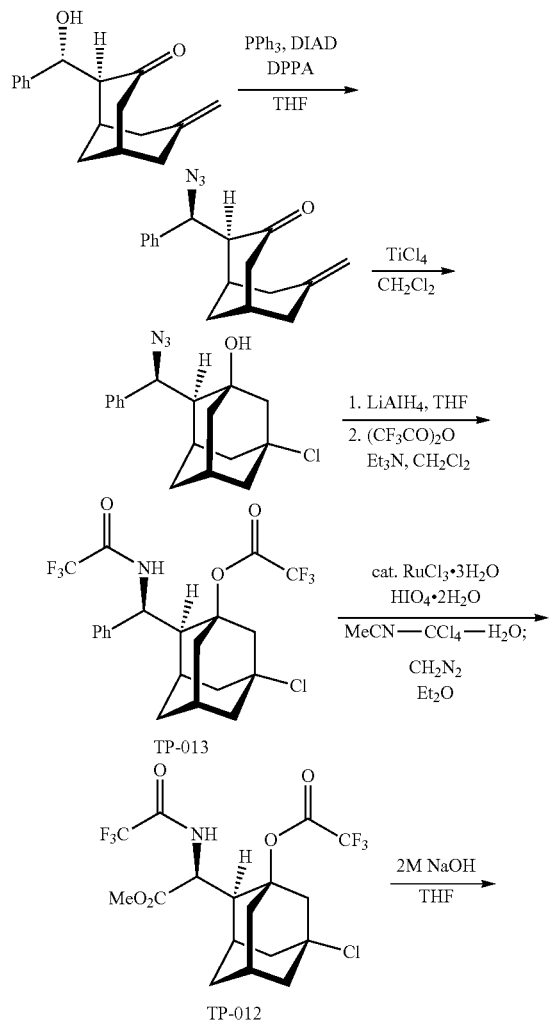

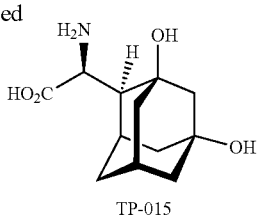

TP-015

To a solution of (1R,2S,5S)-2-((R)-hydroxy(phenyl)methyl)-7-methylenebicyclo[3.3.1]nonan-3-one (750 mg, 2.9 mmol), which was prepared in accordance with the method described in J. Am. Chem. Soc. 2014, 136, 17591-17600, diphenyl phosphate azide (DPPA, 820 μL, 3.81 mmol) and triphenylphosphine (1.20 g, 4.4 mmol) in THF (15 mL), diisopropyl azodicarboxylate (DIAD, 2.2 mL, 4.4 mmol) was added under cooling with ice. After stirring for one hour at the same temperature, the solvent was distilled off under reduced pressure. To the residue, dichloromethane (15 mL) was added and TiCl$_4$ (820 μL, 2.3 mmol) was added under cooling with ice. After the reaction solution was stirred at room temperature for 4 hours, a saturated aqueous NaHCO$_3$ solution was added under cooling with ice. The reaction solution was filtered with Celite (registered trade mark). The filtrate was extracted with diethyl ether. The resultant organic layer was washed with saturated saline and dried over MgSO$_4$. The solvent was distilled off under reduced pressure and the residue was subjected to silica gel column chromatography (hexane:ethyl acetate=10:1) to obtain (1R,2S,3R,5R,7R)-2-((S)-azido(phenyl)methyl)-5-chloroadamantan-1-ol (756 mg, 92%) as a white solid.

To solution of the resultant azide compound (750 mg, 2.67 mmol) in THF (14 mL), LiAlH$_4$ (300 mg, 8.00 mmol) was added under cooling with ice. After stirring for one hour at the same temperature, ammonia water was added to the reaction solution. The reaction solution was filtered by Celite (registered trade mark), the solvent was distilled off under reduced pressure. To the residue, dichloromethane (15 mL) was added, and thereafter, triethylamine (2.2 mL, 16.0 mmol) and anhydrous trifluoro acetic acid (TFAA, 1.2 mL, 8.0 mmol) were added under cooling with ice. After the reaction solution was stirred at room temperature overnight, a saturated aqueous NaHCO$_3$ solution was added. The reaction solution was extracted with dichloromethane. The resultant organic layer was dried over MgSO$_4$. The solvent was distilled off under reduced pressure and the residue was subjected to silica gel column chromatography (hexane:ethyl acetate=15:1) to obtain TP-013 (871 mg, 56%) as a white solid.

mp 83-85° C. (colorless needle crystal, n-hexane-Et$_2$O); $[\alpha]_D^{31}$=−84.1 (c=1.08, CHCl$_3$); $^1$H-NMR (400 MHz, CDCl$_3$): δ 7.35-7.27 (m, 5H), 6.63 (d, J=11.1 Hz, 1H), 5.44 (t, J=10.4 Hz, 1H), 3.26 (d, J=11.1 Hz, 1H), 2.99 (d, J=11.1 Hz, 1H), 2.45-2.41 (m, 3H), 2.26-2.13 (m, 5H), 1.96 (br d, J=12.4 Hz, 2H), 1.47 (br d, J=14.0 Hz, 1H); $^{13}$C-NMR (100 MHz, CDCl$_3$): δ 156.2 (q, J=37.4 Hz), 154.9 (q, J=42.3 Hz), 139.1, 129.2, 128.7, 127.1, 115.8 (q, J=288.1 Hz), 113.3 (q, J=287.3 Hz), 86.6, 65.1, 53.4, 50.2, 48.0, 46.9, 46.1, 35.6, 34.6, 31.7, 28.5; IR (neat, cm$^{-1}$): 3296, 2945, 1775, 1698; MS (EI): m/z 483 (M$^+$), 202 (100%); HRMS (EI): calcd for C$_{21}$H$_{20}$ClF$_6$NO$_3$ (M$^+$) 483.1036, found 483.1046.

To a solution containing TP-013 (550 mg, 1.14 mmol) in acetonitrile (1.8 mL)-carbon tetrachloride (1.8 mL)-water (1.8 mL), RuCl$_3$.3H$_2$O (114 μmol) and HIO$_4$.2H$_2$O (3.6 g, 16.0 mmol) were added under cooling with ice. The reaction solution was vigorously stirred at the same temperature for 8 hours. To the reaction solution, water was added. The reaction solution was extracted with dichloromethane. To the resultant organic layer, a solution of diazomethane in diethyl ether was added was under cooling with ice until the solution turned yellow. Thirty minutes later, nitrogen was blown into the solution to remove diazomethane and then the solvent was distilled off under reduced pressure. The residue was subjected to silica gel column chromatography (hexane:ethyl acetate=15:1) to obtain TP-012 (235 mg, 44%) as a white solid.

$[\alpha]_D^{24}$=−22.7 (c=1.84, CHCl$_3$); $^1$H-NMR (400 MHz, CDCl$_3$): δ7.10 (d, J=9.8 Hz, 1H), 5.02 (d, J=10.1 Hz, 1H), 3.76 (s, 3H), 2.92 (dd, J=10.3, 2.0 Hz, 1H), 2.74 (d, J=11.5 Hz, 1H), 2.69 (dd, J=11.5, 1.7 Hz, 1H), 2.43 (br s, 1H), 2.30-2.10 (m, 7H), 1.86 (d, J=14.1 Hz, 1H), 1.46 (d, J=14.1 Hz, 1H); $^{13}$C-NMR (100 MHz, CDCl$_3$): δ171.1, 157.1 (q, J=37.9 Hz), 155.2 (q, J=41.2 Hz), 115.5 (q, J=285.4 Hz), 113.8 (q, J=284.6 Hz), 87.0, 64.8, 53.0, 51.3, 49.8, 47.6, 46.5, 45.9, 34.2, 33.5, 31.7, 28.8; IR (neat, cm$^{-1}$): 3319, 1780, 1714; MS (EI): m/z 406 (M-CO$_2$CH$_3$); HRMS (EI): calcd for C$_{15}$H$_{15}$NO$_3$F$_6$Cl (M+) 406.0645, found 406.0651.

To a solution of TP-012 (256 mg, 550 µmol) in THF (2.0 mL), an aqueous NaOH solution (2 M, 2.0 mL) was added under cooling with ice. The reaction solution was stirred for two hours. After THF was distilled off, the reaction solution was neutralized with a 10% aqueous HCl solution, subjected to ion exchange chromatography (DOWEX50), eluted with a 0.23 N aqueous ammonium chloride solution and subjected to lyophilization to obtain TP-015 (48.5 mg, 34%) as a white solid.

$[\alpha]_D^{28}$=−46.3 (c=0.78, MeOH); ($^1$H-NMR (600 MHz, CD$_3$OD): δ3.87 (d, J=9.6 Hz, 1H), 2.26 (br s, 1H), 2.19 (br s, 1H), 2.12 (d, J=10.9 Hz, 1H), 2.08 (d, J=12.4 Hz, 1H), 1.80-1.62 (m, 5H), 1.66 (br s, 2H), 1.50 (br d, J=12.4 Hz, 1H), 1.37 (br d, J=13.1 Hz, 1H); $^{13}$C-NMR (150 MHz, CD$_3$OD): δ 174.6, 70.3, 68.6, 54.7, 53.8, 49.4, 44.3, 43.4, 38.7, 32.9, 30.9, 29.2; IR (neat, cm$^{-1}$): 3336, 1730; MS (FAB): m/z 242 (M+1); HRMS (FAB): calcd for C$_{12}$H$_{20}$NO$_4$ (M+1) 242.1387, found 252.1383.

Example 3

To a solution of (1R,2S,5S)-2-((R)-hydroxy(phenyl)methyl)-7-methylenebicyclo[3.3.1]nonan-3-one (256 mg, 1.00 mmol) in dichloromethane (5 mL), trimethylamine (0.42 mL, 3 mmol), dimethylaminopyridine (DMAP, 12 mg, 0.1 mmol) and anhydrous acetic acid (0.14 mL, 1.5 mmol) were added under cooling with ice. After the reaction solution was stirred at room temperature for 20 minutes, a saturated aqueous NaHCO$_3$ solution was added thereto under cooling with ice and extracted with dichloromethane. The resultant organic layer was dried over MgSO$_4$ and the solvent was distilled off under reduced pressure. The residue was subjected to silica gel column chromatography (hexane:ethyl acetate=4:1) to obtain (1R,2S,5S)-2-((R)-acetoxy(phenyl)methyl)-7-methylenebicyclo[3.3.1]nonan-3-one (289 mg, 97%) as a white solid.

To a solution of the resultant product (75.2 mg, 0.252 mmol) in dichloromethane (2.5 mL), trimethylsilyl azide (TMSN$_3$, 0.10 mL, 0.76 mmol) and BF$_3$·OEt$_3$ (0.04 mL, 0.30 mmol) were added at −20° C. The temperature of the reaction solution was gradually increased up to room temperature and the reaction solution was stirred for 3 hours. Subsequently, to the reaction solution, a saturated aqueous NaHCO$_3$ solution was added under cooling with ice. The resultant reaction solution was extracted with dichloromethane. The resultant organic layer was dried over MgSO$_4$ and the solvent was distilled off under reduced pressure. The residue was subjected to silica gel column chromatography (hexane:ethyl acetate=2:1) to obtain TP-009 (33.5 mg, 39%) as a white solid.

mp 114° C. (colorless crystal, n-hexane-Et$_2$O); $[\alpha]_D^{19}$=+56.0 (c=0.67, CHCl$_3$); $^1$H-NMR (400 MHz, CDCl$_3$): δ7.37-7.31 (m, 5H), 6.01 (d, J=10.6 Hz, 1H), 2.95 (br s, 1H), 2.27 (br s, 1H), 2.25 (d, J=10.6 Hz, 1H), 2.15 (d, J=13.0 Hz, 1H), 2.01 (s, 3H), 1.89-1.83 (m, 2H), 1.76-1.61 (m, 7H), 1.18 (d, J=13.0 Hz, 1H); $^{13}$C-NMR (100 MHz, CDCl$_3$): δ 169.6, 138.9, 128.7, 128.5, 127.3, 77.0, 71.3, 60.0, 51.9, 50.7, 41.6, 40.4, 38.8, 32.5, 30.6, 29.3, 21.6; IR (neat, cm$^{-1}$): 3460, 2931, 2091, 1732; MS (EI): m/z 323 (M$^+$-H$_2$O), 107 (100%); HRMS (EI): calcd for C$_{19}$H$_{21}$N$_3$O$_2$ (M$^+$-H$_2$O) 323.1634, found: 323.1613.

Example 4

[Chemical Formula 7]

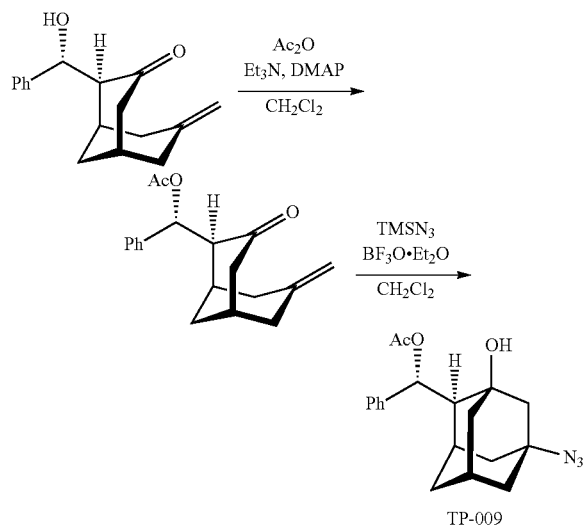

[Chemical Formula 8]

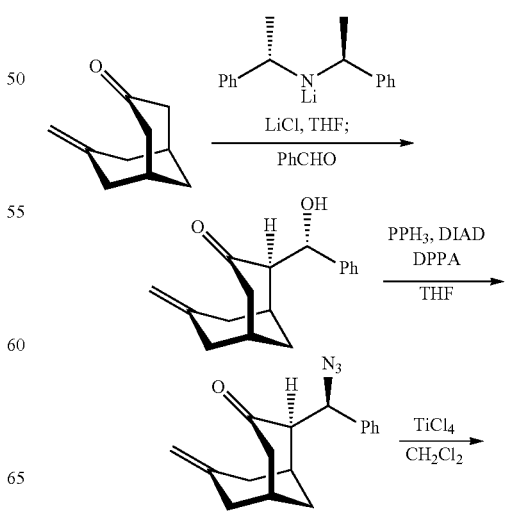

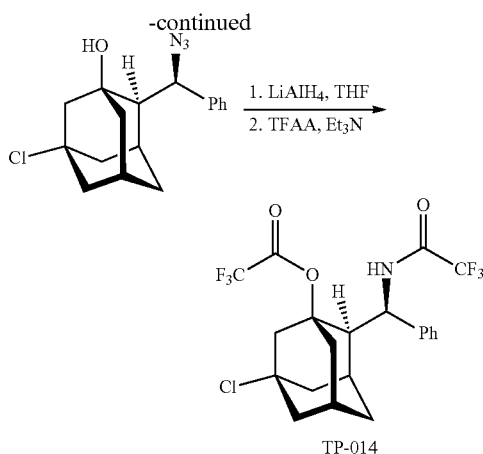

TP-014

To a solution of bis((S)-1-phenylethyl)amine (10.0 mL, 44 mmol) and lithium chloride (3.4 g, 80 mmol) in THF (100 mL), a solution of n-butyl lithium in hexane (1.56 M, 28.2 mL, 44 mmol) was added dropwise under cooling with ice. The reaction solution was stirred at the same temperature for 30 minutes and then cooled up to −78° C. To the reaction mixture, a solution of 7-methylenebicyclo[3.3.1]nonan-3-one (6.00 g, 40 mmol) in THF (60 mL) was added by cannulation. After the reaction solution was stirred for one hour, a solution of benzaldehyde (6.1 mL, 60 mmol) in THF (40 mL) was added by cannulation. After the reaction solution was stirred for 2 hours, acetic acid and a saturated aqueous ammonium chloride solution were sequentially added to the reaction solution. The reaction solution was extracted with diethyl ether. The resultant organic layer was washed with saturated saline and dried over MgSO$_4$. The solvent was distilled off under reduced pressure and the residue was subjected to silica gel column chromatography (hexane:ethyl acetate=4:1) to obtain (1S,2R,5R)-2-((S)-hydroxy(phenyl)methyl)-7-methylenebicyclo[3.3.1]nonan-3-one (8.3 g, 81%) as a white solid. This was recrystallized from diethyl ether to obtain colorless needle crystal.

mp 122° C.; [α]$_D^{21}$=−17.9 (c=0.32, CHCl$_3$); $^1$H-NMR (400 MHz, CDCl$_3$): δ7.38-7.25 (m, 5H), 4.79 (d, J=1.8 Hz, 1H), 4.76 (d, J=1.8 Hz, 1H), 4.71 (d, J=6.8 Hz, 1H), 2.90 (s, 1H), 2.64 (dd, J=15.7, 6.8 Hz, 1H), 2.48-2.18 (m, 6H), 2.01 (br d, J=14.3 Hz, 1H); $^{13}$C-NMR (100 MHz, CDCl$_3$): δ 211.0, 141.6, 128.8, 127.6, 114.8, 74.6, 62.7, 45.7, 42.2, 41.3, 32.4, 31.9, 28.4; IR (neat, cm$^{-1}$): 3390, 1711; MS (EI): m/z 256 (M$^+$), 95 (100%); HRMS (EI): calcd for C$_{17}$H$_{20}$O$_2$ (M+) 256.1463, found 256.1450.

To a solution of (1S,2R,5R)-2-((S)-hydroxy(phenyl)methyl)-7-methylenebicyclo[3.3.1]nonan-3-one (2.00 g, 7.5 mmol), DPPA (2.3 mL, 11 mmol) and triphenylphosphine (3.0 g, 11 mmol) in THF (38 mL), DIAD (2.2 mL, 11 mmol) was added under cooling with ice. After stirring for one hour at the same temperature, the solvent was distilled off under reduced pressure. To the residue, dichloromethane (38 mL) was added and TiCl$_4$ (0.8 mL, 7.5 mmol) was added under cooling with ice. After the reaction solution was stirred at room temperature for 4 hours, a saturated aqueous NaHCO$_3$ solution was added under cooling with ice. The reaction solution was filtered by Celite (registered trade mark) and the filtrate was extracted with diethyl ether. The resultant organic layer was washed with saturated saline and dried over MgSO$_4$. The solvent was distilled off under reduced pressure and tetrahydropyran (THP, 40 mL) was added to the residue. To this, LiAlH$_4$ (430 mg, 11 mmol) was added under cooling with ice. The reaction mixture was stirred at the same temperature for 30 minutes and ammonia water was added to the reaction solution. The reaction solution was filtered by Celite (registered trade mark) and the solvent was distilled off under reduced pressure. To the residue, dichloromethane (40 mL) was added, and then, triethylamine (6.3 mL, 45 mmol) and TFAA (3.2 mL, 23 mmol) were added under cooling with ice. The resultant reaction solution was stirred at room temperature overnight and a saturated aqueous NaHCO$_3$ solution was added thereto and then extracted with dichloromethane. The resultant organic layer was dried over MgSO$_4$. The solvent was distilled off under reduced pressure and the residue was subjected to silica gel column chromatography (hexane:ethyl acetate=15:1) to obtain a crude product as a white solid. This was recrystallized from diethyl ether-hexane to obtain TP-014 (1.27 g, 35%) as a white solid.

mp 89° C.; [α]$_D^{21}$=+89.1 (c=0.31, CHCl$_3$); $^1$H-NMR (400 MHz, CDCl$_3$): δ 7.35-7.27 (m, 5H), 6.63 (d, J=11.1 Hz, 1H), 5.44 (t, J=10.4 Hz, 1H), 3.26 (d, J=11.1 Hz, 1H), 2.99 (d, J=11.1 Hz, 1H), 2.45-2.41 (m, 3H), 2.26-2.13 (m, 5H), 1.96 (br d, J=12.4 Hz, 2H), 1.47 (br d, J=14.0 Hz, 1H); $^{13}$C-NMR (100 MHz, CDCl$_3$): δ 156.2 (q, J=37.4 Hz), 154.9 (q, J=42.3 Hz), 139.1, 129.2, 128.7, 127.1, 115.8 (q, J=288.1 Hz), 113.3 (q, J=287.3 Hz), 86.6, 65.1, 53.4, 50.2, 48.0, 46.9, 46.1, 35.6, 34.6, 31.7, 28.5; IR (neat, cm$^{-1}$): 3296, 2945, 1775, 1698; MS (EI): m/z 483 (M$^+$), 202 (100%); HRMS (EI): calcd for C$_{21}$H$_{20}$ClF$_6$NO$_3$ (M$^+$) 483.1036, found 483.1046; Anal.: calcd for C$_{21}$H$_{20}$ClF$_6$NO$_3$: C, 52.13; H, 4.17; N, 2.89. found C, 52.27; H, 4.18; N, 2.88.

Example 5

[Chemical Formula 9]

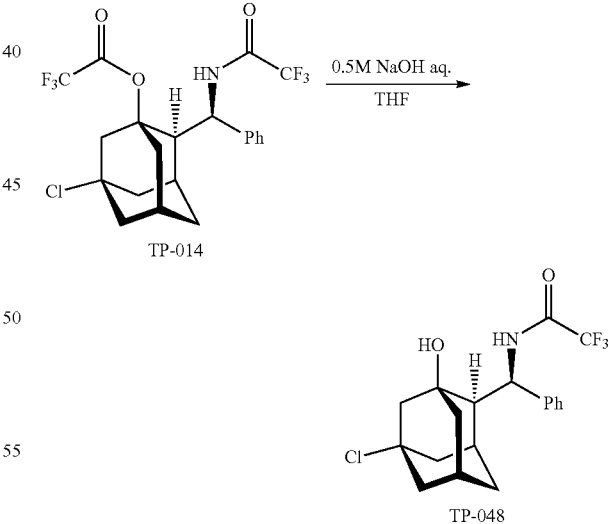

To a solution of TP-014 (84.7 mg, 0.175 mmol) in THF (2 mL), a 0.5 M aqueous NaOH solution (1 mL) was added under cooling with ice. The reaction solution was stirred at the same temperature for 15 minutes and a saturated NH$_4$Cl aqueous solution was added thereto and extracted with ethyl acetate. The resultant organic layer was washed with saturated saline and dried over MgSO$_4$. The solvent was distilled off under reduced pressure and the residue was subjected to silica gel column chromatography (hexane:ethyl acetate=8:1 to 4:1) to obtain TP-048 (65.5 mg, 96%) as a white solid.

$[\alpha]_D^{26}$=+109.2 (c=0.772, CHCl$_3$); $^1$H-NMR (400 MHz, CDCl$_3$): δ 7.41-7.32 (m, 5H), 6.98 (br, 1H), 5.34 (t, J=9.7 Hz, 1H), 2.36-2.29 (m, 3H), 2.19-2.00 (m, 7H), 1.77 (br d, J=11.6 Hz, 1H), 1.41-1.33 (m, 2H); $^{13}$C-NMR (100 MHz, CDCl$_3$): δ 156.2 (q, J=37.1), 140.5, 129.4, 128.6, 127.4, 115.8 (q, J=288.1 Hz), 72.3, 66.1, 56.7, 54.2, 52.4, 47.7, 46.3, 38.6, 34.4, 31.8, 28.8; IR (neat, cm$^{-1}$): 3553, 3297, 2940, 1698, 1552, 1208, 1183, 1165; MS (EI): m/z 387 (M$^+$), 202 (100%); HRMS (EI): calcd for C$_{19}$H$_{21}$ClF$_3$NO$_2$ (M$^+$) 387.1213, found 387.1196.

Example 6

[Chemical Formula 10]

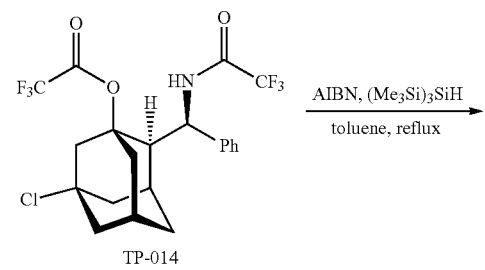

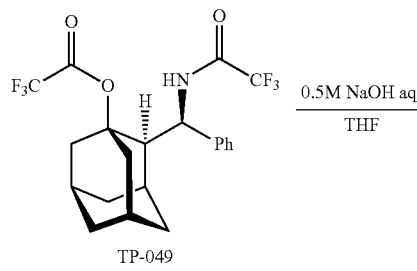

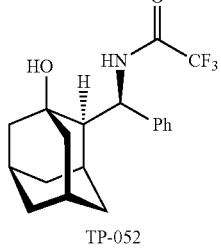

To a solution of TP-014 (30.0 mg, 0.062 mmol) in toluene (2 mL), tris(trimethylsilyl)silane (29 μL, 0.095 mmol) and azobisisobutyronitrile (AIBN, 2.0 mg, 0.012 mmol) were added at room temperature. After the reaction solution was heated under reflux overnight, the solvent was distilled off under reduced pressure. The residue was subjected to silica gel column chromatography (hexane:ethyl acetate=15:1) to obtain TP-049 (23.0 mg, 83%) as a white solid.

$[\alpha]_D^{29}$=+106.4 (c=0.385, CHCl$_3$); $^1$H-NMR (400 MHz, CDCl$_3$): δ 7.33-7.27 (m, 5H), 6.31 (br d, J=10.1 Hz, 1H), 5.50 (dd, J=10.9, 10.1 Hz, 1H), 3.20 (br d, J=10.9 Hz, 1H), 2.60 (br d, J=11.6 Hz, 1H), 2.45 (br d, J=12.1 Hz, 1H), 2.28-2.27 (m, 3H), 2.04-1.80 (m, 6H), 1.72 (br s, 2H); $^{13}$C-NMR (100 MHz, CDCl$_3$): δ 156.0 (q, J=37.1 Hz), 155.1 (q, J=41.8 Hz), 139.8, 129.0, 128.4, 127.2, 115.8 (q, J=288.1 Hz), 113.5 (q, J=287.3 Hz), 87.5, 53.6, 49.4, 41.3, 37.2, 36.1, 33.0, 30.6, 30.4, 30.2; IR (neat, cm$^{-1}$): 3335, 2927, 1775, 1700, 1556, 1218, 1169; MS (EI): m/z 449 (M$^+$), 202 (100%); HRMS (EI): calcd for C$_{21}$H$_{21}$F$_3$NO$_3$ (M$^+$) 449.1426, found 449.1447.

To a solution of TP-049 (61.5 mg, 0.137 mmol) in THF (1.4 mL), an aqueous NaOH solution (0.5 M, 0.5 mL) was added under cooling with ice. After the reaction solution was stirred at the same temperature for 5 minutes, 2 M hydrochloric acid was added to the reaction solution. The reaction solution was extracted with ethyl acetate. The resultant organic layer was washed with saturated saline and dried over MgSO$_4$. The solvent was distilled off under reduced pressure and the residue was subjected to silica gel column chromatography (hexane:ethyl acetate=4:1 to 2:1) to obtain TP-052 (49.4 mg, quant.) as a white solid.

TP-052: $[\alpha]_D^{14}$=+130.7 (c=0.243, CHCl$_3$); $^1$H-NMR (400 MHz, CDCl$_3$): δ 7.39-7.31 (m, 5H), 6.77 (br d, J=8.9 Hz, 1H), 5.40 (dd, J=9.7, 8.9 Hz, 1H), 2.32 (br d, J=9.7 Hz, 1H), 2.31-2.07 (m, 4H), 1.85-1.79 (m, 2H), 1.72-1.57 (m, 5H), 1.52-1.44 (m, 2H), 1.29 (br, 1H); $^{13}$C-NMR (100 MHz, CDCl$_3$): δ 156.1 (q, 37.1 Hz), 140.7, 129.4, 128.5, 127.5, 115.9 (q, 288 Hz), 77.2, 54.3, 53.0, 50.5, 48.5, 41.4, 39.6, 39.4, 33.2, 30.6, 29.6; IR (neat, cm$^{-1}$): 3566, 3291, 2919, 1698, 1183; MS (EI): m/z 353 (M$^+$), 151 (100%); HRMS (EI): calcd for C$_{19}$H$_{22}$F$_3$NO$_2$ (M$^+$) 353.1603, found 353.1604.

Example 7

[Chemical Formula 11]

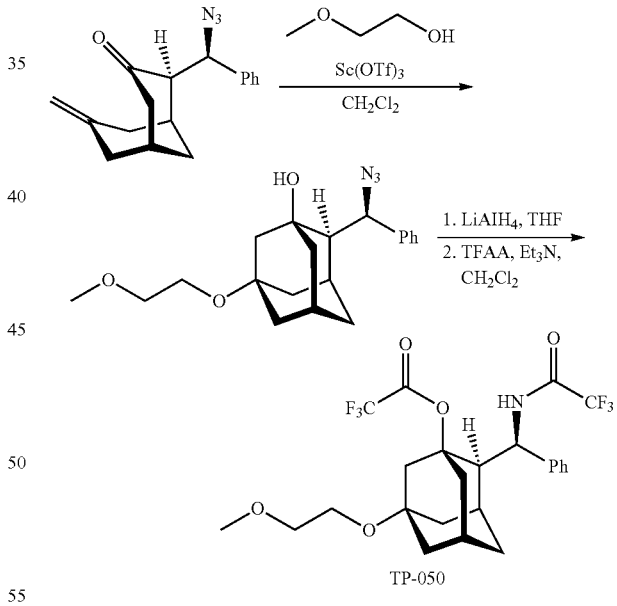

To a solution of (1S,2R,5R)-2-(R-azido(phenyl)methyl)-7-methylenebicyclo[3.3.1.]nonan-3-one (57.4 mg, 0.204 mmol) in dichloromethane (2 mL), 2-methoxyethanol (78 μL, 1.0 mmol) and scandium trifluoromethanesulfonate (5.0 mg, 0.01 mmol) were sequentially added under cooling with ice. After the reaction solution was stirred at room temperature for two days, a saturated aqueous NaHCO$_3$ solution was added under cooling with ice. The reaction solution was extracted with dichloromethane. The resultant organic layer was dried over MgSO$_4$ and the solvent was distilled off under reduced pressure. The residue was subjected to silica gel column chromatography (hexane:ethyl acetate=1:2 to 1:1) to obtain (1S,2R,3S,5S,7S)-2-((R)-azido(phenyl)methyl)-5-(2-methoxyethoxy)adamantan-1-ol (41.2 mg, 56%) as colorless oil.

To a solution of the resultant azide compound (39.6 mg, 0.111 mmol) in THF (1 mL), LiAlH$_4$ (8.0 mg, 0.21 mmol) was added under cooling with ice. The temperature of the reaction solution was gradually increased up to room temperature and the reaction solution was stirred for one hour. The reaction solution was ice-cooled and then LiAlH$_4$ (8.0 mg, 0.21 mmol) was added. After the reaction solution was stirred at room temperature for one hour, ammonia water was added to the reaction solution under cooling with ice. The reaction solution was filtered by Celite (registered trade mark). The filtrate was dried over Na$_2$SO$_4$ and the solvent was distilled off under reduced pressure. To the residue, dichloromethane (1 mL) was added, triethylamine (77 µL, 0.56 mmol) and anhydrous trifluoro acetic acid (TFAA, 47 µL, 0.33 mmol) were added under cooling with ice. After the reaction solution was stirred at room temperature for 5 hours, a saturated aqueous NaHCO$_3$ solution was added under cooling with ice. The reaction solution was extracted with dichloromethane. The resultant organic layer was dried over MgSO$_4$. The solvent was distilled off under reduced pressure and the residue was subjected to silica gel column chromatography (hexane:ethyl acetate=1:4 to 1:2) to obtain TP-050 (31.6 mg, 54%) as colorless oil.

[α]$_D^{25}$=+72.1 (c=0.965, CHCl$_3$); $^1$H-NMR (400 MHz, CDCl$_3$): δ 7.34-7.23 (m, 5H), 6.33 (br d, J=9.9 Hz, 1H), 5.44 (dd, J=10.9, 9.9 Hz, 1H), 3.59-3.56 (m, 2H), 3.51-3.48 (m, 2H), 3.37 (s, 3H), 3.17 (br d, J=10.9 Hz, 1H), 2.65 (br d, J=10.6 Hz, 1H), 2.43-2.37 (m, 3H), 1.95-1.81 (m, 7H), 1.38 (br d, J=11.6 Hz, 1H); $^{13}$C-NMR (100 MHz, CDCl$_3$): δ 156.1 (q, J=37.4 Hz), 154.9 (q, J=42.1 Hz), 139.4, 129.1, 128.5, 127.2, 115.8 (q, J=288.1 Hz), 113.4 (q, J=287.3 Hz), 87.6, 73.7, 72.3, 60.2, 59.1, 53.5, 48.5, 45.0, 41.1, 39.9, 36.3, 30.5, 29.2; IR (neat, cm$^{-1}$): 3303, 2936, 1775, 1698, 1554, 1221, 1172; MS (EI): m/z 523 (M$^+$), 202 (100%); HRMS (EI): calcd for C$_{24}$H$_{27}$F$_6$NO$_5$ (M$^+$) 523.1793, found 523.1797.

Example 8

[Chemical Formula 12]

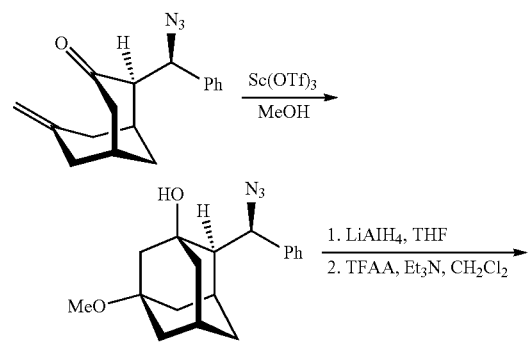

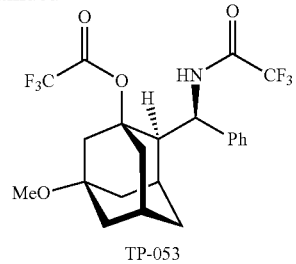

TP-053

To a solution of (1S,2R,5R)-2-(R-azido(phenyl)methyl)-7-methylenebicyclo[3.3.1.]nonan-3-one (238 mg, 0.848 mmol) in methanol (8.5 mL), scandium trifluoromethanesulfonate (20 mg, 0.04 mmol) was added under cooling with ice. After the reaction solution was stirred at room temperature for 18 hours, a saturated aqueous NaHCO$_3$ solution was added to the reaction solution under cooling with ice. The reaction solution was extracted with ethyl acetate. The resultant organic layer was washed with saturated saline and dried over MgSO$_4$ and the solvent was distilled off under reduced pressure. The residue was subjected to silica gel column chromatography (hexane:ethyl acetate=1:4 to 1:2) to obtain (1S,2R,3S,5S,7S)-2-((R)-azido(phenyl)methyl)-5-methoxyadamantan-1-ol (225 mg, 85%) as colorless oil.

To a solution of the resultant azide compound (225 mg, 0.716 mmol) in THF (4 mL), LiAlH$_4$ (41 mg, 1.1 mmol) was added under cooling with ice. After stirring for one hour at the same temperature, ammonia water was added to the reaction solution. The reaction solution was filtered by Celite (registered trade mark) and the solvent was distilled off under reduced pressure. To the residue, dichloromethane (4 mL) was added, and triethylamine (497 µL, 3.86 mmol) and anhydrous trifluoro acetic acid (TFAA, 299 µL, 2.15 mmol) were added under cooling with ice. After the reaction solution was stirred at room temperature for 40 hours, a saturated aqueous NaHCO$_3$ solution was added under cooling with ice. The reaction solution was extracted with dichloromethane. The resultant organic layer was dried over MgSO$_4$ and the solvent was distilled off under reduced pressure. The residue was subjected to silica gel column chromatography (hexane:ethyl acetate=1:8 to 1:2) to obtain TP-053 (262 mg, 75%) as a white solid.

[α]$_D^{14}$=+97.2 (c=0.179, CHCl$_3$); $^1$H-NMR (400 MHz, CDCl$_3$): δ 7.33 (m, 5H), 6.35 (br d, J=9.9 Hz, 1H), 5.45 (dd, J=10.6, 9.9 Hz, 1H), 3.25 (s, 3H), 3.17 (br d, J=10.6 Hz, 1H), 2.61 (br d J=10.6 Hz, 1H), 2.45-2.37 (m, 3H), 1.97-1.73 (m, 7H), 1.39 (br d, J=13.5 Hz, 1H); $^{13}$C-NMR (100 MHz, CDCl$_3$): δ 156.0 (q, J=37.4 Hz), 155.0 (q, J=41.8 Hz), 139.4, 129.1, 128.6, 127.1, 115.8 (q, 288.1 Hz), 113.4 (q, 287.0 Hz), 87.7, 75.5, 53.5, 48.7, 48.6, 44.5, 40.8, 39.5, 36.3, 33.3, 30.4, 29.3; IR (neat, cm$^{-1}$): 3299, 2941, 1776, 1697, 1221, 1172; MS (EI): m/z 479 (M$^+$), 202 (100%); HRMS (EI): calcd for C$_{22}$H$_{23}$F$_6$NO$_4$ (M$^+$) 479.1531, found 479.1486.

Example 9

[Chemical Formula 13]

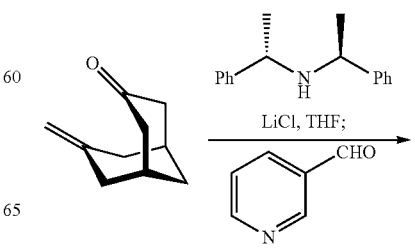

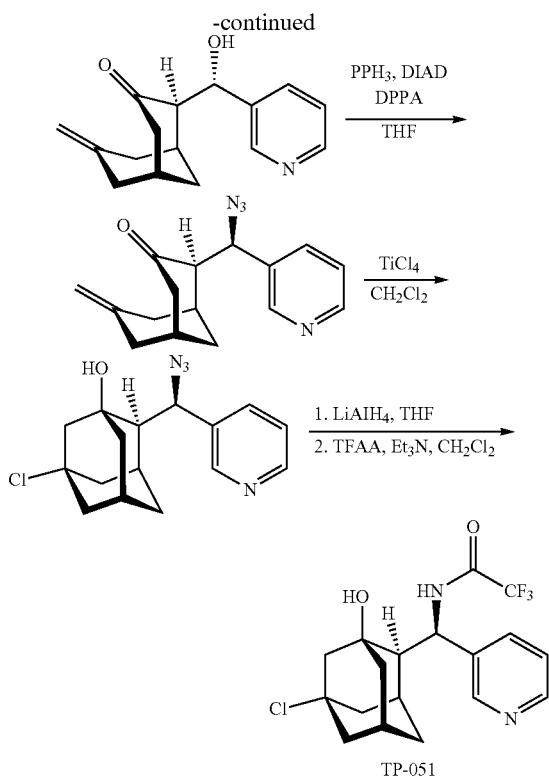

To a solution of bis((S)-1-phenylethyl)amine (2.5 mL, 11 mmol) and lithium chloride (850 mg, 20 mmol) in THF (25 mL), a solution of n-butyl lithium in hexane (1.56 M, 7.1 mL, 11 mmol) was added dropwise under cooling with ice. After the reaction solution was stirred at the same temperature for 30 minutes, the reaction solution was cooled down to −78° C. To the reaction mixture, a solution of 7-methylenebicyclo[3.3.1]nonan-3-one (1.52 g, 10 mmol) in THF (15 mL) was added by cannulation. After the reaction solution was stirred for 30 minutes, a solution of nicotinaldehyde (1.1 mL, 12 mmol) in THF (10 mL) was added by cannulation. After the reaction solution was stirred for 40 minutes, acetic acid and a saturated aqueous ammonium chloride solution were sequentially added to the reaction solution. The reaction solution was extracted with ethyl acetate. The resultant organic layer was washed with saturated saline and dried over $K_2CO_3$. The solvent was distilled off under reduced pressure. The residue was subjected to silica gel column chromatography (hexane-acetone=3:2 to 1:2) to obtain (1S,2R,5R)-2-((S)-hydroxy(pyridin-3-yl)methyl)-7-methylenebicyclo[3.3.1]nonan-3-one (2.7 g, 81%) as a white solid. This was recrystallized from ethyl acetate to obtain colorless crystal (99% ee).

A solution of the resultant alcohol (258 mg, 1.0 mmol), diphenyl phosphate azide (DPPA, 237 μL, 1.1 mmol) and triphenylphosphine (239 mg, 1.1 mmol) in THF (5 mL), diisopropyl azodicarboxylate (DIAD, 214 μL, 1.1 mmol) was added under cooling with ice. The temperature of the reaction solution was gradually increased up to room temperature. After the reaction solution was stirred for 5 hours, the solvent was distilled off under reduced pressure. The residue was subjected to silica gel column chromatography (hexane:ethyl acetate=4:1 to 2:1) to obtain (1S,2R,5R)-2-((R)-azido(pyridin-3-yl)methyl)-7-methylenebicyclo[3.3.1]nonan-3-one (187 mg, 66%) as colorless oil.

To a solution of the resultant azide compound (187 mg, 0.66 mmol) in dichloromethane (7 mL), $TiCl_4$ (300 μL, 0.27 mmol) was added under cooling with ice. After the reaction solution was stirred at room temperature for 3 hours, a saturated aqueous $NaHCO_3$ solution was added under cooling with ice. The reaction solution was extracted with diethyl ether. The resultant organic layer was washed with saturated saline, and dried over $MgSO_4$. The solvent was distilled off under reduced pressure and the resultant solid was washed with cold diethyl ether to obtain (1S,2R,3S,5S,7S)-2-((R)-azido(pyridin-3-yl)methyl)-5-chloroadamantan-1-ol (98.5 mg, 92%).

To a solution of the resultant compound (75.4 mg, 0.257 mmol) in THF (2 mL), $LiAlH_4$ (23 mg, 0.61 mmol) was added under cooling with ice. After the reaction solution was stirred for one hour at the same temperature, ammonia water was added to the reaction solution under cooling with ice. The reaction solution was filtered by Celite (registered trade mark) and the solvent was distilled off under reduced pressure. The residue was subjected to silica gel column chromatography ($CHCl_3$:methanol=1:0 to 4:1) to obtain crude amine.

To the resultant crude amine, dichloromethane (2 mL) was added and then triethylamine (178 μL, 1.28 mmol) and anhydrous trifluoro acetic acid (TFAA, 107 μL, 0.76 mmol) were added under cooling with ice. The temperature of the reaction solution was increased up to room temperature. After the reaction solution was stirred for 4 hours, a saturated aqueous $NaHCO_3$ solution was added thereto under cooling with ice. The reaction solution was extracted with dichloromethane. The resultant organic layer was dried over $Na_2SO_4$. The solvent was distilled off under reduced pressure. The residue was subjected to silica gel column chromatography (hexane:ethyl acetate=2:1 to 1:4) to obtain TP-051 (48.8 mg, 49%) as a white solid.

$[\alpha]_D^{20}$=+53.9 (c=0.379, $CHCl_3$); $^1$H-NMR (400 MHz, $CDCl_3$): δ 8.57 (d, J=1.0 Hz, 1H), 8.50 (dd, J=4.9, 1.5 Hz, 1H), 7.72 (br d, J=7.8 Hz, 1H), 7.41 (br d, J=9.8 Hz, 1H), 7.32 (dd, J=7.8, 4.9 Hz, 1H), 5.35 (dd, J=9.8, 9.3 Hz, 1H), 2.40-2.38 (m, 2H), 2.29 (br s, 1H), 2.22-1.99 (m, 7H), 1.75 (br, 1H), 1.68 (br d, J=13.7 Hz, 1H), 1.48 (br d, J=13.2 Hz, 1H), 1.42 (br d, J=13.2 Hz, 1H); $^{13}$C-NMR (100 MHz, $CDCl_3$): δ 156.4 (q, J=37.1 Hz), 148.2, 147.7, 138.3, 136.5, 124.0, 115.8 (q, J=287.8 Hz), 71.9, 66.1, 57.3, 52.6, 51.7, 47.6, 46.3, 38.3, 34.3, 31.6, 28.6; IR (neat, cm$^{-1}$): 3292, 2938, 1700, 1558, 1212, 1184, 1161, 759; MS (EI): m/z 388 (M$^+$), 203 (100%); HRMS (EI): calcd for $C_{18}H_{20}ClF_3N_2O_2$ (M$^+$) 388.1165, found 388.1177.

Test Example 1

A plasmid vector having cDNA of Kir6.2 channel inserted therein: pcDNA3.1-Kir6.2, was obtained from Dr. Toru Ishizuka (Graduate School of Life Sciences, Tohoku University). The plasmid vector, pcDNA3.1-Kir6.2, was conditioned in accordance with the manual attached to GenElute HP Plasmid Maxiprep Kit (manufactured by Sigma-Aldrich). A culture solution (composition: DMEM culture solution 450 mL containing 50 ml of bovine serum and 100 units of penicillin/streptomycin) of Neuro2A cells (N2A cells, the National Instituted of Biomedical Innovation) cultured in DMEM culture solution (Gibco) was exchanged with Opti-Mem (Gibco)(containing Lipofectamine R2000 (1 μg/1 ml)) containing pcDNA3.1-Kir6.2 (1 μg/μl) conditioned above, and cultured for 5 hours to obtain N2A cells overexpressing Kir6.2 channel. Exchange with the DMEM culture solution was again performed and culture was carried out for two days. Thereafter, memantine (manufactured by Sigma-Aldrich) and the compound of the present invention (n=4 per group) were added in the culture solutions (DMEM, Gibco) so as to obtain a concentration of 10 nM based on the culture solution, and the culture solutions were allowed to stand still for one hour. Thereafter, Kir6.2 channel overexpressing N2A cells were collected and an SDS sample buffer was added to the N2A cells to prepare a suspension. The suspension was subjected to immunoblotting by use of an anti-phosphorylated CaMKII antibody (Fukunaga K et al., J. Biol. Chem. 1992, 267, 22527-22533) as a primary antibody and an anti-rabbit IgG antibody (manufactured by SouthernBiotech) as a secondary antibody (other conditions except the aforementioned antibodies were the same as those employed in ordinary immunoblotting), to investigate activation of CaMKII. As a result, in TP-009, TP-010, TP-011, TP-012, TP-014, TP-015, TP-048, TP-049, TP-050, TP-051, TP-052, TP-053, bands showing a reaction with the antibody against phosphorylated CaMKII were obtained. It was confirmed that activation of CaMKII is enhanced. The results are shown in FIG. 1. In FIG. 1, the result of the case (control: c) where a test compound was not added is regarded as 100%. CaMKII activation of the cases containing memantine, TP-009, TP-010, TP-011, TP-012, TP-014, TP-015, TP-048, TP-049, TP-050, TP-051, TP-052, TP-053 (corresponding to M, 9, 10, 11, 12, 12, 15, 48, 49, 50, 51, 52 and 53, respectively) were shown in FIG. 1.

Test Example 2

Using Kir6.2 channel-overexpressing cells obtained in Test Example 1, potassium current flowing outside from the cells was measured by an ordinary patch-clamp method. The results are shown in FIG. 2. ATP-sensitive potassium channel (Kir6.2 channel) was localized in the cell membrane of the nerve cells. If the channel is inhibited and closed, the threshold of the nerve cell membrane rises to produce a state analogous to the state where an action potential is temporarily generated, with the result that potassium current flows out from cells outside and, in place, calcium current flows into the cells from outside. FIG. 2*a* shows that Kir6.2 channel is overexpressed in N2A cells (the upper figure shows stained images by immunoblotting; whereas the lower figure quantitatively expresses the signal intensity of bands). This was confirmed by applying immunoblotting (the same conditions as in Test Example 1 were employed except that anti-Kir6.2 channel antibody, n=5) with an anti-Kir6.2 channel antibody (prepared based on a customary method) to Kir6.2 channel-overexpressing cells (prepared by the aforementioned method). No change was observed in a housekeeping gene product, i.e., β tubulin (anti-β tubulin antibody was obtained from Sigma-Aldrich, and other conditions are the same as those in the detection of Kir6.2). FIG. 2*b* (confirmed results) shows that if Kir6.2 channel-overexpressing cells are allowed to stand still in an electrophysiological experimental buffer containing TP-014 so as to obtain a concentration of 10 nM, potassium current, which outwardly flows when the membrane potential of nerve cells is changed toward a plus side, is suppressed (n=5 per group). The results show that TP-014 inhibits Kir6.2 channel and inhibits potassium current flowing outside from the cells.

Test Example 3

Figure 3A:
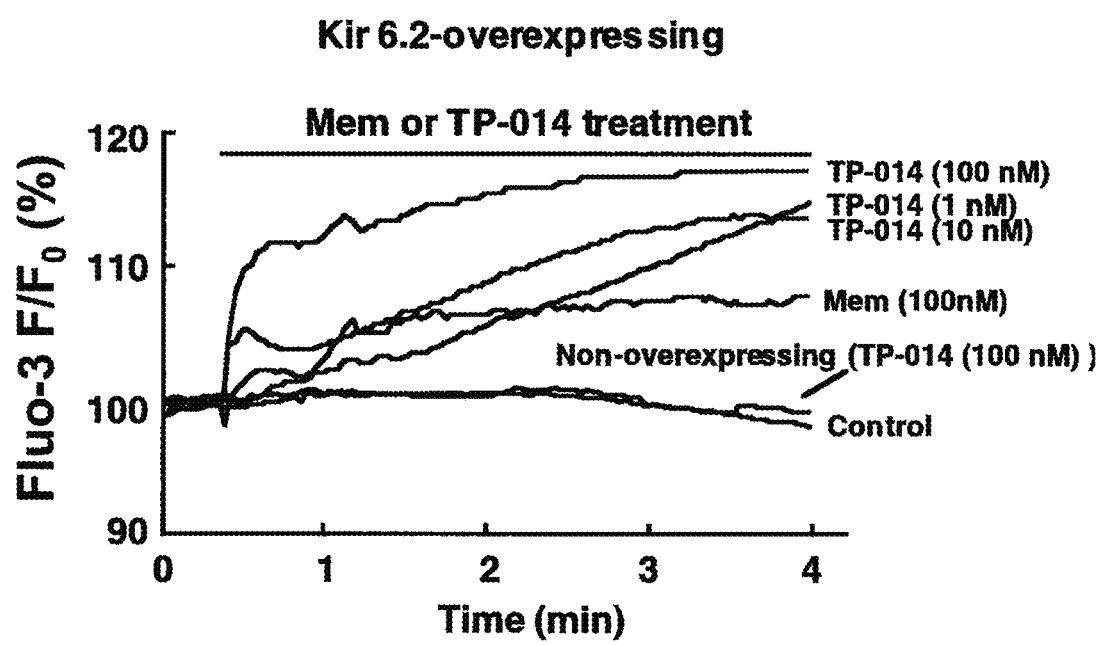
FIG. 3a shows the assay results by a calcium imaging method, showing that the intracellular calcium concentration in Kir6.2 channel-overexpressing cells increases by administration of TP-014. A change of concentration-dependent calcium amount with time (four minutes) was checked in the cases treated with the compound of the present invention and memantine. The results show that TP-014 inhibits Kir6.2 channel and increases intracellular calcium concentration.
Figure 3B:
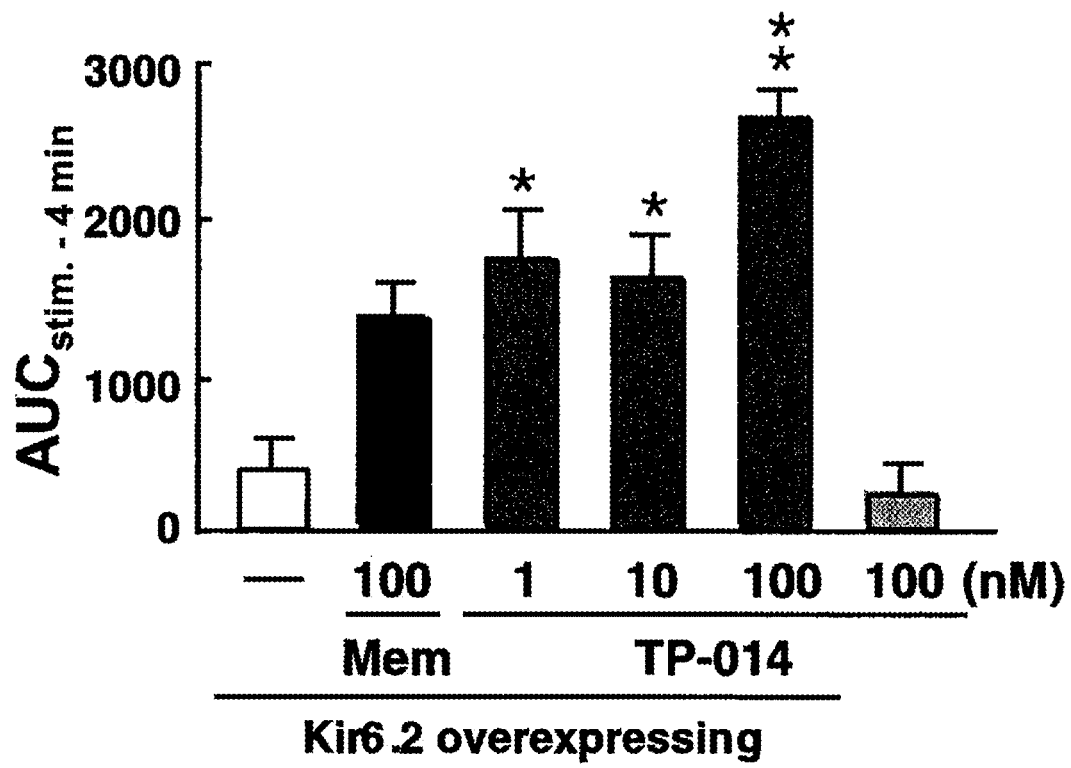
FIG. 3b shows the assay results by a calcium imaging method, showing that intracellular calcium concentration in Kir6.2 channel-overexpressing cells increases by administration of TP-014. The calcium amounts were measured 4 minutes after treatment with memantine and the compound of the present invention. The group using Kir6.2 expressing cells (Neuro2A cells) is confirmed to have a significant difference from a non-drug treatment group (−). The results show that TP-014 inhibits Kir6.2 channel and increases the intracellular calcium concentration.

Using the same Kir6.2 channel-overexpressing cells as in Test Example 1, the amount of calcium that flows into cells from outside the cells by TP-014 treatment was measured by a calcium imaging method. The results are shown in FIG. 3. The calcium imaging method is a method of measuring the amount of calcium based on the intensity of fluorescence of cultured nerve cells, which are treated in a culture solution containing a calcium fluorescent dye (Fura2, manufactured by Dojindo Laboratories) in a concentration of 4 μM. Imaging was carried out by an imaging apparatus (LAMBDA10-2, manufactured by SUTTER INSTRUMENT) in accordance with the manual attached to the apparatus. FIG. 3*a* shows a change of the TP-014 concentration-dependent calcium amount with time (for 4 minutes) when treatment was performed with TP-014 (1 to 100 nM) and memantine (100 nM). FIG. 3*b* shows the measurement results of calcium amount when measurement was carried out 4 minutes after the treatment with memantine (100 nM) and TP-014 (1-100 nM) (n=5 per group). TP-014 has a larger calcium concentration increasing effect than memantine. It was confirmed that the amount of calcium within cells is significantly increased by the treatment with TP-014, due to inhibition of outflow of potassium from the cells confirmed in Test Example 2.

Test Example 4

Figure 4A:
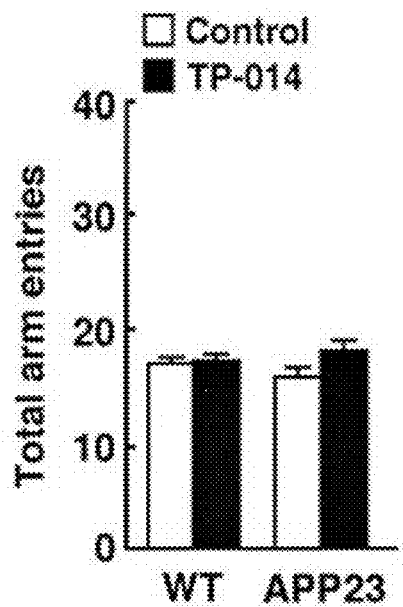
FIG. 4a shows the results of the experiment in which TP-014 was administered to Alzheimer's disease model mice (APP23 mice) (12 month-old) for two months and analysis was made by the Y-maze method, showing that cognitive function is effectively improved.
Figure 4B:
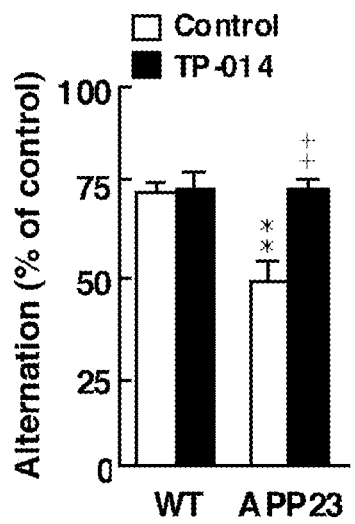
FIG. 4b shows the results of an experiment in which TP-014 was administered to Alzheimer's disease model mice (APP23 mice) (12 month-old) for two months and analysis was made by the Y-maze method, showing that cognitive function is effectively improved. The case having a significant difference between wild-type (WT) and APP23 mice in the ratio giving a correct answer (alteration) in memory learning is indicated by **; and the case having a significant difference between APP mice and a control (non-treated group) is indicated by ++.

To Alzheimer's disease model mice (APP23 mice, Sturchler-Pierrat et al., Proc. Natl. Acad. Sci. U.S.A. 1997, 94, 13287-13292)(12 months old), TP-014 (1 mg/kg) was orally administered once a day for two months (chronic treatment). As a result, a significance cognitive function improvement effect was confirmed. The results are shown in FIG. 4. FIGS. 4*a-d* show the results of behavior analysis. FIG. 4*a* and FIG. 4*b* show attentional function analyzed on WT mice (C57BL/6J, Japan SLC) and APP23 mice (n=5 per group) by an ordinary Y-maze method. As a result, it was confirmed that a significant attentional function improvement effect is exerted by treatment with TP-014. The Y-maze method is a method of allowing mice to freely walk on three arms for 8 minutes. The arms will be provisionally designated as A, B, C, respectively. A mouse positioned on A will move to B or C (arm). The case where the mouse moves to B and then moves to C, in short, the case of sequentially moving A-B-C, is regarded as a right answer; whereas the case where a mouse moves A-B-A and avoid choosing a new arm is regarded as a wrong answer. The arms to which a mouse moved are recorded in chronological order and the number of times a mouse moves to each of the arms within a predetermined time is counted and determined as "total arm entries". Of them, the number of the right-answer cases (the case where a mouse consecutively chooses three different arms) was counted and determined as the number of alternating behaviors ("No. of alternation"). The ratio of "No. of alternation" to the number obtained by subtracting 2 from the "total arm entries" is expressed as alternation (%) and used as the normal alternate behavior index (spatial working memory correct answer ratio).

Mice tends to favor a new (unfamiliar) object. The ratio of ordinary mice giving the correct answer is 70%; however the ratio of APP23 mice giving correct answer is as low as about 50%. Based on the percentages as the reference, attentional function (cognitive function) is analyzed.

Figure 4C:
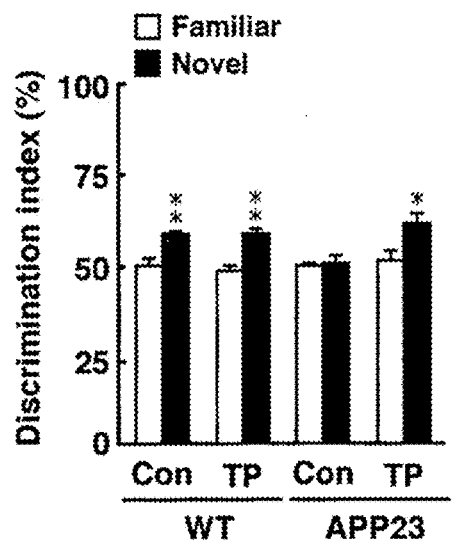
FIG. 4c is a graph showing the results of an experiment in which TP-014 was administered to Alzheimer's disease model mice (APP23 mice) (12 month-old) for two months and analysis was made by a new object recognition test method, showing that cognitive function is effectively improved. The case of Novel (new object) having a significant difference with Familiar (same object) in each mouse group is indicated by **

FIG. 4*c* shows the results of memory for a new (unfamiliar) object of WT mice and APP23 mice (both, n=5) assessed by an ordinary new-object recognition test method. The new object recognition test method is carried out as follows. Two identical shape building blocks are placed in a mouse cage and mice are allowed to play for 10 minutes (this is referred to as a training trial). One hour later, one of the building blocks was replaced with a different-shaped building block. Since normal mice show interest on a new object, they play a longer time with the different-shaped building block. The Alzheimer's disease (model) mice, since the mice fail to recognize the new object (building block), are seemed to have memory disturbance. Mice are allowed to freely play for further 5 minutes with two building blocks different in shape (this is referred to as retention trial). In the training trial and retention trial, the number of times a mouse is in contact with each of the two objects was counted. The ratio (%) of the number of contact times to the different-shaped building block to the total number of contact times in the retention trial was calculated and used as a discrimination index.

Figure 4D:
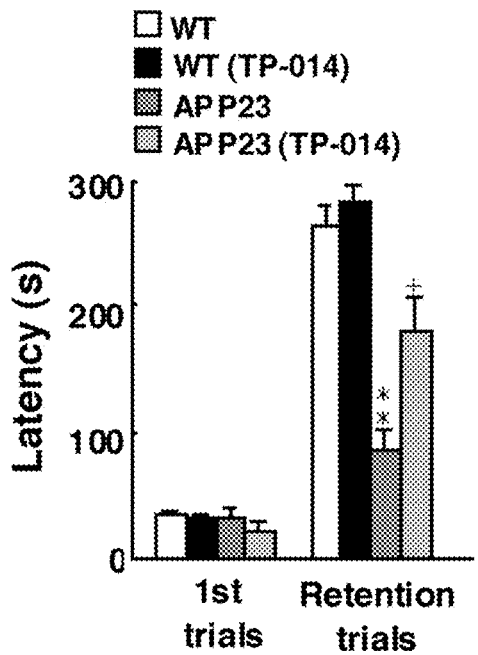
FIG. 4d shows results of an experiment in which TP-014 was administered to Alzheimer's disease model mice (APP23 mice)(12 month-old) for two months and analysis was made by a fear conditioning test method, showing that cognitive function is effectively improved. In Retention trials, a case having a significant difference with WT is indicated by **; and a case having a significant difference with APP23 mice is indicated by +.

FIG. 4d shows the results of fear memory analyzed by an ordinary fear conditioning test method (n=5 per group). The fear conditioning test method is an analysis taking an advantage of mouse's preposition in favor of a dark place rather than a bright place. Day 1, a mouse is placed in a bright place. Since a mouse is fond of a dark place, the mouse enters a dark place (dark box). When an electrical stimulation is given to the mouse at this time, the mouse is surprised and returns to the bright place and never enters the dark place. Day 2, the mouse is placed in the bright place (the same place as on Day 1), and then, whether the mouse enters a dark place or not is observed for 5 minutes. If the mouse enters the dark place right away, it is determined that fear memory of the mouse declined. "Latency" is a time period (seconds) until the mouse placed in a bright place enters the dark plate (darkroom) on Day 2. Since APP23 mice entered a dark place right away, it was confirmed that fear memory declined; however, in the mice treated with TP-014 for two months, an improvement effect was confirmed.

Figure 4E:
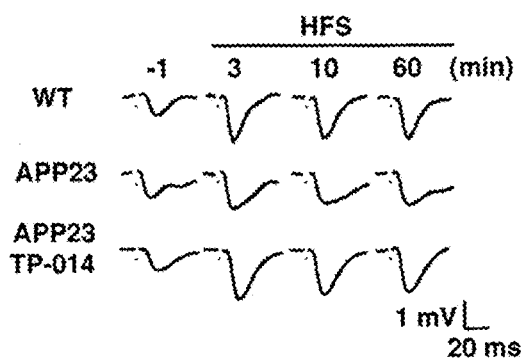
FIG. 4e shows the results of an experiment in which TP-014 was administered to Alzheimer's disease model mice (APP23 mice) (12 month-old) for two months and analysis was made on long-term potentiation phenomenon (LTP) serving as an index of memory formation, by an electrophysiological technique.
Figure 4F:
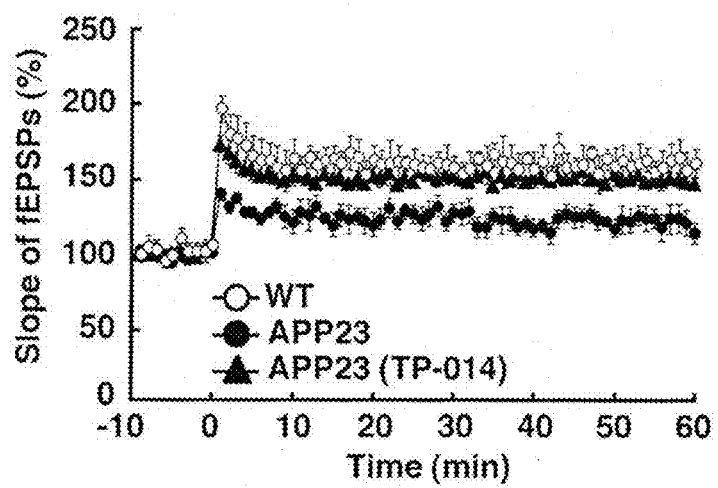
FIG. 4f shows the results of an experiment in which TP-014 was administered to Alzheimer's disease model mice (APP23 mice) (12 month-old) for two months and analysis was made on long-term potentiation phenomenon (LTP) serving as an index of memory formation, by an electrophysiological technique.
Figure 4G:
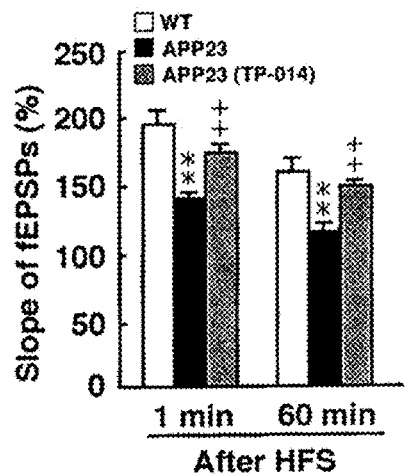
FIG. 4g shows the results of an experiment in which TP-014 was administered to Alzheimer's disease model mice (APP23 mice) (12 month-old) for two months and analysis was made on long-term potentiation phenomenon (LTP) serving as an index of memory formation, by an electrophysiological technique. The case having a significant difference with WT is indicated by **; and the case having a significant difference with APP23 mice is indicated by ++ or +.

FIG. 4e to FIG. 4g show the results of long-term potentiation phenomenon (LTP)(serving as an index of memory formation) analyzed by an electrophysiological technique. The hippocampus in the brain plays an important role in memorization. The hippocampus was cut into slice sections (400 micrometers in thickness). The slice sections were placed in an artificial cerebrospinal fluid (126 mM NaCl, 5 mM KCL, 26 mM NaHCO$_3$, 1.3 mM MgSO$_4$·7H$_2$O, 1.26 mM KH$_2$PO$_4$, 2.4 mM CaCl$_2$·2H$_2$O, 10 mM glucose) saturated with a 95% O$_2$/5% CO$_2$ gas at 34° C. for two hours and recovered. The hippocampal slice sections were transferred to a measuring chamber and the artificial cerebrospinal fluid containing TP-014 was perfused. The activity of the nerve cells when electrical stimulation was applied was recorded and the postsynaptic assembly potential (fEPSP) was measured. Based on them, the degree of LTP improvement was evaluated. The waveforms recorded are shown in FIG. 4e. Thereafter, an electrical stimulation (100 Hz) was applied to the hippocampus to cause a sparse change (it is considered that memory is formed by a sparse change in the hippocampus). It was confirmed that an increase rate of the neuronal excitation decreases in APP23 mice; whereas the increase rate is improved in the mice chronically treated with TP-014. It is shown that memory learning is effectively improved by improvement of LTP.

Test Example 5

Figure 5A:
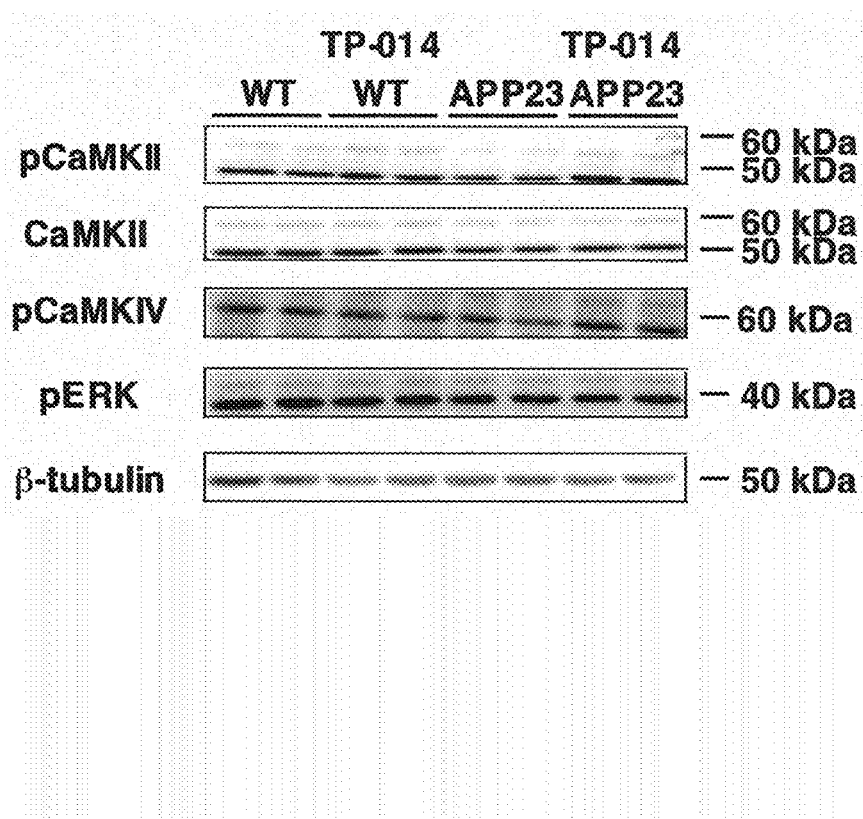
FIG. 5a shows bands (image) obtained by electrophoresis of immunoblots, showing the results of phosphorylation of proteins analyzed by immunoblotting using antibodies against CaMKII, CaMKIV and ERK.
Figure 5B:
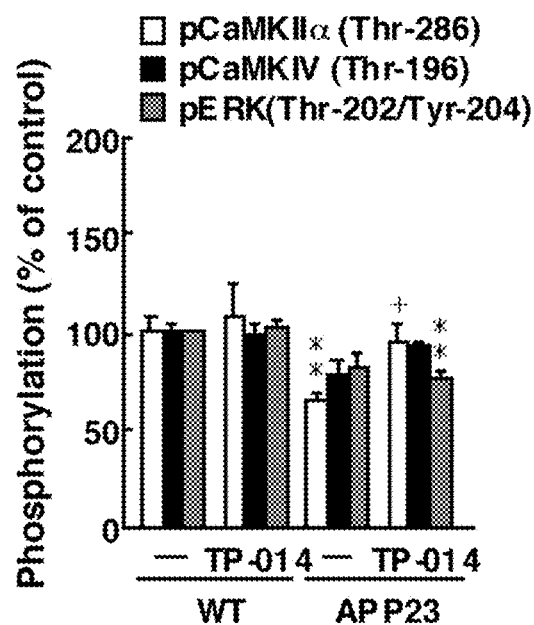
FIG. 5b shows the results of quantitative analysis of the signal intensity of the bands (in FIG. 5a) obtained by electrophoresis of immunoblots. The case having a significant difference with WT(−) (non-treated group with a drug) is indicated by **; and the case having a significant difference with a group of APP23 mice not treated with a drug (−) is indicated by +.

The hippocampus of APP23 mouse was excised out. To hippocampal slices, an SDS sample buffer was added to prepare a suspension, which was subjected to immunoblotting using antibodies against CaMKII, CaMKIV and ERK (CaMKII: Fukunaga et al., J. Biol. Chem. 1992, 267, 22527-22533, CaMKIV: Kasahara et al., J. Biol. Chem. 2001, 276, 24044-24050, ERK: manufactured by Sigma-Aldrich). In this manner, phosphorylation of the individual proteins was analyzed. The results are shown in FIG. 5a and FIG. 5b. CaMKII, CaMKIV and ERK are molecules all considered to play an important role in memory formation. As a result, it was observed that phosphorylation of CaMKII decreases in ordinary APP23 mice; whereas, in APP23 mice chronically treated with TP-014 (the treatment conditions are the same as in the case of Test Example 4), phosphorylation of CaMKII is accelerated. From the result, it is demonstrated that activation of CaMKII is important in effectively improving memory of APP23 mice by TP-014 treatment.

Figure 5C:
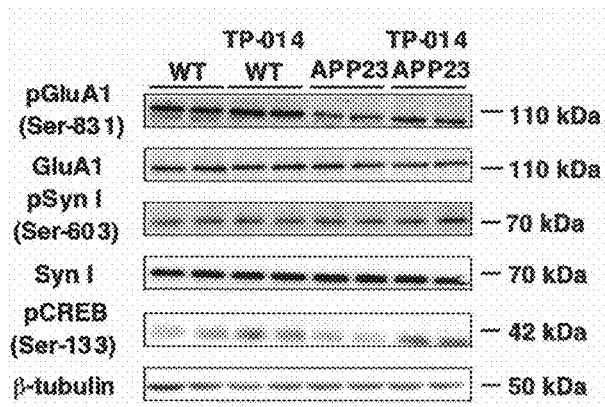
FIG. 5c shows bands (image) obtained by electrophoresis of immunoblots, showing the results of phosphorylation of proteins analyzed by immunoblotting using antibodies against CaMKII, CaMKIV and ERK.
Figure 5D:
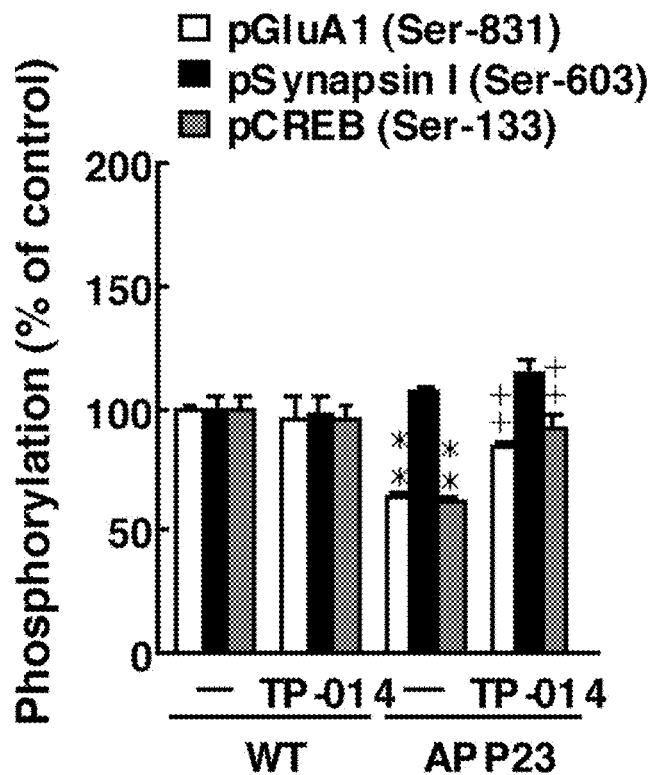
FIG. 5d shows the results of quantitative analysis of the signal intensity of the bands (in FIG. 5c) obtained by electrophoresis of immunoblots. The case having a significant difference with WT(−) (non-treated group with a drug) is indicated by **; and the case having a significant difference with a group of APP23 mice not treated with a drug (−) is indicated by ++.
Figure 6A:
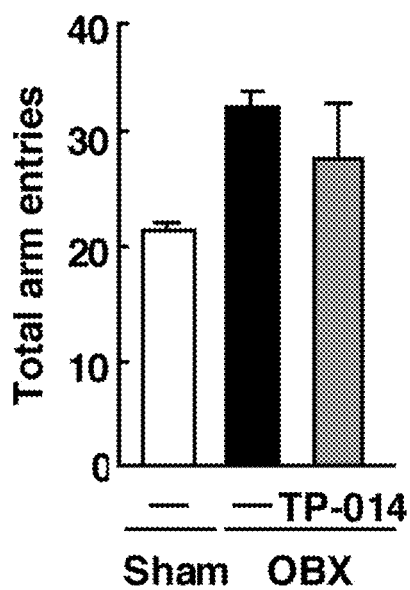
FIG. 6a shows the results of an experiment in which TP-014 was administered to neurodegenerative disease model mice, i.e., olfactory bulbectomized mice (OBX mice) for two months and analysis was made by the Y-maze method, showing that cognitive function is effectively improved.
Figure 6B:
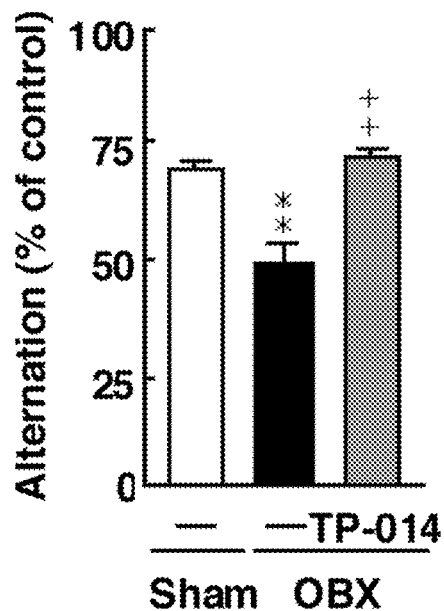
FIG. 6b shows the results of an experiment in which TP-014 was administered to neurodegenerative disease model mice, i.e., olfactory bulbectomized mice (OBX mice) for two months and analysis was made by a Y-maze method, showing that cognitive function is effectively improved. In OBX mice, the case having a significant difference in the ratio giving a correct answer (alternation) of memory learning with WT is indicated by **; and the case having a significant difference with a control (non-treated group) of OBX mice is indicated by ++.
Figure 6C:
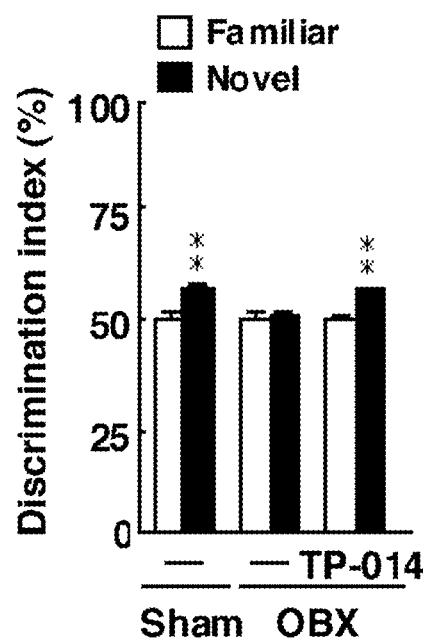
FIG. 6c shows the results of an experiment in which TP-014 was administered to neurodegenerative disease model mice, i.e., olfactory bulbectomized mice (OBX mice) for two months and analysis was made by a new object recognition test method, showing that cognitive function is effectively improved. The case of Novel (new object) having a significant difference with Familiar (familiar object) in each mouse group is indicated by **
Figure 6D:
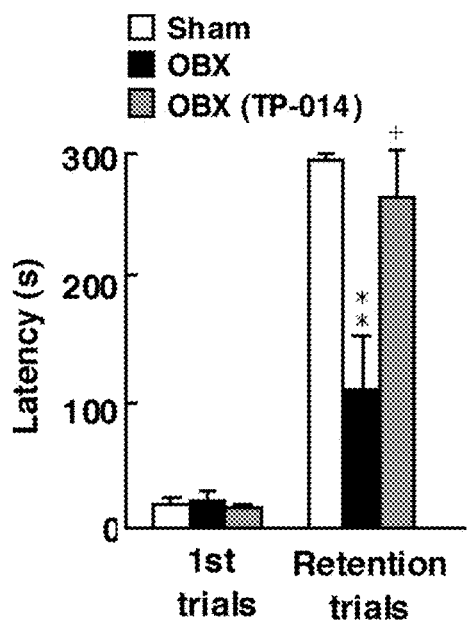
FIG. 6d shows the results of an experiment in which TP-014 was administered to neurodegenerative disease model mice, i.e., olfactory bulbectomized mice (OBX mice) for two months and analysis was made by a fear conditioning test method, showing that cognitive function is effectively improved. In Retention trials, a case having a significant difference with WT is indicated by **; and a case having a significant difference with OBX mice is indicated by +.
Figure 6E:
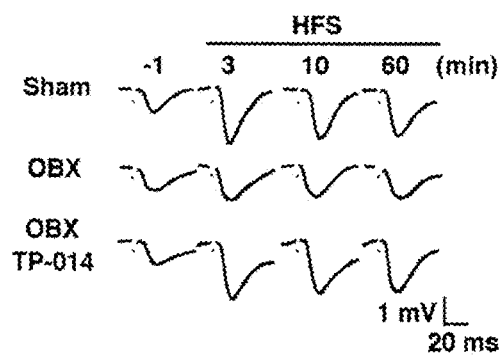
FIG. 6e shows the results of an experiment in which TP-014 was administered to neurodegenerative disease model mice, i.e., olfactory bulbectomized mice (OBX mice) for two months and analysis was made on long-term potentiation phenomenon (LTP) serving as an index of memory formation, by an electrophysiological technique.
Figure 6F:
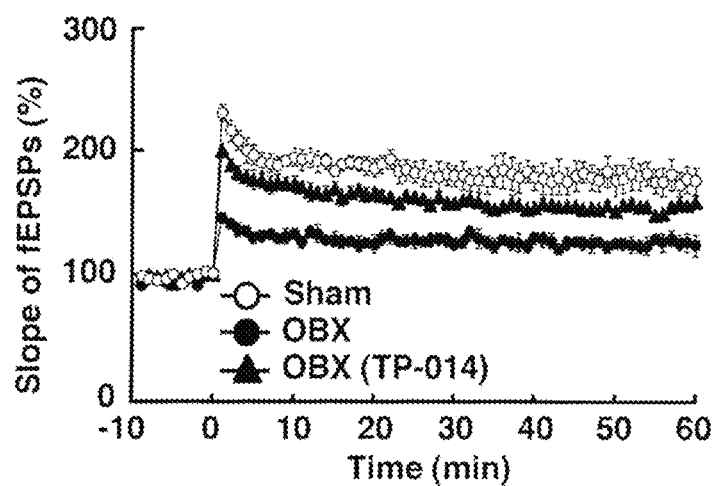
FIG. 6f shows the results of an experiment in which TP-014 was administered to neurodegenerative disease model mice, i.e., olfactory bulbectomized mice (OBX mice) for two months and analysis was made on long-term potentiation phenomenon (LTP) serving as an index of memory formation, by an electrophysiological technique.
Figure 6G:
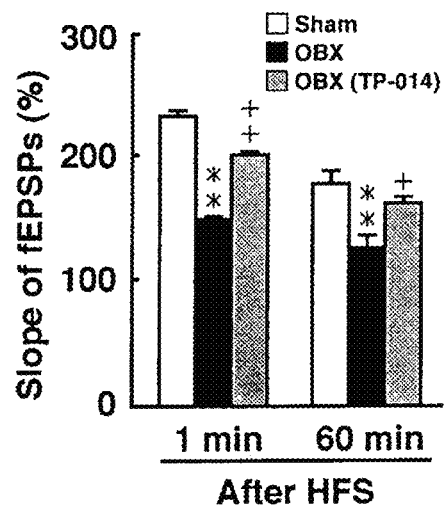
FIG. 6g shows the results of an experiment in which TP-014 was administered to neurodegenerative disease model mice, i.e., olfactory bulbectomized mice (OBX mice) for two months and analysis was made on long-term potentiation phenomenon (LTP) serving as an index of memory formation, by an electrophysiological technique. The case having a significant difference with Sham is indicated by **; and the case having a significant difference with OBX mice by ++ or +.
Figure 7A:
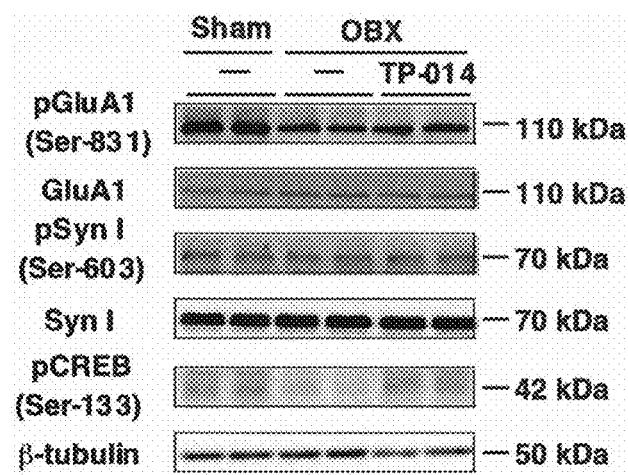
FIG. 7a shows bands (image) obtained by electrophoresis of immunoblots, showing the results of phosphorylation of proteins analyzed by immunoblotting using antibodies against CaMKII, CaMKIV and ERK.
Figure 7B:
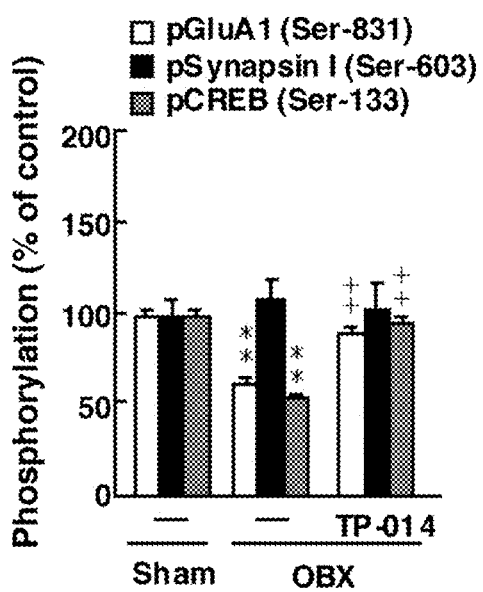
FIG. 7b shows the results of quantitative analysis of the signal intensity of the bands (in FIG. 7a) obtained by electrophoresis of immunoblots.
Figure 7C:
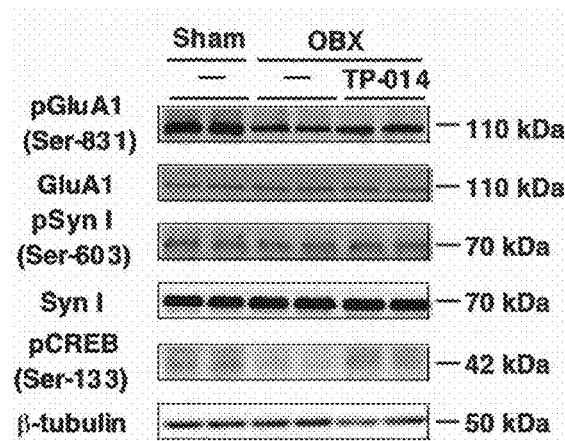
FIG. 7c shows bands (image) obtained by electrophoresis of immunoblots, showing the results of phosphorylation of proteins analyzed by immunoblotting using antibodies against CaMKII, CaMKIV and ERK.
Figure 7D:
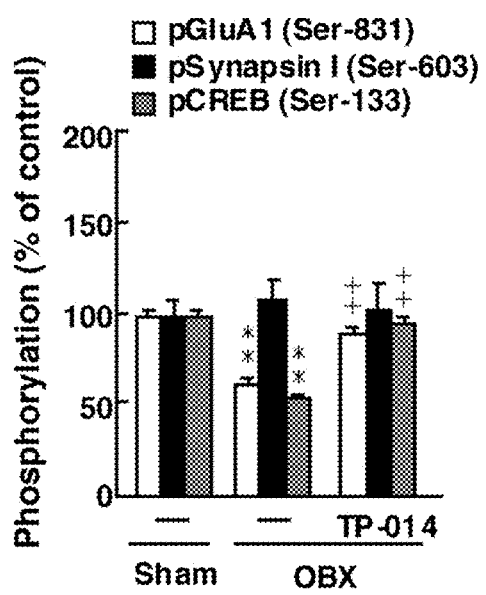
FIG. 7d shows the results of quantitative analysis of the signal intensity of the bands (in FIG. 7c) obtained by electrophoresis of immunoblots. The case having a significant difference with WT(−)(non-treated group with a drug) is indicated by **; and the case having a significant difference with a group of OBX mice not treated with a drug (−) is indicated by ++.

GluA1 (Ser-831), Synapsin I (Ser-603) and CREB (Ser-133), which are molecules known to be activated if CaMKII is activated. These molecules were analyzed by immunoblotting of hippocampal slice sections suspended in an SDS sample buffer. Antibodies against the individual molecules were obtained from Millipore. The results are shown in FIG. 5c and FIG. 5d. It is shown that activation of GluA1 (Ser-831) and CREB (Ser-133) is induced by activation of CaMKII. FIG. 5a and FIG. 5c show bands (image) actually obtained by electrophoresis of immunoblots. FIG. 5b and FIG. 5d show analysis results quantitatively showing signal intensities of the bands shown in FIG. 5a and FIG. 5c.

Test Example 6

The same experiment as that shown in FIG. 4 was carried out by using neurodegenerative disease model mice, i.e., olfactory bulbectomized mice (OBX mice). The results are shown in FIG. 6a to FIG. 6g. Cognitive dysfunction of OBX mice was significantly improved by chronic administration (2 weeks) with TP-014. The OBX mice were prepared from DDY male mice of 10 weeks old (Nippon SLC, Hamamatsu, Japan). Bulbectomy surgery was carried out under anesthesia with pentobarbital sodium (50 mg/kg i.p.; Dainippon, Osaka, Japan). The mouse was fixed on a brain anchor and the skull above the olfactory bulb was punctuated by a drill to make a hole of 1 mm in diameter. The olfactory bulb was removed by a suction pump so as not to hurt the prefrontal cortex. A sham group was prepared by subjecting mice to the same operation as in OBX group except that the olfactory bulb was removed by suction.

Test Example 7

The intracellular mechanism of cognitive dysfunction in OBX mice was investigated in the same manner as in FIG. 5. The results are shown in FIG. 7a to FIG. 7d. It was found that activation of CaMKII and CaMKIV is important in the hippocampus, which plays an important role in memory formation. In addition, it was confirmed that activation of GluA1 (Ser-831) and CREB (Ser-133), which are downstream molecules of CaMKII and CaMKIV in activation, is also important. The antibodies against GluA1 (Ser-831) and CREB (Ser-133) were both obtained from Millipore. From the results of FIGS. 4 to 7, it was found that it is important to accelerate activation of CaMKII and CaMKIV for cognitive function improvement effect of TP-014. Since cognitive dysfunction is not observed in CaMKIV gene defective mice, CaMKII is important in cognitive function improvement effect.

Test Example 8

Figure 8A:
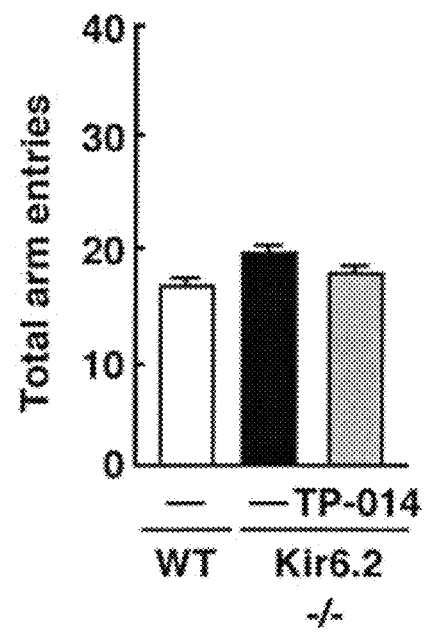
FIG. 8a shows a graph showing the results of the experiment in which TP-014 was administered to Kir6.2 channel deficient mice for two months and analysis was made by the Y-maze method, showing that cognitive function is effectively improved.
Figure 8B:
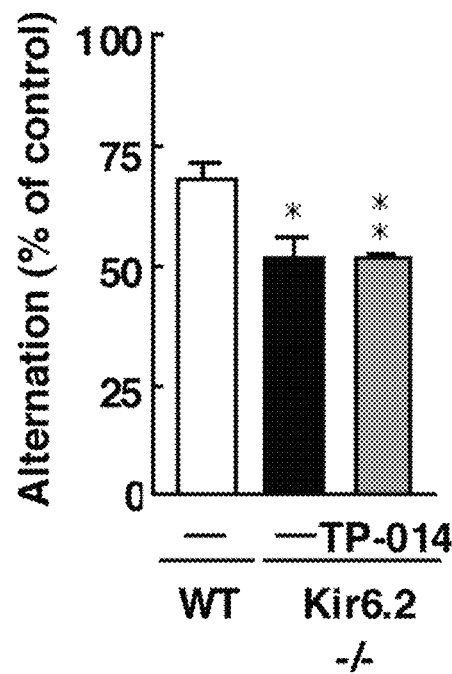
FIG. 8b shows the results of an experiment in which TP-014 was administered to Kir6.2 channel deficient mice for two months and analysis was made by the Y-maze method, showing that cognitive function is effectively improved. The case having a significant difference between Kir6.2 deficient mice and WT in the ratio giving a correct answer (alteration) in memory learning is indicated by * or **
Figure 8C:
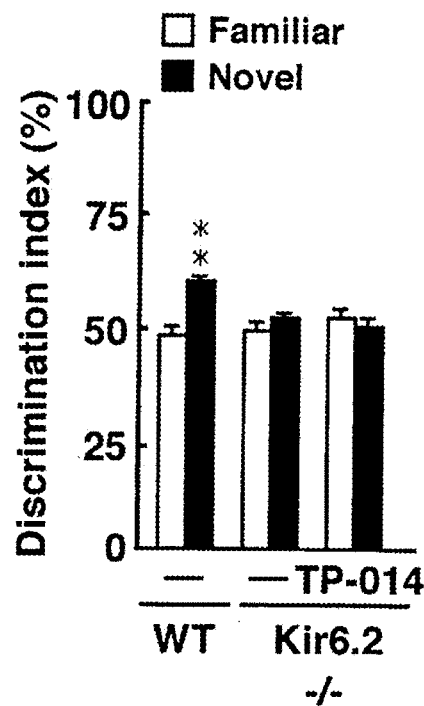
FIG. 8c shows a graph showing the results of an experiment in which TP-014 was administered to Kir6.2 channel deficient mice for two months and analysis was made by a new object recognition test method, showing that cognitive function is effectively improved. The case of Novel (new object) having a significant difference with Familiar (familiar object) in each mouse group is indicated by **
Figure 8D:
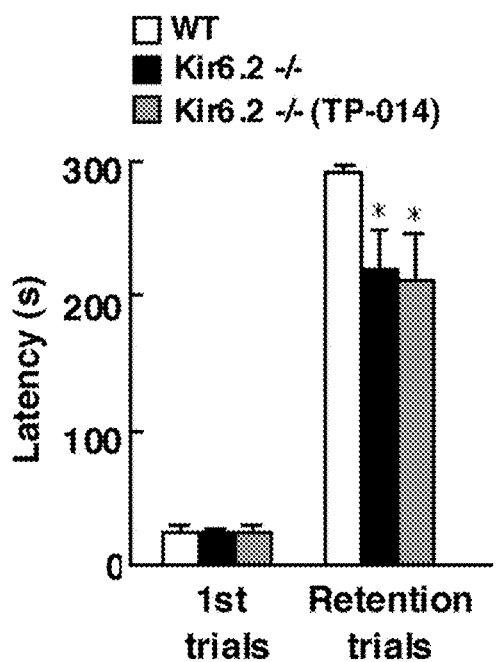
FIG. 8d shows a graph showing the results of an experiment in which TP-014 was administered to Kir6.2 channel deficient mice for two months and analysis was made by a fear conditioning test method, showing that cognitive function is effectively improved. In Retention trials, a case having a significant difference with WT is shown by *.
Figure 8E:
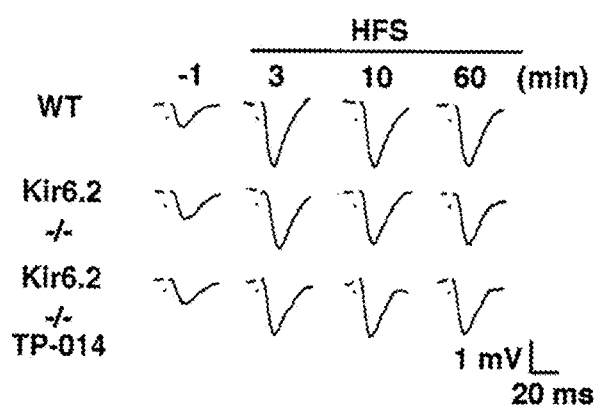
FIG. 8e shows the results of an experiment in which TP-014 was administered to Kir6.2 channel deficient mice for two months and analysis was made on long-term potentiation phenomenon (LTP) serving as an index of memory formation, by an electrophysiological technique.
Figure 8F:
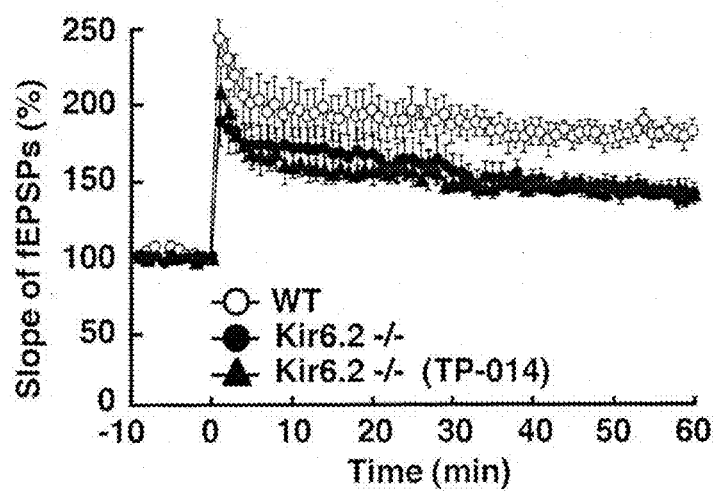
FIG. 8f shows the results of an experiment in which TP-014 was administered to Kir6.2 channel deficient mice for two months and analysis was made on long-term potentiation phenomenon (LTP) serving as an index of memory formation, by an electrophysiological technique.
Figure 8G:
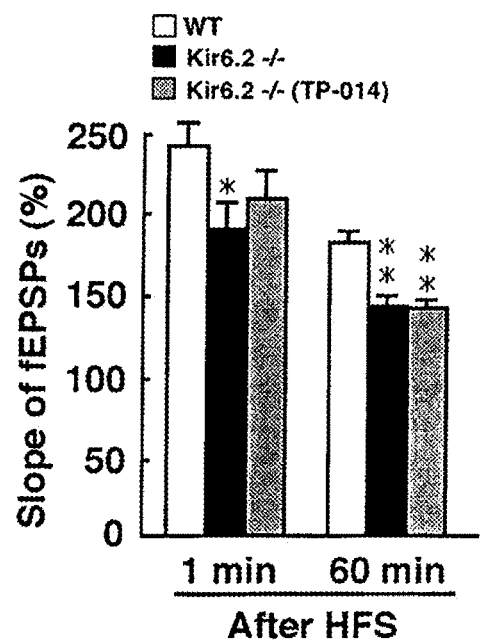
FIG. 8g shows the results of an experiment in which TP-014 was administered to Kir6.2 channel deficient mice for two months and analysis was made on long-term potentiation phenomenon (LTP) serving as an index of memory formation, by an electrophysiological technique. The case having a significant difference with WT is indicated by ** or *

To confirm that TP-014 action is Kir6.2 channel inhibitory action, the action site of TP-014 was identified by the same behavioral experiment as in FIG. 4 (FIG. 8a and FIG. 8b: Y-maze test, FIG. 8c: new object recognition test method, FIG. 8d: fear conditioning test method, FIG. 8e to FIG. 8g: LTP improvement evaluation, n=5 per group) using Kir6.2 channel deficient mice. The results are shown in FIG. 8. It was confirmed that cognitive dysfunction is induced in Kir6.2 defective mice. The results show that Kir6.2 channel is important for memory formation. It was also shown that memory disturbance and LTP attenuation of Kir6.2 defective mice are not improved by TP-014 chronic treatment (two months). The result shows that the action site of TP-014 is Kir6.2 channel. The analytical methods are the same as in Test Examples 4 to 7. Note that, Kir6.2 defective mice were obtained from Professor Susumu Seino, School of Medicine of Kobe University (Miki T et al., Proc. Natl. Acad. Sci. U.S.A. 1998, 95, 10402-10406).

Test Example 9

Figure 9A:
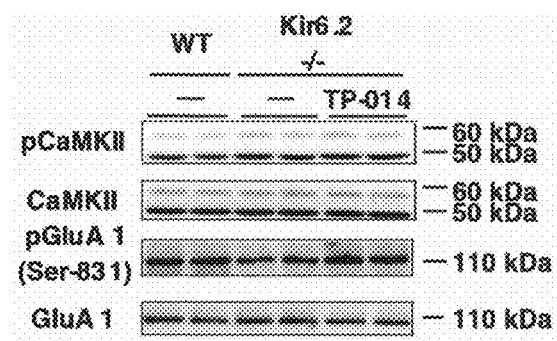
FIG. 9a shows bands (image) obtained by electrophoresis of immunoblots, showing the results of phosphorylation of proteins analyzed by immunoblotting using antibodies against CaMKII, CaMKIV and ERK.
Figure 9B:
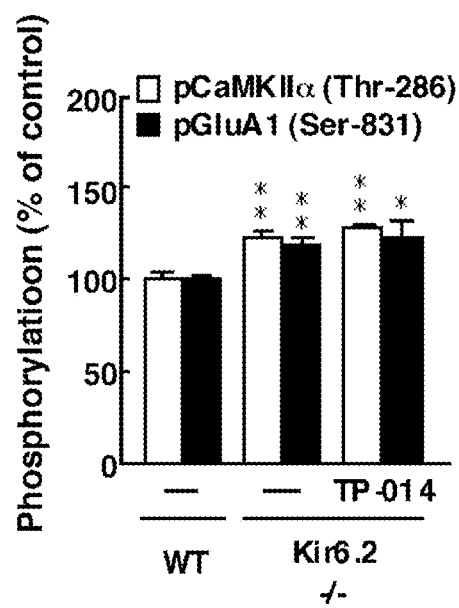
FIG. 9b shows the results of quantitative analysis of the signal intensity of the bands (in FIG. 9a) obtained by electrophoresis of immunoblots. The case having a significant difference with WT(−)(non-treated group with a drug) is indicated by ** or*.

Activation of CaMKII was investigated in the same manner as in FIGS. 4 to 7. In addition, GluA1 (Ser-831), which is known as a molecule activated by activation of CaMKII, was investigated. Hippocampal slices were suspended in an SDS sample buffer to prepare a suspension, which was subjected to immunoblotting. In this way, the intracellular mechanism of cognitive dysfunction in Kir6.2 defective mice was analyzed. The results are shown in FIG. 9 (FIG. 9a: band images by immunoblotting, FIG. 9b: quantification results of signal intensities of bands). In the hippocampus of Kir6.2 defective mice, activation of CaMKII was accelerated. Even in the case of chronic treatment with TP-014, no influence was observed. Abnormality was observed in intracellular and extracellular calcium homeostasis (balance) by a defect of Kir6.2 channel and phosphorylation of CaMKII was accelerated. It was demonstrated that TP-014 has no influence on activation of CaMKII, which suggests that an action site of TP-014 is Kir6.2 channel.

Test Example 10

Figure 10:
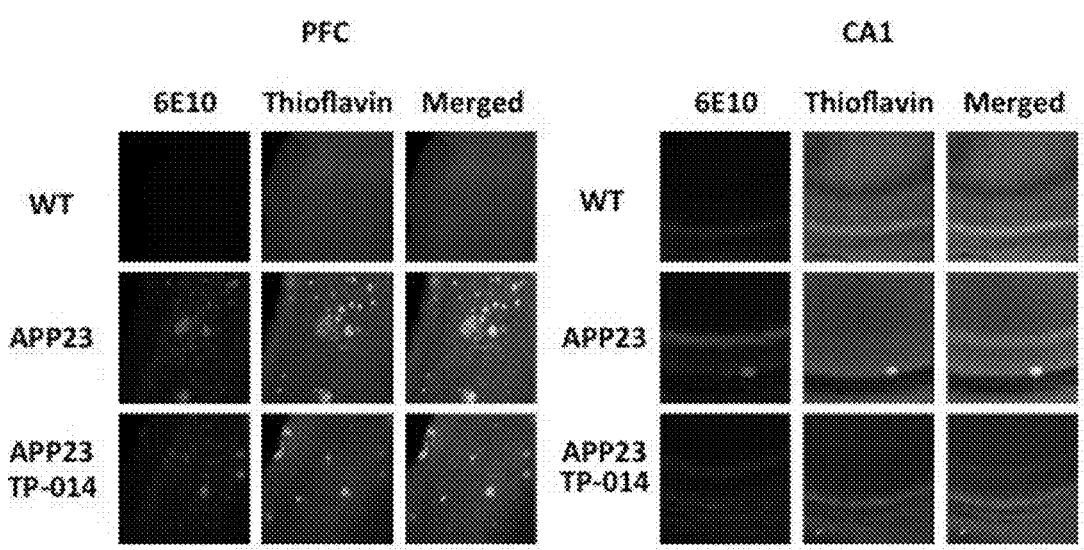
FIG. 10 shows staining results of brain slice sections of APP23 mouse, showing the effect of the compound of the present invention on Aβ aggregation.

The hypothesis that amyloid-β (Aβ) is a cause of Alzheimer's disease has now still important. AP aggregation, which occurs in APP23 mice (14 months old) was confirmed by immunostaining. The brains of a WT (control mouse) and APP23 mouse were cut into slice sections of 50 micrometers in thickness. The slice sections were stained with 6E10 (Aβ antibody, manufactured by Abcam) and thioflavin. The results (index for evaluating aggregates) are shown in FIG. 10. The conditions other than the above were the same as in the ordinary immunostaining method. It was found that Aβ aggregation was accelerated in the APP23 mouse, in particular, many aggregates were observed in the cerebral cortex (PFC). In contrast, aggregation was not virtually observed in the hippocampus (CA1). Aβ aggregation was inhibited by TP-014 chronic treatment. The result demonstrates that TP-014 has an inhibitory effect against Aβ aggregation.

Test Example 11

Figure 11A:
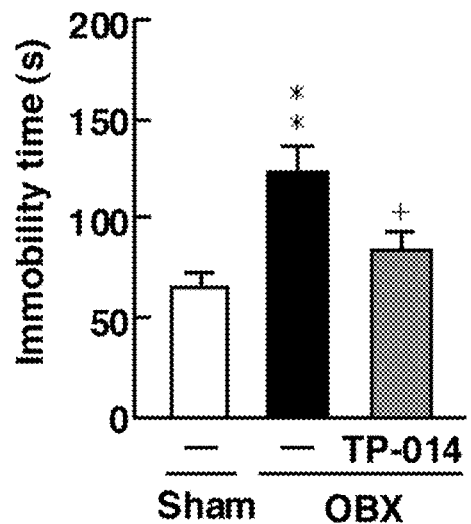
FIG. 11a shows the results of a test, which examined whether or not the compound of the present invention exerts an improvement effect on a depression-like symptom of OBX mice. The case having a significant difference with Sham (control group) is indicated by **; and the case having a significant difference with OBX mice is indicated by +.
Figure 11B:
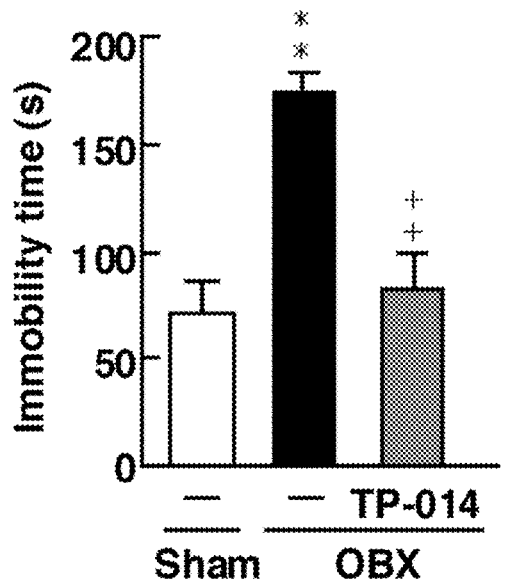
FIG. 11b shows the results of a test, which examined whether or not the compound of the present invention exerts an improvement effect on a depression-like symptom of OBX mice. The case having a significant difference with Sham (control group) is indicated by ** and the significant difference with OBX mice is indicated by +.

The improvement effect of TP-014 on a depression-like symptom was checked by using OBX mice as depression model mice. The results are shown in FIGS. 11a and 11b. OBX mice were originally established as depression model mice although a deterioration of cognitive function was observed. Depression was analyzed by a tail-suspension method (a) and a forced swim method (b). The tail-suspension method is a method of pinching the tail of a mouse and hanging the mouse upside down. If the mouse hung has depression, immobility time is long. Since a normal mouse moves even if it is hung, the immobility time is short. In the forced swim method, a mouse is forced to swim in water in a beaker. A mouse having depression neither swims nor moves (just floating). Thus the immobility time is measured. Immobility time was long in OBX mice both in the tail-suspension method (a) and the forced swim method (b). The immobility time of a TP-014 chronic administration group (2 weeks, in the same administration method as that previously mentioned) was improved. From the result, it was demonstrated that TP-014 has a depression-like symptom improving effect on OBX mice (n=5 per group).

Test Example 12

Figure 12A:
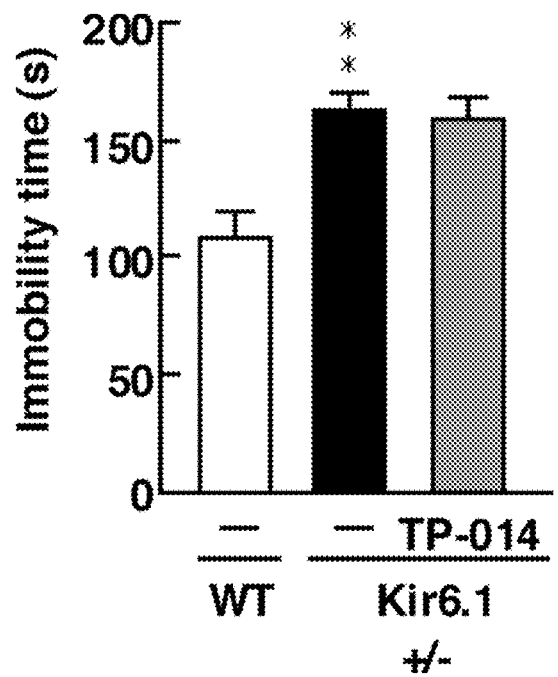
FIG. 12a shows the results of a test, which examined whether or not the compound of the present invention exerts an improvement effect on a depression through inhibitory action of the Kir6.1 channel. The case having a significant difference with WT (control group) is indicated by **.
Figure 12B:
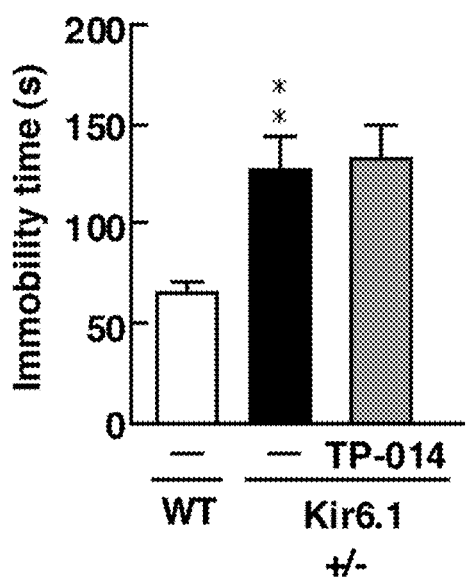
FIG. 12b shows the results of a test, which examined whether or not the compound of the present invention exerts an improvement effect on a depression through inhibitory action of the Kir6.1 channel. The case having a significant difference with WT (control group) is indicated by **.

Immobility time of Kir6.1 defective mice (hetero-type, n=5 per group) was measured by the tail-suspension method (a) and the forced swim method (b) in the same manner as in FIGS. 11a and 11b. The hetero-type mice are the mice in which the expression level of Kir6.1 channel is half (the homo type mice develops arrhythmia after birth and dies) in contrast to the homo type mice (complete defective mice). The results are shown in FIG. 12. The Kir6.1 defective mice showed a hyperactivated depression-like symptom. From the results, it was found that Kir6.1 is an important molecule for depression. The chronic treatment with TP-014 was not effective. It was confirmed that TP-014 produces depression-improvement effect through an inhibitory action of Kir6.1 channel. Kir6.1 defective mice were obtained from Professor Susumu Seino, School of Medicine of Kobe University (Miki T et al., Nature Medicine, 2002, 8, 466-472).

Test Example 13

Figure 13A:
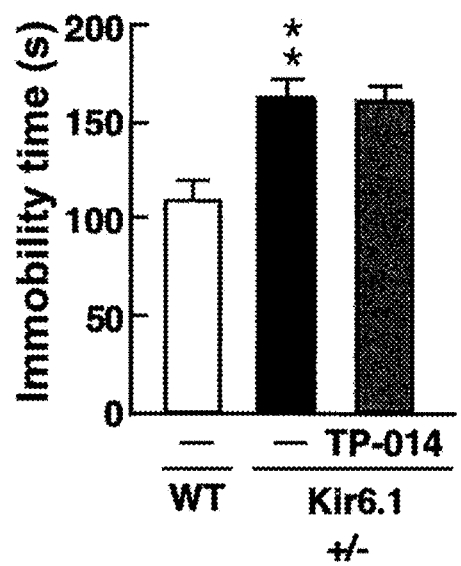
FIG. 13a shows the results of a test, which examined whether or not the compound of the present invention inhibits the Kir6.1 channel and activates CaMKIV, thereby exerting improvement effect on a depression. The case having a significant difference with WT (control group) is indicated by **.
Figure 13B:
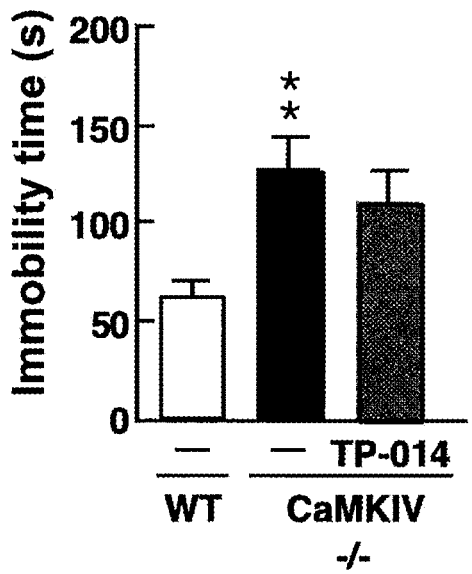
FIG. 13b shows the results of a test, which examined whether or not the compound of the present invention inhibits the Kir6.1 channel and activates CaMKIV, thereby exerting improvement effect on a depression-like symptom. The case having a significant difference with WT (control group) is indicated by **.

CaMKIV induced by Kir6.1 channel was analyzed by using CaMKIV defective mice (n=5, per group*) in the same manner as in FIG. 12. The results are shown in FIG. 13. Acceleration of depression-like symptom was observed also in the CaMKIV defective mice. From the result, it is found that CaMKIV is important for a mechanism of developing depression. TP-014 had no effect on CaMKIV depression-like symptom (increase of immobility time). It was found that TP-014 inhibits Kir6.1 channel and exerts a depression improvement effect through activation of CaMKIV. CaMKIV defective mice were obtained from professor, Hiroyuki Sakagami, Kitasato University School of Medicine (Takao K et al., PLoS One 2010, 5, e9460).

Test Example 14

Figure 14:
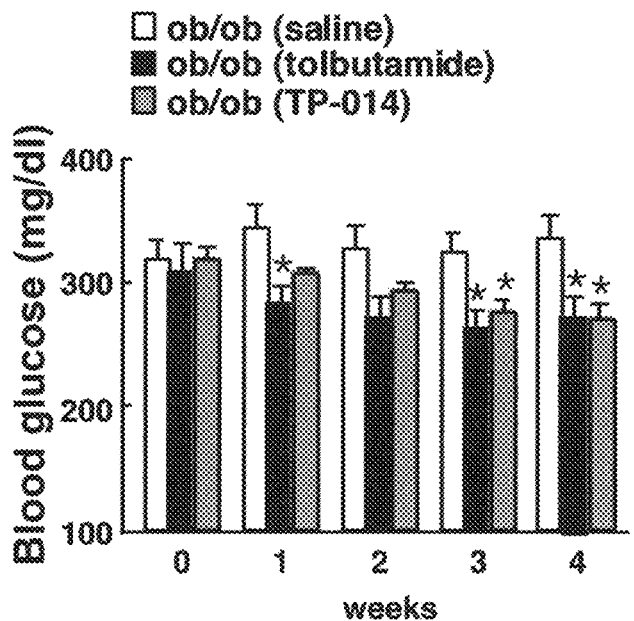
FIG. 14 shows the results of a test, which examined whether or not the compound of the present invention has a hypoglycemic effect. The term "weeks" refers to the time period of chronic administration, the case having a significant difference between ob/ob (saline) in each week is indicated by *.
Figure 15:
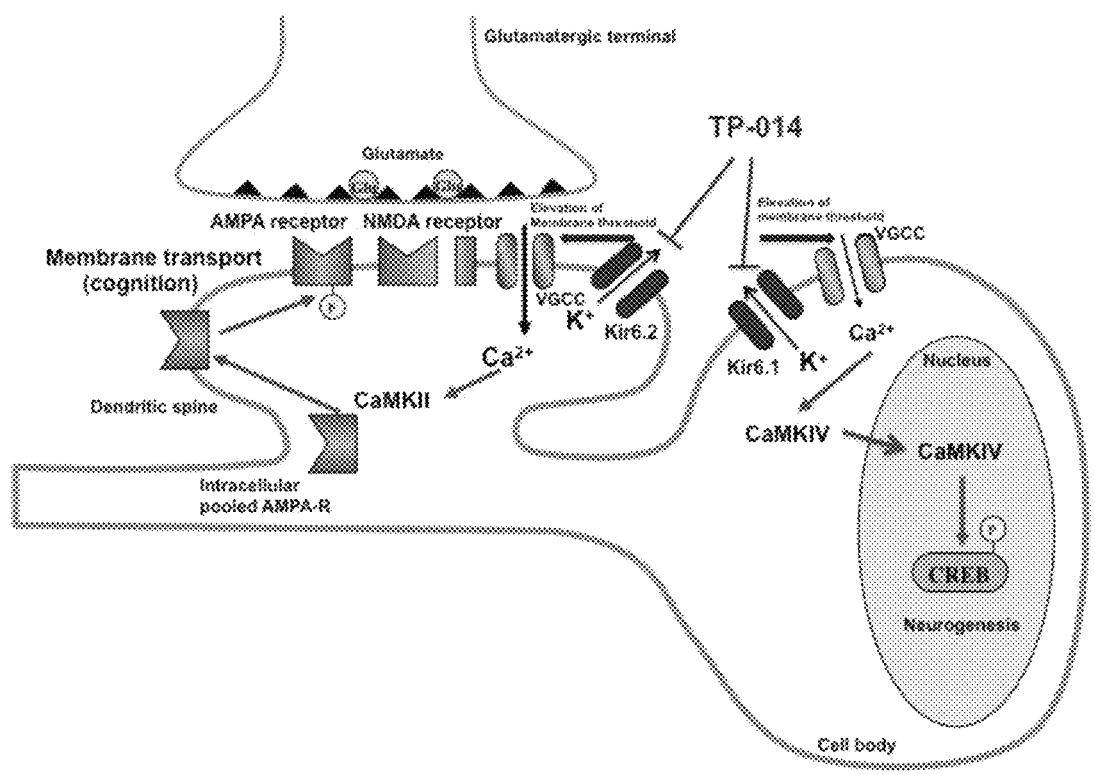
FIG. 15 shows an illustration showing the action mechanism of TP-014. When the Kir6.2 channel localized in the spine is inhibited, potassium present within cells cannot flow out, increasing the threshold of cell membrane. As a result, calcium outside cells is accelerated to flow into the cells, activates CaMKII, activates GluA1 (Ser-831)(AMPA acceptor) downstream of CaMKII and presumably improves cognitive function. TP-014 similarly inhibits the Kir6.1 channel localizing in the nerve cell body. As a result, calcium flows into cells in the similar mechanism. Calcium influx activates CaMKIV, activates CREB (Ser-133) and presumably induces neurogenesis to improve depression. TP-014 is a novel cognitive function improving drug having both a cognitive function improvement effect (core symptom of Alzheimer's disease) based on a Kir6.2 channel inhibitory action and a depression improvement effect (peripheral symptom of Alzheimer's disease) based on a Kir6.1 channel inhibitory action.
Figure 16:
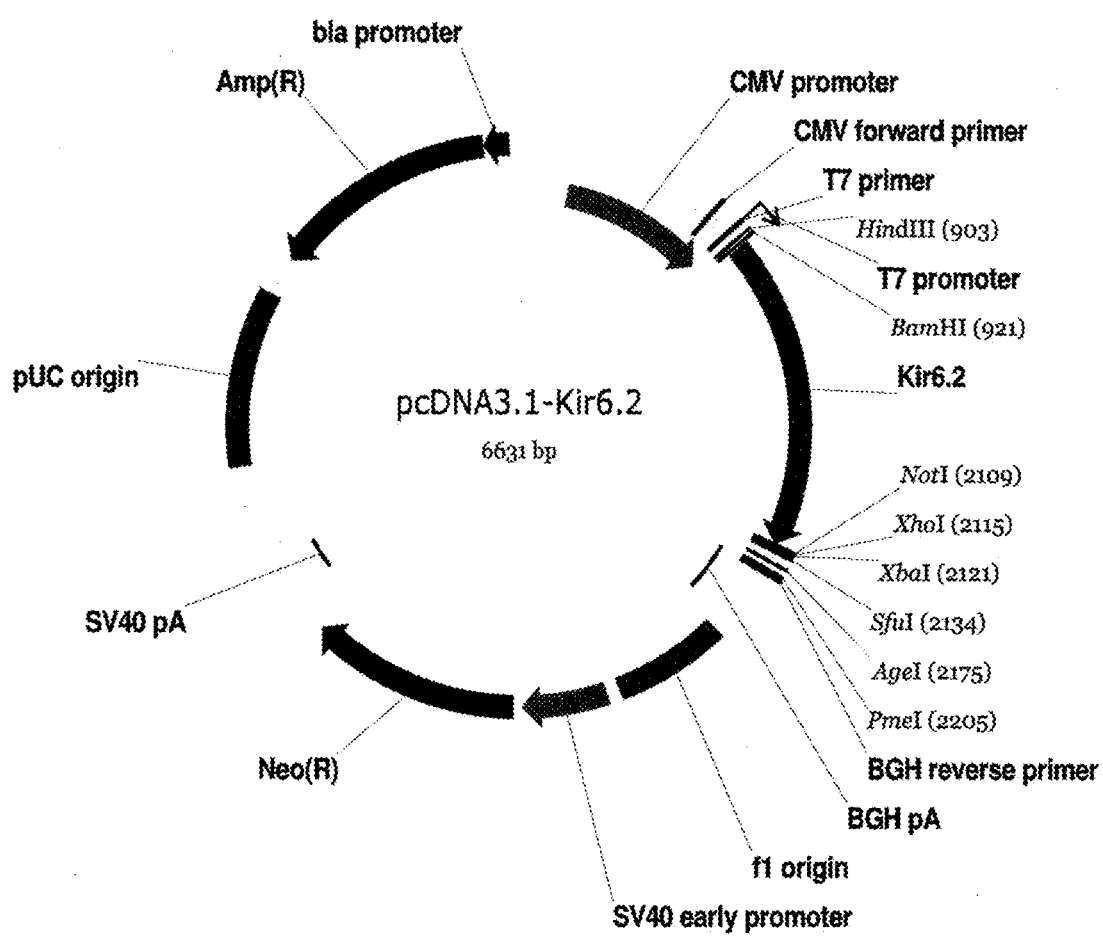
FIG. 16 shows the structure of a plasmid vector: pcDNA3.1-Kir6.2.

A hypoglycemic effect by TP-014 was checked by measuring the blood glucose level by an assay kit (manufactured by Technicon International co). The results are shown in FIG. 14. The measurement was carried out for 4 weeks. As a result that chronic treatment with TP-014 (1 mg/kg) was carried out for 4 weeks, blood glucose level significantly decreased on and after 3 weeks. As a control, tolbutamide was used. Kir6.2 channel binds to SUR1 (urea receptor) on the cell membrane to form a channel. Action mechanism is considered due to Kir6.2 channel inhibitory action. Tolbutamide binds to SUR1 to inhibit Kir6.2 channel.

Test Example 15

A plasmid vector having cDNA of Kir6.1 channel inserted therein: pcDNA3.1-Kir6.1, was obtained from professor Toru Ishizuka of Graduate School of Life Sciences, Tohoku University. N2A cells overexpressing Kir6.1 channel were obtained in the same manner as in "preparation of N2A cells overexpressing Kir6.2 channel" of Test Example 1 except that the above plasmid was used.

Activation of CaMKIV was analyzed (measured) by using Kir6.1 channel-overexpressing cells obtained. The same immunoblotting as in Test Example 1 was employed as the analysis method. As the primary antibody, an anti-phosphorylated CaMKIV antibody (Kasahara J et al., J. Biol. Chem. 2001, 276, 24044-50) was used. As the secondary antibody, an anti-rabbit IgG antibody (manufactured by SouthernBiotech) was used.

Figure 18A:
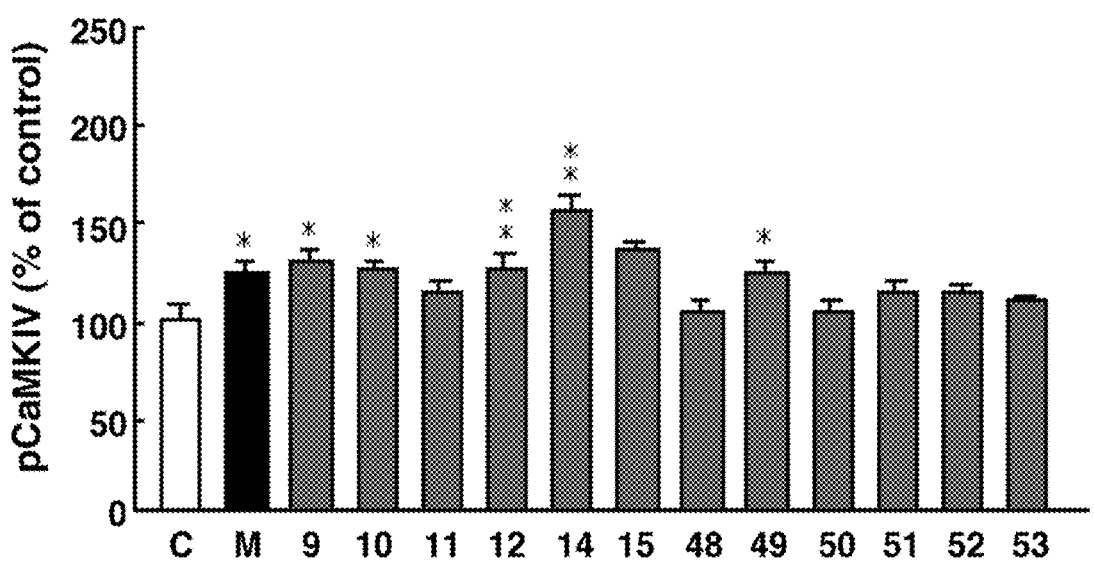
FIG. 18a is a graph showing CaMKIV activity enhanced by the compound of the present invention in cells (Neuro2A cells) overexpressing Kir6.1 channel. All cases having a significant difference with a control (C: Kir6.1 expressing cells not treated with a drug) are marked.
Figure 18B:
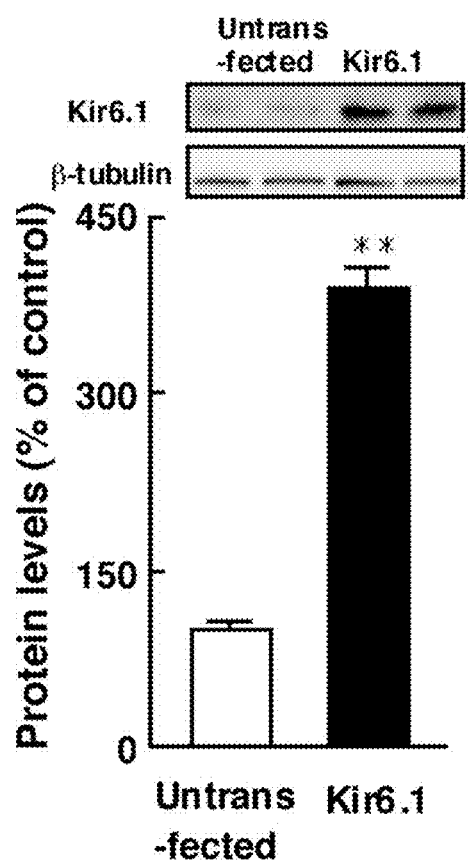
FIG. 18b shows the results of expression of Kir6.1 channel in N2A cells, which is checked by applying immunoblotting using an anti-Kir6.1 channel antibody to Kir6.1 channel-overexpressing cells. The case having a significant difference with a non-drug treatment group (−) is indicated by **.
Figure 18C:
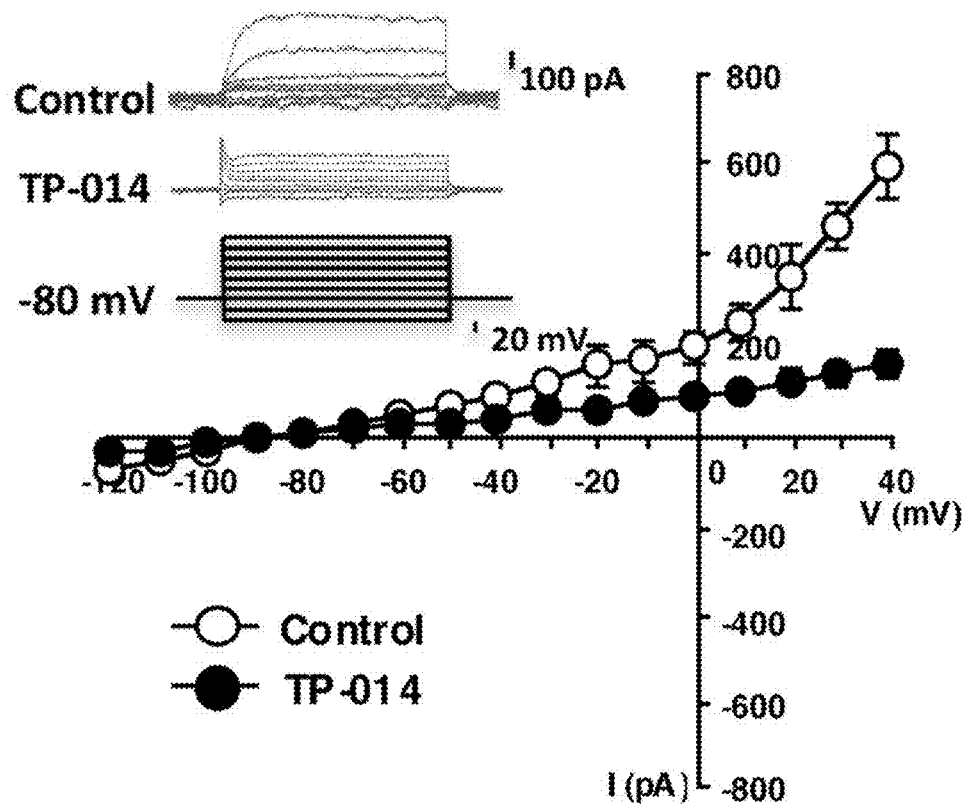
FIG. 18c shows the results of potassium current flowing out from cells outside the cells checked by using Kir6.1 channel-overexpressing cells and measured by an ordinary patch-clamp method.

Using Kir6.1 channel-overexpressing cells obtained, potassium current flowing outside from cells was measured by the ordinary patch-clamp method. The results are shown in FIG. 18. ATP-sensitive potassium channel (Kir6.1 channel) was localized in the cell membrane of the nerve cells. If the channel is inhibited and clogged, the threshold of the nerve cell membrane rises to produce the analogous state as where an action potential is temporarily generated, with the result that potassium current flows out from cells outside and, in place, calcium current flows into the cells from outside. FIG. 18a shows that Kir6.1 channel is overexpressed in N2A cells (the upper figure shows stained images by immunoblotting; whereas the lower figure quantitatively expresses the signal intensity of bands). This was confirmed by applying immunoblotting (the same conditions as in Test Example 1 were employed except that anti-Kir6.1 channel antibody, n=5) with an anti-Kir6.1 channel antibody (prepared based on an ordinary method) to Kir6.1 channel-overexpressing cells (prepared by the aforementioned method). No change was observed in a housekeeping gene, i.e., β-tubulin (an anti-β-tubulin antibody was obtained from Sigma-Aldrich. Other conditions are the same as those in detection of Kir6.1). FIG. 18b shows that if Kir6.2 channel-overexpressing cells are allowed to stand still in an electrophysiological experimental buffer containing TP-014 so as to obtain a concentration of 10 nM, potassium current, which outwardly flows when the membrane potential of nerve cells is changed toward a plus side, is suppressed (n=5 per group). The results show that TP-014 inhibits Kir6.1 channel and inhibits potassium current flowing outside from the cells.

Test Example 16

Using WT mice (C57BL/6J, Japan SLC, two months old) administered with corticosterone (dose of 5 mg/kg was administered once a day for 2 weeks); and Kir6.1 defective mice administered with corticosterone, as disease model mice showing anxiety-like symptoms, five behavioral tests regarding anxiety-related behavior were conducted. Note that, the Kir6.1 defective mice were obtained from Professor Susumu Seino, School of Medicine of Kobe University (Miki T et al., Nature Medicine 2002, 8, 466-472).

To the WT mice and Kir6.1 defective mice administered with corticosterone, TP-014 (1 mg/kg) was administered via the oral route once a day for 2 weeks (chronic treatment). As a result, it was confirmed that a significant anxiety symptom acceleration improving effect was obtained. The results are shown in FIG. 19.

Figure 19A:
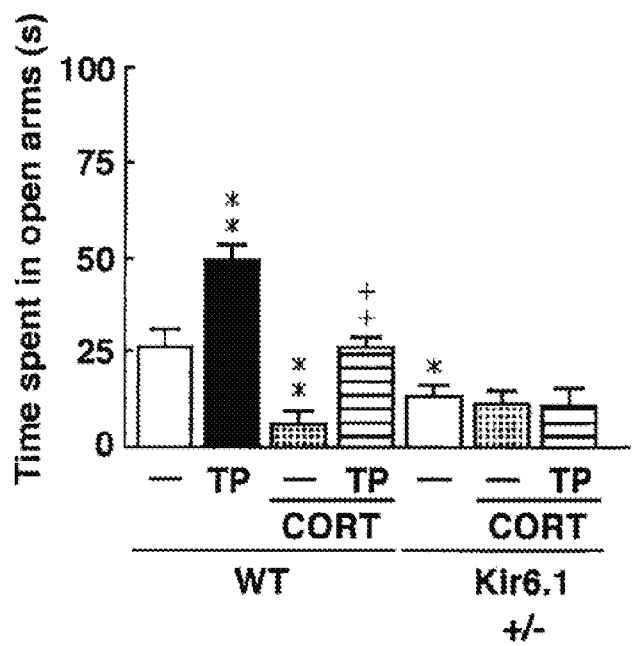
FIG. 19a shows results on vulnerability of mice groups (used in a test) to anxiety, analyzed by the elevated plus-maze method. With respect to the retention time of mice on the open arm, the case having a significant difference with WT(−) is indicated by ** or *; and the case having a significant difference with WT (CORT) is indicated by ++.
Figure 19B:
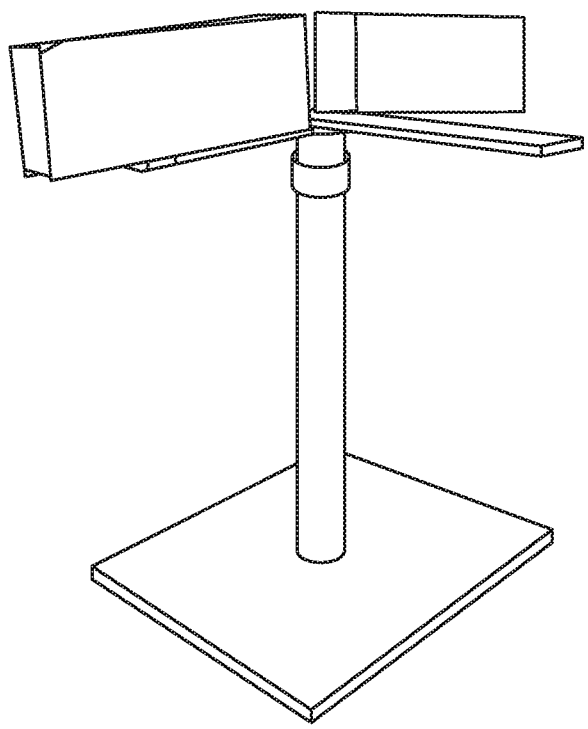
FIG. 19b shows a photograph of the apparatus used in the elevated plus-maze method.

FIG. 19a shows the results of vulnerability of each group (n=5 per group) to anxiety analyzed by elevated plus-maze method (FIG. 19b). In the apparatus used herein, plus-shaped apparatus with arms is provided at a high place and individual arms are either open (visible) or enclosed. Mice vulnerable to anxiety stay for a long time in the enclosed arm; whereas mice resistant to anxiety stay in the open arm (visible). The retention time on the open arm is indicated on the vertical axis of FIG. 19a.

Figure 19C:
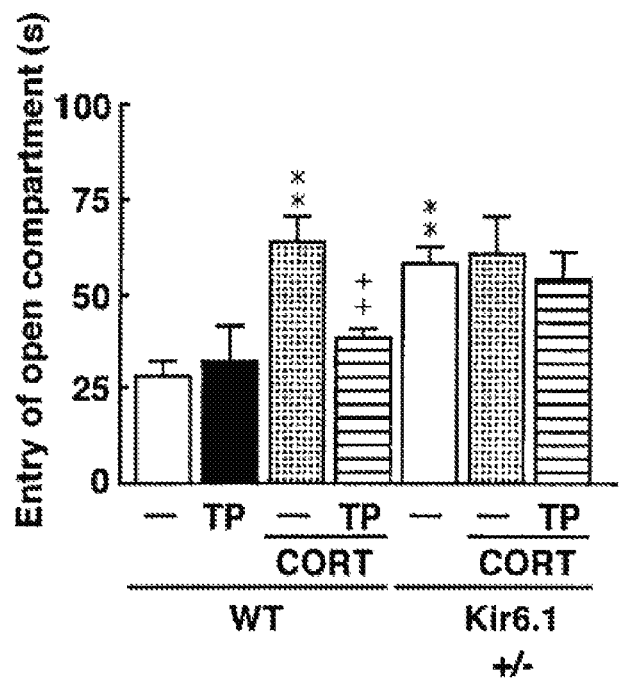
FIG. 19c shows the results of the light/dark test method. The case having a significant difference with WT(−) is indicated by **; and the case having a significant difference with WT (CORT) is indicated by ++.
Figure 19D:
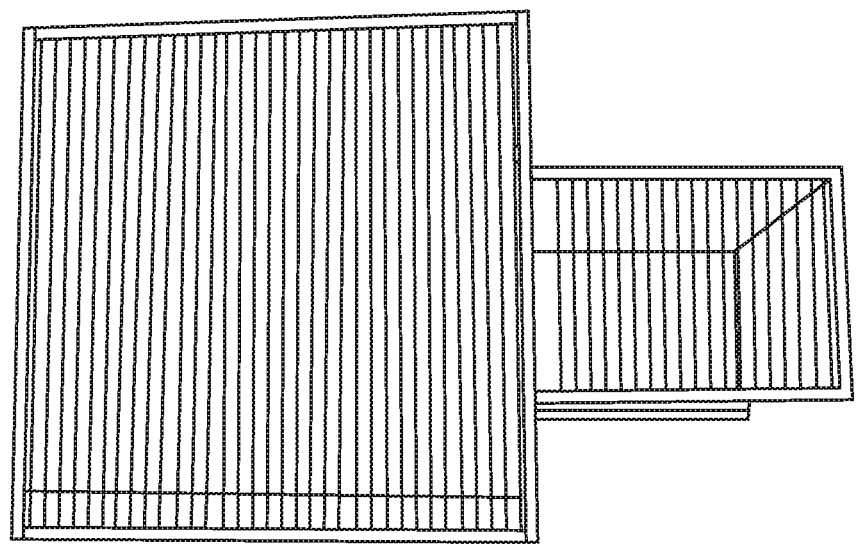
FIG. 19d shows a photograph of the apparatus used in the light/dark test method.

FIG. 19c shows the results by a light/dark test method (FIG. 19d) (n=5 per group). The time until a mouse placed in a black box (dark place) feels anxiety to light and comes out of the box to a bright place) was measured. The time until a mouse comes out (entry of open compartment) is indicated in the vertical axis of FIG. 19c.

Figure 19E:
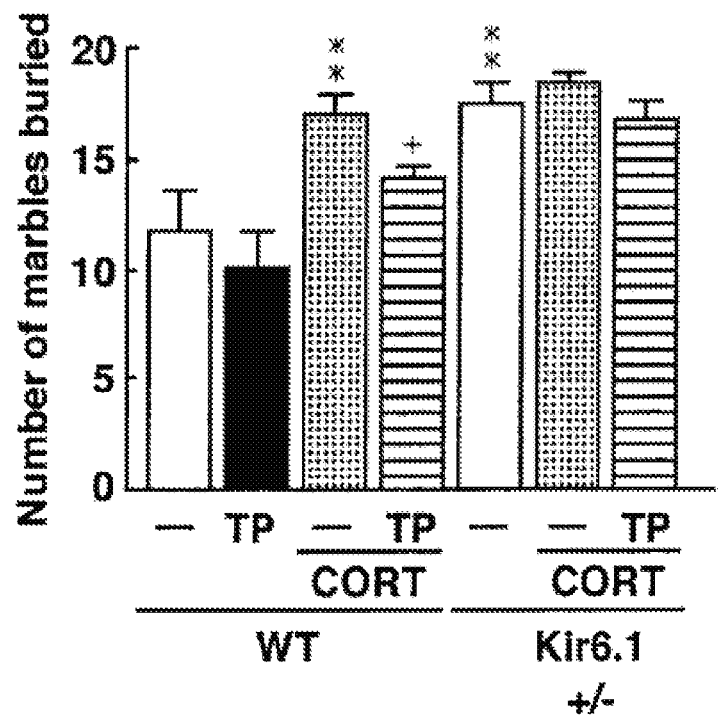
FIG. 19e shows the test results of the marble burying method. The case having a significant difference with WT(−) is indicated by **; and the case having a significant difference with WT (CORT) is indicated by +.
Figure 19F:
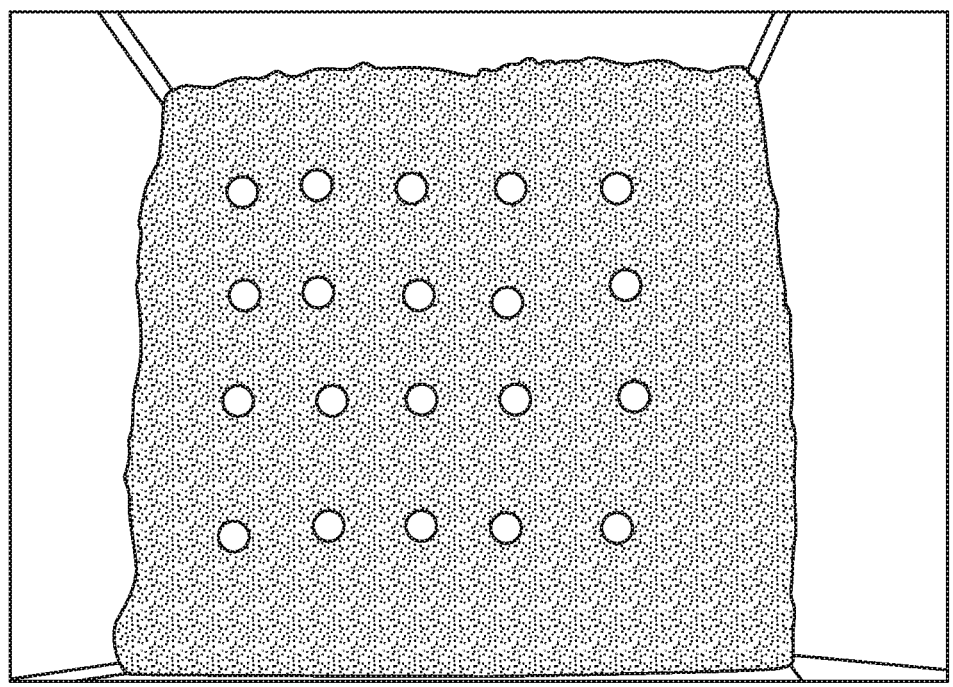
FIG. 19f shows a photograph of the apparatus used in the marble burying method.

FIG. 19e shows the results of a marble burying method, (FIG. 19f) (n=5 per group). In the cage for housing a mouse is filled with wood chip bedding and 20 marbles are placed such that a mouse can see them. A mouse is allowed to freely move for 30 minutes. The number of marbles buried and hidden in the wood chip bedding is counted. Since a mouse does not like a glowing object, mice resistant to anxiety come to be in contact with many marbles. The number of marbles buried is indicated on the vertical axis of FIG. 19e.

Figure 19G:
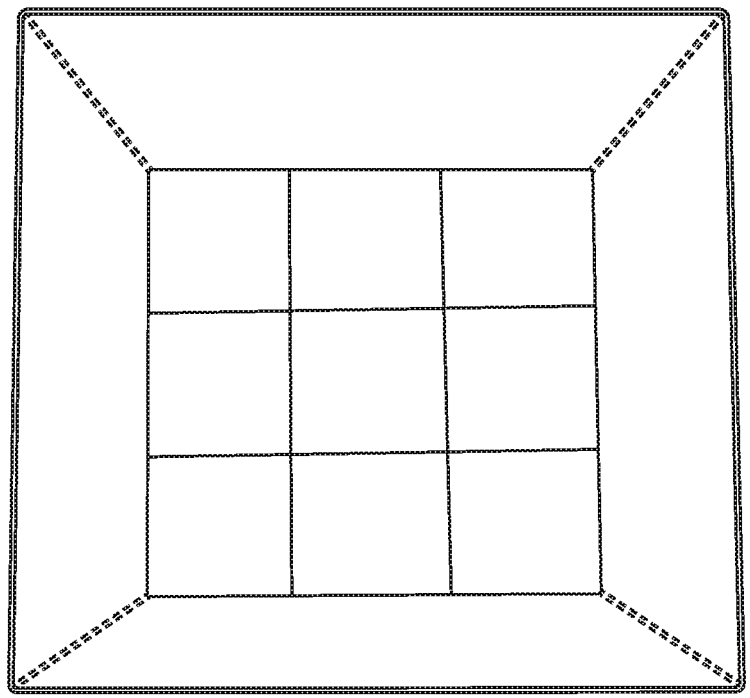
FIG. 19g shows test results of the open field method. The case having a significant difference with WT(−) is indicated by **; and the case having a significant difference with WT (CORT) is indicated by ++.
Figure 19H:
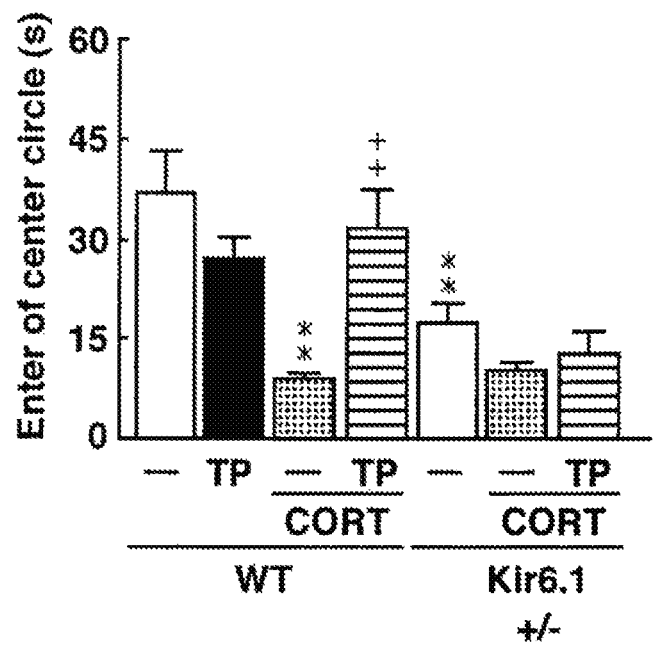
FIG. 19h shows a photograph of the apparatus used in the open field method.

FIG. 19g shows the test results by an open field method (FIG. 19h) (n=5 per group). A mouse is placed in a square box and allowed to move for 30 minutes within the box. Usually, a mouse which feels strong anxiety tends to walk along the edge of the box; whereas a mouse having strong resistance to anxiety frequently walks in the center portion of the box. Such a tendency is used as a reference. The time of staying in the center portion of the box is indicated in FIG. 19h.

Figure 19I:
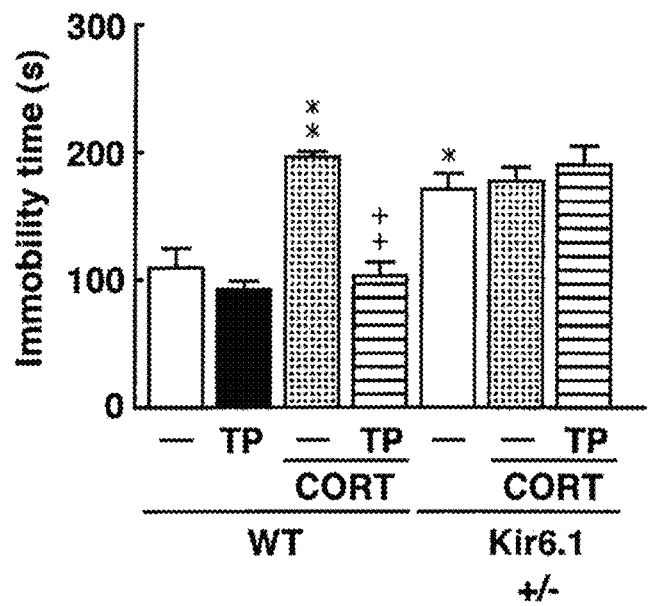
FIG. 19i test results of the fear conditioning test method. The case having a significant difference with WT(−) is indicated by ** or *; and the case having a significant difference with WT (CORT) is indicated by ++.
Figure 20:
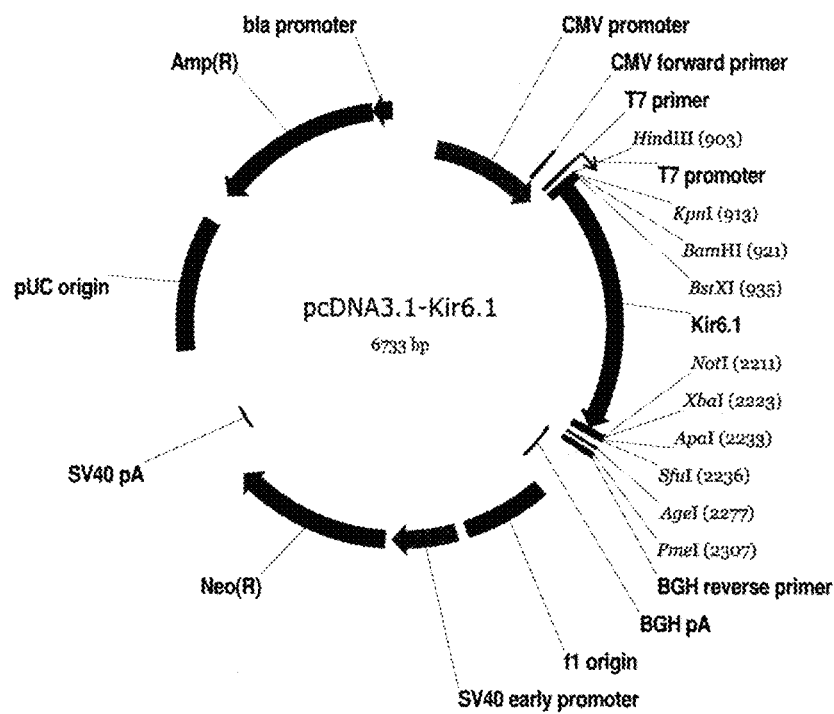
FIG. 20 shows the structure of a plasmid vector: pcDNA3.1-Kir6.1.

FIG. 19i shows the results of a test performed in accordance with a fear conditioning method (n=5 per group). Using the same test apparatus as in the light/dark test method, a mouse is placed in a dark place, and then, sound (treble) is produced for 30 seconds and thereafter electrical stimulation is given for 3 seconds. After the sound, electrical stimulation is repeatedly given three times. If so, the mouse learns that electrical stimulation will be given after the sound. On the following day, sound is kept ringing for 5 minutes. A mouse if it felt fear/anxiety, does not move. The immobility time of the mouse is measured. The immobility time is indicated on the vertical axis of FIG. 19i.

In all above test results, it was confirmed that chronic administration (2 weeks) with TP-014 improve acceleration of anxiety-like symptom. Kir6.1 defective mice administered with corticosterone exhibit anxiety-like symptoms; however, no improvement effect was obtained by administration of TP-014. From the results, it was confirmed that the improvement effect of the compound of the present invention on acceleration of anxiety-like symptom is exerted by way of Kir6.1.

Note that, in the drawings of this application, indications of significant difference, ** or ++ represent P<0.01; whereas indications of significant difference, + or * represent P<0.05.

The invention claimed is:
1. A compound represented by Formula (I):

[Chemical Formula 1]

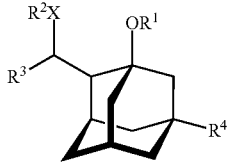

(I)

wherein R$^1$ represents a hydrogen atom or (C$_{1-6}$ alkyl)carbonyl optionally substituted with one or more halogen atoms;
R$^2$ represents a hydrogen atom or (C$_{1-6}$ alkyl)carbonyl optionally substituted with one or more halogen atoms;
X represents O or NR$^5$;
R$^3$ represents phenyl optionally substituted with one or more substituents selected from X$^1$, 5- or 6-membered heteroaryl optionally substituted with one or more substituents selected from X$^1$, or COOR$^6$;
R$^4$ represents a hydrogen atom, a halogen atom, azido, —OR$^7$ or —NHR$^8$;
R$^5$ represents a hydrogen atom or C$_{1-6}$ alkyl;
R$^6$ represents a hydrogen atom or C$_{1-6}$ alkyl;
R$^7$ represents a hydrogen atom, C$_{1-6}$ alkyl, C$_{1-6}$ alkoxy-C$_{1-6}$ alkyl or (C$_{1-6}$ alkyl)carbonyl optionally substituted with one or more halogen atoms;
R$^8$ represents a hydrogen atom, C$_{1-6}$ alkyl or (C$_{1-6}$ alkyl)carbonyl optionally substituted with one or more halogen atoms; and
X$^1$ represents C$_{1-6}$ alkyl, a halogen atom, C$_{1-6}$ alkoxy, nitro or cyano,
an enantiomer thereof, a diastereomer thereof, or a pharmaceutically acceptable salt thereof.

2. The compound, an enantiomer thereof, a diastereomer thereof, or a pharmaceutically acceptable salt thereof according to claim 1, wherein R$^4$ represents a chlorine atom or azido.

3. The compound, an enantiomer thereof, a diastereomer thereof, or a pharmaceutically acceptable salt thereof according to claim 1, wherein R$^1$ represents trifluoroacetyl.

4. The compound, an enantiomer thereof, a diastereomer thereof, or a pharmaceutically acceptable salt thereof according to claim 1, wherein R$^2$ represents (C$_{1-6}$ alkyl)carbonyl optionally substituted with one or more halogen atoms.

5. The compound, an enantiomer thereof, a diastereomer thereof, or a pharmaceutically acceptable salt thereof according to claim 4, wherein R$^2$ represents trifluoroacetyl.

6. The compound, an enantiomer thereof, a diastereomer thereof, or a pharmaceutically acceptable salt thereof according to claim 1, wherein R$^3$ represents phenyl optionally substituted with one or more substituents selected from X$^1$ or pyridyl optionally substituted with one or more substituents selected from X$^1$.

7. The compound, an enantiomer thereof, a diastereomer thereof, or a pharmaceutically acceptable salt thereof according to claim 1, selected from
(R)-((1R,2S,3R,5R,7S)-5-azido-1-hydroxyadamantan-2-yl)(phenyl)methyl acetate;
ethyl (S)-2-acetamido-2-((1R,2S,3R,5R,7R)-5-chloro-1-hydroxyadamantan-2-yl)acetate;
ethyl (R)-2-acetamido-2-((1R,2S,3R,5R,7R)-5-chloro-1-hydroxyadamantan-2-yl)acetate;
(1R,2S,3R,5R,7R)-5-chloro-2-((S)-2-methoxy-2-oxo-1-(2,2,2-trifluoroacetamido)ethyl)adamantan-1-yl 2,2,2-trifluoroacetate;
(1S,2R,3S,5S,7S)-5-chloro-2-((R)-phenyl(2,2,2-trifluoroacetamido)methyl)adamantan-1-yl 2,2,2-trifluoroacetate;
(S)-2-amino-2-((1R,2S,3R,5R,7S)-1,5-dihydroxyadamantan-2-yl)acetic acid;
N—((R)-((1S,2R,3S,5S,7S)-5-chloro-1-hydroxyadamantan-2-yl)(phenyl)methyl)-2,2,2-trifluoroacetamide;
(1S,2R,3S,5R,7S)-2-((R)-phenyl(2,2,2-trifluoroacetamido)methyl)adamantan-1-yl 2,2,2-trifluoroacetate;
(1S,2R,3S,5S,7R)-5-(2-methoxyethoxy)-2-((R)-phenyl(2,2,2-trifluoroacetamido)methyl)adamantan-1-yl 2,2,2-trifluoroacetate;
N—((R)-((1S,2R,3S,5S,7S)-5-chloro-1-hydroxyadamantan-2-yl)(pyridin-3-yl)methyl)-2,2,2-trifluoroacetamide;
2,2,2-trifluoro-N—((R)-((1S,2R,3S,5R,7S)-1-hydroxyadamantan-2-yl)(phenyl)methyl)acetamide; and
(1S,2R,3S,5S,7R)-5-methoxy-2-((R)-phenyl(2,2,2-trifluoroacetamido)methyl)adamantan-1-yl 2,2,2-trifluoroacetate,
or an enantiomer thereof, a diastereomer thereof, or a pharmaceutically acceptable salt thereof.

8. A pharmaceutical composition containing the compound, an enantiomer thereof, a diastereomer thereof, or a pharmaceutically acceptable salt thereof according to claim 1.

9. The pharmaceutical composition according to claim 8, for use in treating or preventing a cognitive disease or disorder.

10. The pharmaceutical composition according to claim 9, wherein the cognitive disease or disorder is selected from Alzheimer's dementia, cerebrovascular dementia, Lewy body dementia, frontotemporal dementia, Parkinson's disease, a mental disease and a neurodegenerative disease.

11. The pharmaceutical composition according to claim 8, for use in treating or preventing diabetes or a diabetic complication.

12. A Kir6.2 channel inhibitor containing the compound, an enantiomer thereof, a diastereomer thereof, or a pharmaceutically acceptable salt thereof according to claim 1.

13. The Kir6.1 channel inhibitor containing the compound, an enantiomer thereof, a diastereomer thereof, or a pharmaceutically acceptable salt thereof according to claim 1.

* * * * *

SEQUENCE LISTING

<160> NUMBER OF SEQ ID NOS: 2

<210> SEQ ID NO 1

<211> LENGTH: 6631
<212> TYPE: DNA
<213> ORGANISM: Artificial Sequence
<220> FEATURE:
<223> OTHER INFORMATION: vector

<400> SEQUENCE: 1

| | |
|---|---|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagt | 900 |
| taagcttggt accgagctcg gatccgccac catgctgtcc gaaagggca ttatccctga | 960 |
| ggaatatgtg ctgacccggc tggcagagga ccctacagag cccaggtacc gtactcggga | 1020 |
| gaggagggcc cgcttcgtgt ccaagaaagg caactgcaac gtcgcccaca gaacatccg | 1080 |
| agagcagggc cgcttcctgc aagatgtgtt caccacgctg gtggacctca gtgcccca | 1140 |
| cacgctgctc atttttcacca tgtccttcct gtgcagctgg ctgctcttcg ccatggtctg | 1200 |
| gtggctcatc gcctttgccc acggtgactt ggccccgga gagggcacca atgtgccctg | 1260 |
| cgtcacaagc atccactcct tttcgtctgc cttccttttc tccatcgagg tccaggtgac | 1320 |
| cattggtttc ggcgggcgca tggtgacaga ggaatgtccc ctggccatcc ttattctgat | 1380 |
| cgtgcagaat atcgtagggc taatgatcaa cgccatcatg ctgggctgca tcttcatgaa | 1440 |
| aacggcacag gccatcggc gggcagaaac cctcatcttc agcaagcatg ccgtgatcac | 1500 |
| cctgcgacat ggccgcctgt gcttcatgct tcgcgtaggg gacctccgaa aaagcatgat | 1560 |
| cattagcgcc accattcata tgcaggtggt gcgcaagacc accagcccgg agggcgaggt | 1620 |
| tgtgcctctc caccaggtgg acatccccat ggagaacggt gtgggtggta acagcatctt | 1680 |
| tctggtggcc ccactcatca tctaccacgt catcgactcc aacagcccgc tctacgacct | 1740 |
| ggctcctagt gacctgcacc accaccagga cctggagatc attgtcatct ggaaggtgt | 1800 |
| ggtagaaacc acaggcatta ccacccaggc ccgcacctcc tatctggctg acgagattct | 1860 |
| gtggggggcag cgttttgtcc ccatcgtggc cgaggaggat ggccgctatt ctgtggacta | 1920 |
| ctccaaattc gggaacaccg ttaaagtgcc cacaccactc tgcacagccc gccagcttga | 1980 |
| tgaggaccgc agcctgctgg atgccctgac cctcgcctcg tcgcgagggc ccctgcgcaa | 2040 |
| gcgcagtgtg gctgtggcaa aggccaagcc caagtttagc atctctccgg attccttgtc | 2100 |
| ctgatagcgg ccgctcgagt ctagagggcc cttcgaacaa aaactcatct cagaagagga | 2160 |

```
tctgaatatg cataccggtc atcatcacca tcaccattga gtttaaaccc gctgatcagc    2220
ctcgactgtg ccttctagtt gccagccatc tgttgtttgc ccctcccccg tgccttcctt    2280
gaccctggaa ggtgccactc ccactgtcct ttcctaataa aatgaggaaa ttgcatcgca    2340
ttgtctgagt aggtgtcatt ctattctggg ggtgggggtg gggcaggaca gcaaggggga    2400
ggattgggaa gacaatagca ggcatgctgg ggatgcggtg ggctctatgg cttctgaggc    2460
ggaaagaacc agctggggct ctaggggta tccccacgcg ccctgtagcg gcgcattaag    2520
cgcggcgggt gtggtggtta cgcgcagcgt gaccgctaca cttgccagcg ccctagcgcc    2580
cgctcctttc gctttcttcc cttcctttct cgccacgttc gccggctttc ccgtcaagc    2640 tctaaatcgg gggctccctt tagggttccg atttagtgct ttacggcacc tcgaccccaa    2700
aaaacttgat tagggtgatg gttcacgtag tgggccatcg ccctgataga cggttttcg    2760 ccctttgacg ttggagtcca cgttctttaa tagtggactc ttgttccaaa ctggaacaac    2820
actcaaccct atctcggtct attcttttga tttataaggg attttgccga tttcggccta    2880
ttggttaaaa aatgagctga tttaacaaaa atttaacgcg aattaattct gtggaatgtg    2940
tgtcagttag ggtgtggaaa gtccccaggc tccccagcag gcagaagtat gcaaagcatg    3000
catctcaatt agtcagcaac caggtgtgga aagtccccag gctccccagc aggcagaagt    3060
atgcaaagca tgcatctcaa ttagtcagca accatagtcc cgcccctaac tccgcccatc    3120
ccgcccctaa ctccgcccag ttccgcccat tctccgcccc atggctgact aatttttttt    3180
atttatgcag aggccgaggc cgcctctgcc tctgagctat tccagaagta gtgaggaggc    3240
ttttttggag gcctaggctt ttgcaaaaag ctcccgggag cttgtatatc cattttcgga    3300
tctgatcaag agacaggatg aggatcgttt cgcatgattg aacaagatgg attgcacgca    3360
ggttctccgg ccgcttgggt ggagaggcta ttcggctatg actgggcaca acagacaatc    3420
ggctgctctg atgccgccgt gttccggctg tcagcgcagg ggcgcccggt tctttttgtc    3480
aagaccgacc tgtccggtgc cctgaatgaa ctgcaggacg aggcagcgcg gctatcgtgg    3540
ctggccacga cgggcgttcc ttgcgcagct gtgctcgacg ttgtcactga agcgggaagg    3600
gactggctgc tattgggcga agtgccgggg caggatctcc tgtcatctca ccttgctcct    3660
gccgagaaag tatccatcat ggctgatgca atgcggcggc tgcatacgct tgatccggct    3720
acctgcccat tcgaccacca agcgaaacat cgcatcgagc gagcacgtac tcggatggaa    3780
gccggtcttg tcgatcagga tgatctggac gaagagcatc aggggctcgc gccagccgaa    3840
ctgttcgcca ggctcaaggc gcgcatgccc gacggcgagg atctcgtcgt gacccatggc    3900
gatgcctgct tgccgaatat catggtggaa aatggccgct tttctggatt catcgactgt    3960
ggccggctgg gtgtggcgga ccgctatcag gacatagcgt tggctacccg tgatattgct    4020
gaagagcttg gcggcgaatg ggctgaccgc ttcctcgtgc tttacggtat cgccgctccc    4080
gattcgcagc gcatcgcctt ctatcgcctt cttgacgagt tcttctgagc gggactctgg    4140
ggttcgcgaa atgaccgacc aagcgacgcc caacctgcca tcacgagatt tcgattccac    4200
cgccgccttc tatgaaaggt tgggcttcgg aatcgttttc cgggacgccg gctggatgat    4260
cctccagcgc ggggatctca tgctggagtt cttcgcccac cccaacttgt ttattgcagc    4320
ttataatggt tacaaataaa gcaatagcat cacaaatttc acaaataaag cattttttc    4380 actgcattct agttgtggtt tgtccaaact catcaatgta tcttatcatg tctgtatacc    4440
gtcgacctct agctagagct tggcgtaatc atggtcatag ctgtttcctg tgtgaaattg    4500
```

```
ttatccgctc acaattccac acaacatacg agccggaagc ataaagtgta aagcctgggg      4560
tgcctaatga gtgagctaac tcacattaat tgcgttgcgc tcactgcccg ctttccagtc      4620
gggaaacctg tcgtgccagc tgcattaatg aatcggccaa cgcgcgggga gaggcggttt      4680
gcgtattggg cgctcttccg cttcctcgct cactgactcg ctgcgctcgg tcgttcggct      4740
gcggcgagcg gtatcagctc actcaaaggc ggtaatacgg ttatccacag aatcagggga      4800
taacgcagga aagaacatgt gagcaaaagg ccagcaaaag gccaggaacc gtaaaaaggc      4860
cgcgttgctg gcgtttttcc ataggctccg cccccctgac gagcatcaca aaaatcgacg      4920
ctcaagtcag aggtggcgaa acccgacagg actataaaga taccaggcgt ttccccctgg      4980
aagctccctc gtgcgctctc ctgttccgac cctgccgctt accggatacc tgtccgcctt      5040
tctcccttcg ggaagcgtgg cgctttctca tagctcacgc tgtaggtatc tcagttcggt      5100
gtaggtcgtt cgctccaagc tgggctgtgt gcacgaaccc cccgttcagc ccgaccgctg      5160
cgccttatcc ggtaactatc gtcttgagtc caacccggta agacacgact tatcgccact      5220
ggcagcagcc actggtaaca ggattagcag agcgaggtat gtaggcggtg ctacagagtt      5280
cttgaagtgg tggcctaact acggctacac tagaagaaca gtatttggta tctgcgctct      5340
gctgaagcca gttaccttcg gaaaaagagt tggtagctct tgatccggca aacaaaccac      5400
cgctggtagc ggtggttttt tgtttgcaa gcagcagatt acgcgcagaa aaaaaggatc      5460
tcaagaagat cctttgatct tttctacggg gtctgacgct cagtggaacg aaaactcacg      5520
ttaagggatt ttggtcatga gattatcaaa aaggatcttc acctagatcc ttttaaatta      5580
aaaatgaagt tttaaatcaa tctaaagtat atatgagtaa acttggtctg acagttacca      5640
atgcttaatc agtgaggcac ctatctcagc gatctgtcta tttcgttcat ccatagttgc      5700
ctgactcccc gtcgtgtaga taactacgat acgggagggc ttaccatctg gccccagtgc      5760
tgcaatgata ccgcgagacc cacgctcacc ggctccagat ttatcagcaa taaaccagcc      5820
agccggaagg gccgagcgca gaagtggtcc tgcaacttta tccgcctcca tccagtctat      5880
taattgttgc cgggaagcta gagtaagtag ttcgccagtt aatagtttgc gcaacgttgt      5940
tgccattgct acaggcatcg tggtgtcacg ctcgtcgttt ggtatggctt cattcagctc      6000
cggttcccaa cgatcaaggc gagttacatg atccccatg ttgtgcaaaa aagcggttag      6060
ctccttcggt cctccgatcg ttgtcagaag taagttggcc gcagtgttat cactcatggt      6120
tatggcagca ctgcataatt ctcttactgt catgccatcc gtaagatgct ttctgtgac       6180 tggtgagtac tcaaccaagt cattctgaga atagtgtatg cggcgaccga gttgctcttg      6240
cccggcgtca atacgggata ataccgcgcc acatagcaga actttaaaag tgctcatcat      6300
tggaaaacgt tcttcgggc gaaaactctc aaggatctta ccgctgttga tccagttc       6360 gatgtaaccc actcgtgcac ccaactgatc ttcagcatct tttactttca ccagcgtttc      6420
tgggtgagca aaaacaggaa ggcaaaatgc cgcaaaaaag gaataagggc gacacggaa       6480 atgttgaata ctcatactct tcctttttca atattattga agcatttatc agggttattg      6540
tctcatgagc ggatacatat ttgaatgtat ttagaaaaat aaacaaatag gggttccgcg      6600
cacatttccc cgaaaagtgc cacctgacgt c                                     6631
```

<210> SEQ ID NO 2
<211> LENGTH: 6733
<212> TYPE: DNA
<213> ORGANISM: Artificial Sequence
<220> FEATURE:
<223> OTHER INFORMATION: vector

<400> SEQUENCE: 2

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagt     900
taagcttggt accgagctcg gatccgccac catgctggcc aggaagagca tcatcccgga     960
ggagtatgtg ctggcccgca tcgcggcgga gaacctgcgc aaaccgcgca tccgcgaccg    1020
cctccccaaa gcccgcttca tcgccaagag cggagcctgc aacctggctc acaagaacat    1080
ccgagagcaa ggtcgcttcc tgcaggacat cttcaccacc ttggtagacc tgaagtggcg    1140
tcacacgctg gtcatcttca ccatgtcctt cctctgcagc tggctgctct tcgctatcat    1200
gtggtggctg gtggccttcg cccacgggga catctatgct tacatggaga aaggcatcac    1260
ggagaagagt ggcctggagt ctgccgtctg tgtgaccaat gtcaggtcat tcacttctgc    1320
gtttctcttc tccatcgagg ttcaagtgac cattgggttt ggaggagaa tgatgactga    1380
ggagtgccct ctggccatca cggttttgat tctgcagaac attgtgggtc tgatcatcaa    1440
cgcggtcatg ttgggctgca tcttcatgaa gacggcccag gcccacgaaa gggcagagac    1500
gctgattttc agccgccatg ctgtaattgc ggtccgtaat ggcaagctgt gcttcatgtt    1560
ccgggtgggt gacctgagga aaagcatgat cattagcgcc tcggtgcgca tccaggtggt    1620
caagaaaacc acgacgccag aaggagaggt ggtgccctatt caccagcagg acatccctgt    1680
ggataatccc atcgagagca ataacatctt cctagtggcc cctttgatca tctgccatgt    1740
gattgataag cgtagccccc tgtacgatat ctcagccact gaccttgtca accaagacct    1800
ggaggtcata gtgattctcg agggcgtggt ggaaaccacg gcatcacca cgcaagcgcg    1860
gacctcctac attgcagagg agatccagtg gggacaccgc ttcgtgtcga ttgtgactga    1920
ggaggaggga gtgtactctg tggactattc taaatttggt aatactgtga gagtggcggc    1980
gccaagatgc agtgcccggg agctggacga gaaaccttcc atcttgattc agaccctcca    2040
aaaagagtgaa ctgtcgcacc agaattctct gaggaagcgc aactctatga aagaaacaa    2100
ctccatgagg aggagcaact ccatccggag gaataactct ccctcatgg tgcccaaggt    2160
gcaattcatg actccagaag gaaaccagtg cccatcagaa tcatgatagc ggccgctcga    2220
gtctagaggg cccttcgaac aaaaactcat ctcagaagag gatctgaata tgcataccgg    2280
```

```
tcatcatcac catcaccatt gagtttaaac ccgctgatca gcctcgactg tgccttctag    2340
ttgccagcca tctgttgttt gcccctcccc cgtgccttcc ttgaccctgg aaggtgccac    2400
tcccactgtc ctttcctaat aaaatgagga aattgcatcg cattgtctga gtaggtgtca    2460
ttctattctg gggggtgggg tggggcagga cagcaagggg gaggattggg aagacaatag    2520
caggcatgct ggggatgcgg tgggctctat ggcttctgag gcggaaagaa ccagctgggg    2580
ctctaggggg tatccccacg cgccctgtag cggcgcatta agcgcggcgg gtgtggtggt    2640
tacgcgcagc gtgaccgcta cacttgccag cgccctagcg cccgctcctt tcgctttctt    2700
cccttccttt ctcgccacgt tcgccggctt tccccgtcaa gctctaaatc ggggctccc     2760 tttagggttc cgatttagtg ctttacggca cctcgacccc aaaaaacttg attagggtga    2820
tggttcacgt agtgggccat cgccctgata cggttttt cgcccttga cgttggagtc       2880 cacgttcttt aatagtggac tcttgttcca aactggaaca acactcaacc ctatctcggt    2940
ctattctttt gatttataag ggattttgcc gatttcggcc tattggttaa aaaatgagct    3000
gatttaacaa aaatttaacg cgaattaatt ctgtggaatg tgtgtcagtt agggtgtgga    3060
aagtccccag gctccccagc aggcagaagt atgcaaagca tgcatctcaa ttagtcagca    3120
accaggtgtg gaaagtcccc aggctcccca gcaggcagaa gtatgcaaag catgcatctc    3180
aattagtcag caaccatagt cccgccccta actccgccca tcccgcccct aactccgccc    3240
agttccgccc attctccgcc ccatggctga ctaattttttt tatttatgc agaggccgag    3300 gccgcctctg cctctgagct attccagaag tagtgaggag gcttttttgg aggcctaggc    3360
ttttgcaaaa agctcccggg agcttgtata tccattttcg gatctgatca agagacagga    3420
tgaggatcgt ttcgcatgat tgaacaagat ggattgcacg caggttctcc ggccgcttgg    3480
gtggagaggc tattcggcta tgactgggca caacagacaa tcggctgctc tgatgccgcc    3540
gtgttccggc tgtcagcgca ggggcgcccg gttcttttg tcaagaccga cctgtccggt     3600
gccctgaatg aactgcagga cgaggcagcg cggctatcgt ggctggccac gacgggcgtt    3660
ccttgcgcag ctgtgctcga cgttgtcact gaagcgggaa gggactggct gctattgggc    3720
gaagtgccgg ggcaggatct cctgtcatct caccttgctc ctgccgagaa agtatccatc    3780
atggctgatg caatgcggcg gctgcatacg cttgatccgg ctacctgccc attcgaccac    3840
caagcgaaac atcgcatcga gcgagcacgt actcggatgg aagccggtct tgtcgatcag    3900
gatgatctgg acgaagagca tcaggggctc gcgccagccg aactgttcgc caggctcaag    3960
gcgcgcatgc ccgacggcga ggatctcgtc gtgacccatg gcgatgcctg cttgccgaat    4020
atcatggtgg aaaatggccg cttttctgga ttcatcgact gtggccggct gggtgtggcg    4080
gaccgctatc aggacatagc gttggctacc cgtgatattg ctgaagagct tggcggcgaa    4140
tgggctgacc gcttcctcgt gctttacggt atcgccgctc ccgattcgca gcgcatcgcc    4200
ttctatcgcc ttcttgacga gttcttctga gcgggactct ggggttcgcg aaatgaccga    4260
ccaagcgacg cccaacctgc catcacgaga tttcgattcc accgccgcct tctatgaaag    4320
gttgggcttc ggaatcgttt tccgggacgc cggctggatg atcctccagc gcgggatct     4380 catgctggag ttcttcgccc accccaactt gtttattgca gcttataatg gttacaaata    4440
aagcaatagc atcacaaatt tcacaaataa agcattttt tcactgcatt ctagttgtgg     4500
tttgtccaaa ctcatcaatg tatcttatca tgtctgtata ccgtcgacct ctagctagag    4560
cttggcgtaa tcatggtcat agctgtttcc tgtgtgaaat tgttatccgc tcacaattcc    4620
acacaacata cgagccggaa gcataaagtg taaagcctgg ggtgcctaat gagtgagcta    4680
```

```
actcacatta attgcgttgc gctcactgcc cgctttccag tcgggaaacc tgtcgtgcca    4740
gctgcattaa tgaatcggcc aacgcgcggg gagaggcggt ttgcgtattg ggcgctcttc    4800
cgcttcctcg ctcactgact cgctgcgctc ggtcgttcgg ctgcggcgag cggtatcagc    4860
tcactcaaag gcggtaatac ggttatccac agaatcaggg gataacgcag gaaagaacat    4920
gtgagcaaaa ggccagcaaa aggccaggaa ccgtaaaaag gccgcgttgc tggcgttttt    4980
ccataggctc cgcccccctg acgagcatca aaaaatcga cgctcaagtc agaggtggcg    5040
aaacccgaca ggactataaa gataccaggc gtttccccct ggaagctccc tcgtgcgctc    5100
tcctgttccg accctgccgc ttaccggata cctgtccgcc tttctccctt cgggaagcgt    5160
ggcgctttct catagctcac gctgtaggta tctcagttcg gtgtaggtcg ttcgctccaa    5220
gctgggctgt gtgcacgaac ccccgttca gcccgaccgc tgcgccttat ccggtaacta    5280
tcgtcttgag tccaacccgg taagacacga cttatcgcca ctggcagcag ccactggtaa    5340
caggattagc agagcgaggt atgtaggcgg tgctacagag ttcttgaagt ggtggcctaa    5400
ctacggctac actagaagaa cagtatttgg tatctgcgct ctgctgaagc cagttacctt    5460
cggaaaaaga gttggtagct cttgatccgg caaacaaacc accgctggta gcggtggttt    5520
ttttgtttgc aagcagcaga ttacgcgcag aaaaaaagga tctcaagaag atcctttgat    5580
cttttctacg gggtctgacg ctcagtggaa cgaaaactca cgttaaggga ttttggtcat    5640
gagattatca aaaaggatct tcacctagat ccttttaaat taaaaatgaa gttttaaatc    5700
aatctaaagt atatatgagt aaacttggtc tgacagttac caatgcttaa tcagtgaggc    5760
acctatctca gcgatctgtc tatttcgttc atccatagtt gcctgactcc ccgtcgtgta    5820
gataactacg atacgggagg gcttaccatc tggccccagt gctgcaatga taccgcgaga    5880
cccacgctca ccggctccag atttatcagc aataaaccag ccagccggaa gggccgagcg    5940
cagaagtggt cctgcaactt tatccgcctc catccagtct attaattgtt gccgggaagc    6000
tagagtaagt agttcgccag ttaatagttt gcgcaacgtt gttgccattg ctacaggcat    6060
cgtggtgtca cgctcgtcgt ttggtatggc ttcattcagc tccggttccc aacgatcaag    6120
gcgagttaca tgatccccca tgttgtgcaa aaaagcggtt agctccttcg gtcctccgat    6180
cgttgtcaga agtaagttgg ccgcagtgtt atcactcatg gttatggcag cactgcataa    6240
ttctcttact gtcatgccat ccgtaagatg cttttctgtg actggtgagt actcaaccaa    6300
gtcattctga gaatagtgta tgcggcgacc gagttgctct tgcccggcgt caatacggga    6360
taataccgcg ccacatagca gaactttaaa agtgctcatc attggaaaac gttcttcggg    6420
gcgaaaactc tcaaggatct taccgctgtt gagatccagt tcgatgtaac ccactcgtgc    6480
acccaactga tcttcagcat cttttacttt caccagcgtt tctgggtgag caaaaacagg    6540
aaggcaaaat gccgcaaaaa agggaataag ggcgacacgg aaatgttgaa tactcatact    6600 cttcctttt caatattatt gaagcattta tcagggttat tgtctcatga gcggatacat    6660
atttgaatgt atttagaaaa ataaacaaat aggggttccg cgcacatttc cccgaaaagt    6720
gccacctgac gtc                                                      6733
```